United States Patent
Perron et al.

(10) Patent No.: US 6,579,526 B1
(45) Date of Patent: *Jun. 17, 2003

(54) VIRAL MATERIAL AND NUCLEOTIDE FRAGMENTS ASSOCIATED WITH MULTIPLE SCLEROSIS, FOR DIAGNOSTIC, PROPHYLACTIC AND THERAPEUTIC PURPOSES

(75) Inventors: Herve Perron, Lyons (FR); Frederic Beseme, Villefontaine (FR); Frederic Bedin, Lyons (FR); Glaucia Paranhos-Baccala, Lyons (FR); Florence Komurian-Pradel, Saint Cyr Au Mont D'Or (FR); Colette Jolivet-Reynaud, Bron (FR); Bernard Mandrand, Villeurbanne (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/374,766

(22) Filed: Aug. 16, 1999

Related U.S. Application Data

(62) Division of application No. 08/691,563, filed on Aug. 2, 1996, now Pat. No. 6,001,987.

(30) Foreign Application Priority Data

Aug. 3, 1995 (FR) ............................................ 95 09643

(51) Int. Cl.$^7$ ........................ A61K 39/12; C12P 19/34; C07H 21/04
(52) U.S. Cl. ................................ 424/204.1; 424/185.1; 424/187.1; 424/199.1; 435/91.1; 435/91.33; 530/300; 530/350; 536/23.72
(58) Field of Search ...................... 536/23.72; 435/91.1, 435/91.33, 235.1; 424/185.1, 187.1, 199.1, 204.1; 530/350, 300

(56) References Cited

U.S. PATENT DOCUMENTS

| | | | |
|---|---|---|---|
| 4,311,686 A | 1/1982 | Angers et al. | |
| 4,346,074 A | 8/1982 | Gilmour et al. | |
| 4,388,298 A | 6/1983 | Nazerian et al. | |
| 4,396,600 A | 8/1983 | Messineo et al. | |
| 4,520,113 A | 5/1985 | Gallo et al. | |
| 4,647,773 A | 3/1987 | Gallo et al. | |
| 4,708,818 A | 11/1987 | Montagnier et al. | |
| 4,900,553 A | 2/1990 | Silver et al. | |
| 5,158,976 A | 10/1992 | Rosenburg et al. | |
| 5,219,837 A | 6/1993 | Cohen et al. | |
| 5,225,352 A | 7/1993 | Zanetta et al. | |
| 5,494,807 A | * 2/1996 | Paoletti et al. | 435/69.3 |
| 5,580,766 A | * 12/1996 | Mason et al. | 435/172.1 |
| 5,585,262 A | 12/1996 | Perron et al. | |
| 5,650,318 A | 7/1997 | Perron et al. | |
| 5,691,147 A | * 11/1997 | Draetta et al. | 435/7.1 |
| 5,710,037 A | * 1/1998 | Vanin et al. | 435/240.2 |
| 5,800,980 A | 9/1998 | Perron et al. | |
| 5,871,745 A | 2/1999 | Perron et al. | |
| 5,871,996 A | 2/1999 | Perron et al. | |
| 5,962,217 A | 10/1999 | Perron et al. | |

FOREIGN PATENT DOCUMENTS

| | | |
|---|---|---|
| EP | 0 222 310 | 5/1987 |
| EP | 0 326 395 | 8/1989 |
| WO | 93/07259 | 4/1993 |
| WO | 93/20188 | 10/1993 |
| WO | WO 93/23550 | 11/1993 |
| WO | WO 94/28138 | 12/1994 |
| WO | WO 95/21256 | 8/1995 |

OTHER PUBLICATIONS

Koop et al, 1994, Genomics 19 (3), 478–493.*

Takeuchi, "Expression of human endogenous retrovirus in rheumatoid arthritis", Hakkaido Igku Zasshi. vol. 69(4), pp. 821–835. (1994) (Abstract only).

Boswell et al., "Sequence comparison and alignment: the measurement and interpretation of sequence similarity" Oxford Press, pp. 161–178 (1988).

Acha–Orbea et al., "Mls—A Retrovirus Exploits the Immune System", *Immunology Today,* vol. 12, No. 10, 1991, pp. 356–361.

Asai et al., "J. of Neurochem", vol. 59, No. 1, pp. 307–317, 1992.

*ATCC Catalogue of Cell Lines and Hybridomas,* Sixth Edition, 1988, pp. 165 and 344–355.

C.R.M. Bangham et al., "PCR Analysis of DNA from Multiple Sclerosis Patients for the Presence of HTLV–I", *Science,* vol. 246, Nov. 10, 1989, pp. 821–824.

R. Baccala et al., "Genomically Imposed and Somatically Modified Human Thymocyte vb Gene Repertoires", *Proc. Natl. Acad. Sci.,* vol. 88, pp. 2908, 1991.

J. Bai et al., "Unique Long Terminal repeat U3 Sequences Distinguish Exogenous Jaagsiekte Sheep Retroviruses Associated with Ovine Pulmonary Carcinoma from Endogenous Loci in the Sheep Genome", *J. Virol.,* vol. 70, pp. 3159–3168, (1996).

Barna et al., "Human Astrocytes Proliferate in Response to Tumor Necrosis Factor Alpha", *J. Neuroimmunol.,* 30 (1990), pp. 239–243.

Beck et al., "Increased Production of Interferon Gamma and Tumor Necrosis Factor Precedes Clinical Manifestation in Multiple Sclerosis: Do Cytokines Trigger Off Exacerbations?", *Acta Neurol. Scand.,* 1988: 78, pp. 318–323.

(List continued on next page.)

Primary Examiner—Ali R. Salimi
(74) Attorney, Agent, or Firm—Oliff & Berridge, PLC

(57) ABSTRACT

Viral material, in the isolated or purified state, in which the genome comprises a nucleotide sequence chosen from the group including sequences SEQ ID NO:46, SEQ ID NO:51, SEQ ID NO:52, SEQ ID NO:53 and SEQ ID NO:56, their complementary sequences and their equivalent sequences, in particular nucleotide sequences displaying, for any succession of 100 contiguous monomers, at least 50% and preferably at least 70% homology with the said sequences SEQ ID NO:46, SEQ ID NO:51, SEQ ID NO:52, SEQ ID NO:53 and SEQ ID NO:56, respectively, and their complementary sequences.

8 Claims, 49 Drawing Sheets

OTHER PUBLICATIONS

J. I. Bell et al., "Multiple Loci for Multiple Sclerosis", *Nature Genetics,* vol. 13, pp. 377–378, (1996).

Bergamini et al., "Multiple Sclerosis. I. The Immune Pathogenetic Hypothesis", *Riv. Neurol.,* vol. 59, No. 5, Oct. 1989, pp. 176–190.

T. Bergström et al., "Isolation of Herpes Virus Type 1 During First Attack of Multiple Sclerosis.", *Annales Neurology,* vol. 26, pp. 283–285, (1989).

Bernton et al., "No Direct Neuronotoxicity by HIV–1 Virions or Culture Fluids from HIV–1 Infected HIV–1 Infected T Cells or Monocytes", *Aids Research and Human Retroviruses,* vol. 8, No. 4, 1992, pp. 495–503.

Birnbaum et al., "Spinal Fluid Lymphocytes from a Sub-Group of Multiple Sclerosis Patients Respond to Mycobacterial Antigens", *Ann. Neurol.,* vol. 34, No. 1, Jul. 1993, pp. 18–24.

Bjare, "Serum–Free Cell Culture", *Pharmac. Ther.,* vol. 53, 1992, pp. 355–374.

C. Bosgiraud et al., "Ultrastructural Study on Visna Virus in Sheep Plexus Choroid Cells", *Biological Abstracts,* vol. 83, No. 7, 1987.

Boyle et al., "Cellular Immune Response in Multiple Sclerosis Plaques", *American Journal of Pathology,* vol. 137, No. 3, Sep. 1990, pp. 575–584.

Bradford, "A Rapid and Sensitive Method for the Quantitation of Microgram Quantities of Protein Utilizing the Principle of Protein–Dye Binding," *Anal. Biochem.,* 72, 1976, pp. 248–254.

Brocke et al., "Induction of Relapsing Paralysis in Experimental Autoimmune Encephalomyelitis by Bacterial Superantigen", *Nature,* vol. 365, Oct. 14, 1993, pp. 642–644.

Calder, et al., "MS: A Localized Immune Disease of the Central Nervous System", *Immunology Today,* vol. 10, No. 3, 1989, pp. 99–103.

Carp et al., "Viral Etiology of Multiple Sclerosis", *Prog. Med. Virol.,* vol. 24, pp. 158–177, 1978.

Charcot, "Histologie de la sclerose en plaques [Histology of Multiple Sclerosis]", Gaz. Hop. (Paris), 1868; 41, 554–66.

Chomczynski et al., "Single–Step Method of RNA Isolation by Acid Guanidinium Thiocyanate–Phenol–Chloroform Extraction", *Anal. Biochem.,* 1987, vol. 162, pp. 156–159.

Cole et al., "The Mycoplasma Arthritidis T–Cell Mitogen, MAM: A Model Superantigen", *Immunology Today,* vol. 12, No. 8, 1991, pp. 271–276.

Cook et al., "Multiple Sclerosis and Distemper in Iceland 1966–1978", *Acta Neurol. Scandinav.* 61, 1980, pp. 244–251.

Dalgleish et al., "Do Human T–Lymphotrophic Viruses (HTLVs) and Other Enveloped Viruses Induce Autoimmunity in Multiple Sclerosis?", *Neuropath. App. Neurobiol.,* 1987, 13, pp. 241–250.

A. N. Davison et al., "Biosynthesis of Myelin and Neurotoxic Factors in the Serum of Multiple Sclerosis Patients", *Advances in Experimental Medicine and Biology,* vol. 100, pp. 19–25, 1978.

De Keyser, "Autoimmunity in Multiple Sclerosis", *Neurology,* 38, Mar. 1988, pp. 371–374.

S. Dhib–Jalbut et al., "Measles Virus Polypeptide–Specific Antibody Profile in Multiple Sclerosis", *Neurology,* vol. 40, pp. 430–435, (1990).

Dunn et al., "A Novel Method to Map Transcripts: Evidence for Homology Between an Adenovirus mRNA and Discrete Multiple Regions of the Viral Genome", *Cell,* vol. 12, Sep. 1977, pp. 23–36.

Ebers et al., "The Geography of MS Reflects Genetic Susceptidility", *Neurology,* 36, Apr. 1986, Suppl. 1, p. 108.

Elian et al., "Multiple Sclerosis Among United Kingdom–Born Children of Immigrants from the Indian Subcontinent, Africa and the West Indies", *J Neurol Neurosurg Psychiat,* 1990; 53, pp. 906–911.

Escourolle et al., "Principales Donnees Morphologiques Approches Physiopathologiques et Etiologiques de la Sclerose en Plaques [Principal Morphological Data, Physiopathological and Etiological Approaches to Multiple Sclerosis]", *La Reveue du Praticien,* Paris, 1980; 30, pp. 2047–2053.

E. J. Field, "Immunological Treatment for Multiple Sclerosis", *The Lancet,* Jun. 3, 1989, p. 1272.

Frohman et al., "Rapid Production of Full–Length cDNAs from Rare Transcripts: Amplification Using a Single Gene–Specific Oligonucleotide Primer", *Proc. Natl. Acad. Sci. USA,* 1988, vol. 85, pp. 8998–9002.

Medline Abstract of FU et al., "Rabies virus nucleoprotein expressed in and purified from insect cells is efficacious as a vaccine," Proc Natl Acad Sci USA 88: 2001–05 (1991).

Galiana et al., "Establishment of Permanent Astroglial Cell Lines, Able to Differentiate in Vitro, From Transgenic Mice Carrying the Polyoma Virus Large T Gene: An Alternative Approach to Brain Cell Immortalization", *Journal of Neuro–science Research,* 1990; 26: pp. 269–277.

M. B. Gardner et al., "Congenital Transmission of Murine Leukaemia Virus from Wild Mice Prone to Development of Lymphoma and Paralysis", *J. Natl. Cancer Inst.,* vol. 62, pp. 63–69, (1979).

M. B. Gardner, "Genetic resistance to a Retroviral Neurologic Disease in Wild Mice, in Retrovirus Infections of the Nervous System", *Oldstone M.B.A. and Koprowsky H. Eds. Current Topice in Microbiology and Immunology,* No. 160, pp. 3–10, (Springer–Verlag, Berlin, 1990).

Gay, "Is Multiple Sclerosis Caused by an Oral Spirochaete", *The Lancet,* Jul. 12, 1986, pp. 75–77.

A. Gessain et al., "Intrathecal Synthesis of Antibodies to Human T Lymphotropic Virus Type I and the Presence of IgG Oligoclonal Bands in the Cerebrospinal Fluid of Patients with Endemic Tropical Spastic Paraparesis", *The Journal of Infectious Diseases,* vol. 157, No. 6, Jun. 1988, pp. 1226–1234.

A. Gessain et al., Antibodies to Human T–Lymphotrophic Virus type–I in Patients with Tropical Spastic Paraparesis, *Lancet,* vol. 2, pp. 407–410, (1985).

Giulian et al., "The Envelope Glycoprotein of Human Immunodeficiency Virus Type 1 Stimulates Release of Neurotoxins from Monocytes", *Proc. Natl. Acad. Sci. USA,* vol. 90, 1993, pp. 2769–2773.

D. Giulian et al., "Secretion of Neurotoxins by Mononuclear Phagocytes Infected with HIV–1", Science, vol. 250, Dec. 14, 1990, pp. 1593–1596.

Gonzalez–Scarano et al., "Multiple Sclerosis Disease Activity Correlates with Gadolinium–Enhanced Magnetic Resonance Imaging", *Annals of Neurology,* vol. 21, No. 3, Mar. 1987, pp. 300–306.

F. Gonzalez–Scarano et al., "Sequence Similarities Between Human Immunodeficiency Virus gp41 and Paramyxovirus Fusion Proteins.", *AIDS Res. Hum. Retrov.*, vol. 3, pp. 245–252, (1987).

R. Gonzales–Quintial et al., *J. Clin. Invest.*, vol. 97, No. 5, pp. 1335–1343, 1996.

S.J. Greenberg et al., "Detection of sequences homolgous to human retroviral DNA in multiple sclerosis by gene amplification", *Proc. Natl. Acad. Sci. USA*, vol. 86, Arp. 1989, pp. 2878–2882.

S. Haahr et al., "A Putative New Retrovirus Associated with Multiple Sclerosis and the Possible Involvement of Epstein-–Barr Virus in this Disease", *NY Acad. Science*, vol. 724, pp. 148–156, 1994.

S. Haahr et al., "Is Multiple Sclerosis Caused by a Dual Infection with Retrovirus and Epstein–Barr Virus?", *Neuroepidemiology*, vol. 11, pp. 299–303, (1992).

S. Haahr et al., "Just Another Dubious Virus in Cells from a Patient with Multiple Sclerosis?", *The Lancet*, vol. 337, Apr. 6, 1991, pp. 863–864.

A. T. Haase, "Pathogenesis of Lentivirus Infections", *Nature*, vol. 322, Jul. 10, 1986, pp. 130–136.

Haegert et al. HLA–DRβ, –DQα, and –DQβRestriction Fragment Length Polymorphisms in Multiple Sclerosis, *J. Neurosci. Res.*, 1989; 23, pp. 46–54.

S.L. Hauser et al., "Analysis of Human T–lymphotropic virus sequences in multiple sclerosis tissue", *Nature*, vol. 322, Jul. 10, 1986, pp. 176–178.

Hauw et al., "Aspects Anatomo–Pathologiques de la Sclerose en Plaques [Anatomopathological Aspects of Multiple Sclerosis]", *La Sclerose en Plaques [Multiple Sclerosis]*, 9–47 (Rascol et al. eds., 1980).

Hirayama et al., "Serum–Mediated Oligodendrocyte Cytotoxicity in Multiple Sclerosis patients and Controls", *Neurology* 1986, vol. 36, pp. 276–278.

Hoffman et al., "Handbook of Clinical Neurology, 12; Viral Diseases", R.R. McKendall, ed., Elsevier Science Publishing, Amsterdam, 1989, pp. 453–466.

Huang, "Defective Interfering Viruses", *Fundamental Virology*, Fields et al., eds., 1986, pp. 101–117.

Huck et al., "J. of Neurosei", vol. 4, No. 10, pp. 2650–2657, 1984.

A. W. Hugin et al., "A Virus–Encoded Superantigen in a Retrovirus–Induced Immunodeficiency Syndrome of Mice", *Science*, vol. 252, pp. 424–427, (1991).

James, "Multiple Sclerosis or Blood–Brain Barrier Disease", *The Lancet*, Jan. 7 1989, p. 46.

Medline abstract of Jarrett et al., "Studies on vaccination against papillomaviruses: a comparison of purified virus, tumour extract and transformed cells in prophylactic vaccination," Vet Rec 126: 449–52 (1990).

Jervis et al., "Experimental Allergic Encephalomyelitis", *J. Neuropathol. Exp. Neurol.*, 1948; 7, pp. 309–320.

D. Johnson et al., "Quantitation of the Myelin–Associated Glycoprotein in Human Nervous Tissue from Controls and Multiple Sclerosis Patients", *Journal of Neurochemistry*, vol. 46, No. 4, 1986, pp. 1086–1093.

Johnson, "Viral Aspects of Multiple Sclerosis", *Handbook of Clinical Neurology*, vol. 3(47): Demyelinating Diseases, 1985, pp. 319–336.

R.T. Johnson, "Nononcogenic Retrovirus Infections as Models for Chronic and Relapsing Human Diseases: Introduction", *Reviews of Infectious Diseases*, vol. 7, No. 1, Jan.–Feb. 1985, pp. 66–67.

Juntunen et al. "Multiple Sclerosis and Occupational Exposure to Chemicals: A Co–Twin Study of a Nationwide Series of Twins", *Br. J. Int. Med.*, 1989; 46: pp. 417–419.

Karpas et al., "Lack of evidence for involvement of known human retroviruses in multiple sclerosis", *Nature*, vol. 322, Jul. 10, 1986, pp. 177–178.

Kent et al., "Cerebral Blood Flow, Cerebral Metabolism and Blood–Brain Barrier," *Handbook of Clinical Neurology*, vol. 56(12), 1989, pp. 79–91.

H. Koprowski et al., "Multiple sclerosis and human T–cell lymphotropic retroviruses", *Nature*, vol. 318, Nov. 14, 1985, pp. 154–160.

G. La Mantia et al., "Identification of New Human Repetitive Sequences: Characterization of the Corresponding cDNAs and their Expression in Embryonal Carcinoma Cells", *Nucleic Acids Research*, vol. 17, No. 15, 5913–5922, (1989).

G. La Mantia et al., "Identification and Characterization of Novel Human Endogenous Retrovirual Sequences Prefentially Expressed in Undifferentiated Embryonal Carcinoma Cells", *Nucleic Acids Res.*, 1991, vol. 19, No. 7, pp. 1513–1520.

H. Lassmann et al., "Chronic Relapsing Experimental Allergic Encephalomyelitis–Clinicopathological Comparison with Multiple Sclerosis", Arch Neurol, vol. 36, Aug. 1979, pp. 490–497.

Boswell, D. Ross and Lesk, Arthur M., "Sequence Comparison and alignment: the measurement and interpretation of sequence similarity", *Computational Moecular Biology*, 1988.

Medline abstract of LEAO, "Tuberculosis: new strategies for the development of diagnostic tests and vaccines," Braz J Med Biol Res 26: 827–33 (1993).

Levi et al., Human Immunodeficiency Coat Protein gp120 Inhibits the β–adrenergic Regulation of Astroglial and Microglial Functions, *Proc. Natl. Acad. Sci. USA*, vol. 90, Feb. 1993, pp. 1541–1545.

Levine et al., "Conversion of Lytic to Persistent Alphavirus Infection by the bcl–2 Cellular Oncogene", *Nature*, vol. 361, Feb. 25, 1993, pp. 739–742.

Y.S. Lie Et Al., Journal of Virology, vol. 38, No. 12, Dec. 1994, pp. 7840–7849, "Chinese hamster ovary cells contain transcriptionally active full length type C provirises".

Linial et al., "Retroviral RNA Packaging: Sequence Requirements and Implications", in *Current Topics in Microbiology and Immunobiology. Retroviruses, Strategies of Replication*, Swanstrom et al., eds., vol. 157, 1990, pp. 125–152.

R. Lisak et al., "In Vitro Cell–Mediated Immunity of Cerebrospinal–Fluid Lymphocytes to Myelin Basic Protein in Primary Demyelinating Diseases", *The New England Journal of Medicine*, vol. 297, No. 16, Oct. 20, 1977, pp. 850–853.

Lo et al., "Newly Discovered Mycoplasm Isolated from Patients Infected with HIV", *The Lancet*, vol. 338, Dec. 7, 1991, pp. 1415–1418.

Lori et al., "Viral DNA Carried by Human Immunodeficiency Virus Type 1 Virions", *J. Virol.*, vol. 66, No. 8, Aug. 1992, pp. 5067–5074.

F. Mallet et al., "Continuons RT–PCR and taq DNA Polymerase: Characterization and Comparison to Uncoupled Procedures", *Biotechniques*, vol. 18, pp. 678–687, 1985.

Mallet et al., "Enzyme–Linked Oligosorbent Assay for Detection of Polymerase Chain Reaction–Amplified Human Immunodeficiency Virus Type I", *J. Clin. Microbiol.,* Jun. 1993, vol. 31, No. 6, pp. 1444–1449.

Marie, "Sclerose en Plaques et Maladies Infectieuses [Multiple Sclerosis and Infectious Disease]", *Le Progres Medical,* 1884; 12, pp. 287–289.

P. Marrack et al., "A Maternally Inherited Superantigen Encoded by a Mammary Tumor Virus", *Nature,* vol. 349, pp. 524–526, (1991).

McDonald, "The Mystery of the Origin of Multiple Sclerosis", *J. Neurol. Neurosurg. Psych.,* 1986; 49, pp. 113–123.

J. Merregaert et al., "Nucleotide Sequence of a Radiation Leukemia Virus Genome", *Virology,* vol. 158, No. 1, pp. 88–102, (1987).

Meyerhans et al., "Temporal Fluctuations in HIV Quasispecies in Vivo Are Not Reflected by Sequential HIV Isolations", *Cell,* vol. 58, Sep. 8, 1989, pp. 901–910.

J.D. Mosca et al., "Activation of human immunodeficiency virus by herpesvirus infection: Identification of a region within the long terminal repeat that responds to a trans–acting factor encoded by herpes simplex virus 1", *Proceedings of the National Academy of Sciences of USA,* vol. 84, No. 21, Nov. 1987, pp. 7408–7412.

Mosmann, "Rapid Colorimetric Assay for Celluar Growth and Survival: Application to Proliferation and Cytotoxicity Assays", *Journal of Immunological Methods,* 65, 1983, pp. 55–63.

O. Narayan et al., "Lentiviral Diseases of Sheep and Goats: Chronic Pneumonia Leukoencephalomyelitis, and Arthritis", *Reveiws of Infectious Diseases,* vol. 7, No. 1, Jan.–Feb. 1985, pp. 89–98.

N. Nathanson et al., "Experimental Visna in Icelandic Sheep: The Prototype Lentiviral Infection", *Reviews of Infectious Diseases,* vol. 7, No. 1, Jan.–Feb. 1985, pp. 75–82.

Newell et al., "Ligation of Major Histocompatibility Complex Class II Molecules Mediates Apoptotic Cell Death in Resting B Lymphocytes", *Proc. Natl. Acad. Sci. USA,* vol. 90, Nov. 1993, pp. 10459–10463.

Nielsen et al., "Sequence–Selective Recognition of DNA by Strand Displacement with a Thymine–Substituted Polyamide", *Science,* vol. 254, pp. 1497–1500.

Norby, "Viral Antibodies in Multiple Sclerosis", *Prog. Med. Virol.,* vol. 24, 1978, pp. 1–39 (1978).

M. Ohta et al., "Sera from Patients with Multiple Sclerosis React with Human T Cell Lymphotropic Virus–I Gag Proteins but not Env Proteins—Western Blotting Analysis", *The Journal of Immunology,* vol. 137, No. 11, Dec. 1, 1986, pp. 3440–3443.

Medline abstract of Orlandi et al., "Characterization of the 175–kilodalton erythrocyte binding antigen of Plasmodium falciparum," Mol Biochem Parasitol 40: 285–94 (1990).

Ostrove et al., "Activation of the Human Innumodeficiency Virus by Herpes Simplex Virus Type 1", J Virol 61(12), Dec. 1987, pp. 3726–3732.

M. Palmarini, "The Exogenous Form of Jaagsiekte Retrovirus is Specifically Associated with a contagious Lung Cancer of Sheet", *J. Virol,* vol. 70, pp. 1618–1623, (1996).

J.L. Pablos et al., "A novel retroviral POL sequence is present in patients with rheumatoid arthritis", & American College of Rheumatology 57th Annual Scientific Meeting, Nov. 7–11, 1993 San Antonio, Texas, USA, *Arthritis and Rheumatism,* vol. 36, No. 9 supl. 1993, p. S55, Abstract No. 102.

Medline abstract of Pei et al., "Identificaiton, purification, and characterization of major antigenic proteins of Campylobacter jejuni," J Biol Chem 266: 16363–69 (1991).

H. Perron et al., "Isolations of an Unknown Retrovirus from CSF, Blood and Brain Cells of Patients with Multiple Sclerosis", in *Current Concepts in Multiple Sclerosis,* Wietholter et al., eds., 1991, Elsevier publ., pp. 111–116.

H. Perron et al., "Leptomeningeal cell line from multiple sclerosis with reverse transcriptase activity and viral particles", *Res. Virol.,* Nov. 1989, vol. 140(6), pp. 551–561.

H. Perron et al., "Leptomeningeal cell line from multiple sclerosis with reverse transcriptase activity and viral particles", Biological Abstracts, vol. 89, No. 9, May 1, 1990.

H. Perron et al., "Isolation of Retrovirus from Patients with Multiple Sclerosis", *The Lancet,* vol. 337, No. 8745, Apr. 6, 1991, pp. 862–863.

H. Perron et al., "Antibody to Reverse Transcriptase of Human Retrovirus in Multiple Sclerosis", Biological Abstracts, vol. 93, No. 6, Mar. 15, 1992.

H. Perron et al., "Herpes simplex virus ICPO and ICP4 immediate early proteins strongly enhance expression of a retrovirus harboured by a leptomeningeal cell line from a patient with multiple sclerosis", The Journal of General Virology, vol. 74, No. 1, Jan. 1993, pp. 65–72.

H. Perron et al., "Retrovirus Isolation from Patients with Multiple Sclerosis: Epiphenomenon or Causative Factor?", *AIDS Research and Human Retroviruses,* vol. 8, No. 5, May 1992, p. 922.

H. Perron et al., "In Vitro Transmission and Antigenicity of a Retrovirus Isolated from a Multiple Sclerosis Patient", *Res. Virol.,* vol. 143, No. 5, 1992, pp. 337–350.

Perron et al., "Retroviral Reactivation by Herpesviruses in MS: Serological Arguments", Current Concepts in Multiple Sclerosis 1991, pp. 331–332.

A. Plaza et al., Theofilopoulos, A.N. New Human vβ 12DD Genes and Polymorphic Variants. J. Imm; vol. 147, No. 12, pp. 4360–4665, 1991.

Poirier et al., "La Barriere Hemato–Encephalique. Donnees Morphologiques [The Blood–Brain Barrier. Morphological Data]", *La Revue de Medecine Interne,* vol. IV, No. 2, Jun. 1983, pp. 131–144.

J. L. Portis, "Wild Mouse Retrovirus: Pathogenesis in "Retrovirus Infections of the Nervous System. Oldstone M.B.A. and Koprowsky H. Eds. Current topics in microbiology and immunology, n°160, pp. 11–27, (Springer–Verlag, Berlin, 1990).

C.M. Poser et al., "New Diagnostic Criteria for Multiple Sclerosis: Guidelines for Research Protolcols, in "The diagnosis of Multiple Sclerosis"", *Thieme Stratton Inc.,* pp. 225–229, 1984.

D.N., Posnet, "Do Superantigens Play a Role in Autoimmunity?", *Semin. Immunol.,* vol. 5, pp. 65–72, 1993.

Prineas, "The Neuropathology of Multiple Sclerosis", *Handbook of Clinical Neurology,* vol. 3 (47), 1985, pp. 213–257.

Prineas et al., "Multiple Sclerosis: Remyelination of Nascent Lesions", *Annals of Neurology,* vol. 33, No. 2, Feb. 1993, pp. 137–151.

Prineas, "Pathology of the Early Lesion in Multiple Sclerosis", *Human Pathology*, vol. 6, No. 5, Sep. 1975, pp. 531–554.

Prineas et al., "Macrophages, Lymphocytes, and Plasma Cells in the Perivascular Compartment in Chronic Multiple Sclerosis", *Laboratory Investigation*, vol. 38, No. 4, 1978, pp. 409–421.

Ransohoff et al., "Heat–Shock Proteins and Autoimmunity: Implications for Multiple Sclerosis", *Annals of Neurology*, vol. 34, No. 1, Jul. 1993, pp. 5–7.

Rapoport, *Blood–Brain Barrier in Physiology and Medicine*, 129 (1976).

E.P. Reddy et al., "Amplification and Molecular Cloning of HTLV–I Sequences from DNA of Multiple Sclerosis Patients", *Science*, vol. 243, Jan. 27, 1989, pp. 529–533.

S. S. Rhee et al., "A single Amino Acid Substitution Within the Matrix Protein of a D–Type Retrovirus Converts Its Morphogenesis to that of a C–Type Retrovirus", Cell 63, pp. 77–86, (1990).

Riise et al., "Clustering of Residence of Multiple Sclerosis Patients at Age 13 to 20 Years in Hordaland, Norway", *Am J Epidemiol.* 1991, vol. 133, No. 9, pp. 932–939.

Robbins et al., "Production of Cytotoxic Factor for Oligodendrocytes by Stimulated Astrocytes", *The Journal of Immunology*, vol. 139, No. 8, Oct. 15, 1987, pp. 2593–2597.

Rosati et al., "Incidence of Multiple Sclerosis in the Town of Sassari, Sardinia, 1965 to 1985: Evidence for Increaseing Occurrence of the Disease", *Neurology* 38 (Mar. 1988), pp. 384–388.

Rudge, "Does a Retrovirally Encoded Superantigen Cause Multiple Sclerosis?", *J. Neurology Neurosurgery & Psychiatry* 1991, vol. 54, pp. 853–855.

Medline abstract of Rumschlag et al., "Immunologic characterization of a 35–kilodalton recombinant antigen of Mycobacterium tuberculosis," J Clin Microbiol 28: 591–95 (1990).

Medline abstract of Sakulramrung et al., "Antigenic and immunogenic characteristics of subcellular fractions and whole cells of a rough *E. coli* 0111 (J5) mutant," Immunobiology 169: 372–88 (1985).

Selmaj, et al., "Tumor Necrosis Factor Mediates Myelin and Oligodendrocyte Damage in Vitro", *Annals of Neurology*, vol. 23, No. 4, Apr. 1988, pp. 339–346.

Shih et al., "Detection of Multiple, Novel Reverse Transcriptase Coding Sequences in Human Nucleic Acids: Relation to Primate Retroviruses", *J. Virol.*, Jan. 1989, vol. 63, No. 1, pp. 64–75.

Silberberg et al., "Tissue Culture Demyelination by Normal Human Serum", *Annals of Neurology*, vol. 15, No. 6, Jun. 1994, pp. 575–580.

M. Sommerlund et al., "Retrovirus–like particles in an Epstein–Barr virus–producing cell line derived from a patient with chronic progressive myelopathy", *Acta Neurol Scand*, 1993: 87: pp. 71–76.

P. Sonigo et al., "Nucleotide Sequence of Mason–Pfizer Monkey Virus: An immunosuppressive D–Type Retrovirus", Cell 45, pp. 375–385, (1986).

Southern, "Detection of Specific Sequences Among DNA Fragments Separated by Gel Electrophoresis", *J. Mol. Biol.*, 1975, vol. 98, pp. 503–517.

Suzumura et al, "Serum Cytotoxicity to Oligodendrocytes in Multiple Sclerosis and Controls: Assessment by $^{51}$Cr Release Assay", *J. Neuroimmunol.*, 11 (1986), pp. 137–147.

Traugott, "Multiple Sclerosis: Relevance of Class I and Class II MHC–Expressing Cells to Lesion Development", *Journal of Neuroimmunology*, 16, 1987, pp. 283–302.

Waksman, "Mechanisms in Multiple Sclerosis", *Nature*, vol. 318, Nov. 14, 1985, pp. 104–105.

K.G. Warren et al., "Diagnostic Value of Cerebrospinal Fluid Anti–Myelin Basic Protein in Patients with Multiple Sclerosis", Annals of Neurology, vol. 20, No. 1, Jul. 1986, pp. 20–25.

Williams et al., "Molecular Regulation of Apoptosis: Genetic Controls on Cell Death", *Cell*, vol. 74, Sep. 10, 1993, pp. 777–779.

Wienfield et al., "Stress Proteins, Autoimmunity, and Autoimmune Disease", *Current Topics in Microbiology and Immunology*, vol. 167, Springer–Verlag, Berlin, 1991, pp. 161–189.

D. L. Wilkinson et al., "Evidence for a functional subclass of the RTLV–H family of human endogenous retrovirus–like sequences", *J. Virol.*, vol. 67, pp. 2981–2989, (1993).

Wollinsky et al., "Liquorpherese bei 10 Patienten mit Multiple Sklerose [Fluid Phoresis in 10 Patients With Multiple Sclerosis]", *Verhandlungen der Deutschen Gesellschaft fur Neurologie*, vol. 7, 1992, pp. 444–445.

Woodland, et al., "An Endogenous Retrovirus Mediating Deletion of αβ T Cells?", *Nature*, vol. 349, Feb. 7, 1991, pp. 529–530.

* cited by examiner

FIG. 1

```
Consensus    GTTTAGGGAT  ANCCCTCATC  TCTTTGGTCA  GGTACTGGCC  CAAGATCTAG   50
Consensus    GCCACTTCTC  AGGTCCAGSN  ACTCTGTYCC  TTCAG   85
```

SEQ ID NO 3 (POL MSRV-1B)

```
Consensus    GTTCAGGGAT  AGCCCCCATC  TATTTGGCCA  GGCACTAGCT  CAATACTTGA   50
Consensus    GCCAGTTCTC  ATACCTGGAC  AYTCTYGTCC  TTCGGT   86
```

SEQ ID NO 4 (POL MSRV-1B)

```
Consensus    GTTCARRGAT  AGCCCCCATC  TATTTGGCCW  RGYATTAGCC  CAAGACTTGA   50
Consensus    GYCAATTCTC  ATACCTGGAC  ACTCTTGTCC  TTYRG   85
```

SEQ ID NO 5 (POL MSRV-1B)

```
Consensus    GTTCAGGGAT  AGCTCCCATC  TATTTGGCCT  GGCATTAACC  CGAGACTTAA   50
Consensus    GCCAGTTCTY  ATACGTGGAC  ACTCTTGTCC  TTTGG   85
```

SEQ ID NO 6 (POL MSRV-1B)

```
Consensus    GTGTTGCCAC  AGGGGTTTAR  RGATANCYCY  CATCTMTTTG  GYCWRGYAYT
Consensus    RRCYCRAKAY  YTRRGYCAVT  TCTYAKRYSY  RGSNAYTCTB  KYCCTTYRGT
Consensus    ACATGGATGA  C
```

CONSENSUS A    SEQ ID NO 3

```
GTTTAGGGATAGCCC    TCATCTCTTTGGTCA    GGTACTGGCCCAAGA    TCTAGGCCACTTCTC    60
V - G - P          S S L W S          G T G P R          S R P L L
 F R D S P          H L F G Q          V L A Q D          L G H F S
  L G I A L          I S L V R          Y W P K I          - A T S Q

AGGTCCAGGCACTCT    GTTCCTTCAG                                              85
R S R H S          V P S
 G P G T L          F L Q
  V Q A L C          S F
```

CONSENSUS B    SEQ ID NO 4

```
GTTCAGGGATAGCCC    CCATCTATTTGGCCA    GGCACTAGCTCAATA    CTTGAGCCAGTTCTC    60
V Q G - P          P S I W P          G T S S I          L E P V L
 F R D S P          H L F G Q          A L A Q Y          L S Q F S
  S G I A P          I Y L A R          H - L N T          - A S S H

ATACCTGGACACTCT    TGTCCTTCGGT                                             86
I P G H S          C P S
 Y L D T L          V L R
  T W T L L          S F G
```

CONSENSUS C    SEQ ID NO 5

```
GTTCAGGGATAGCCC    CCATCTATTTGGCCA    GGCATTAGCCCAAGA    CTTGAGTCAATTCTC    60
V Q G - P          P S I W P          G I S P R          L E S I L
 F R D S P          H L F G Q          A L A Q D          L S Q F S
  S G I A P          I Y L A R          H - P K T          - V N S H

ATACCTGGACACTCT    TGTCCTTCAG                                              85
I P G H S          C P S
 Y L D T L          V L Q
  T W T L L          S F
```

CONSENSUS D    SEQ ID NO 6

```
GTTCAGGGATAGCTC    CCATCTATTTGGCCT    GGCATTAACCCGAGA    CTTAAGCCAGTTCTC    60
V Q G - L          P S I W P          G I N P R          L K P V L
 F R D S S          H L F G L          A L T R D          L S Q F S
  S G I A P          I Y L A W          H - P E T          - A S S H

ATACGTGGACACTCT    TGTCCTTTGG                                              85
I R G H S          C P L
 Y V D T L          V L W
  T W T L L          S F
```

FIG. 3

| | | | | | | |
|---|---|---|---|---|---|---|
| Consensus | TTGGATCCAG | TGYTGCCACA | GGGCGCTGAA | GCCTATCGCG | TGCAGTTGCC | 50 |
| Consensus | GGATGCCGCC | TATAGCCTCT | ACGTGGATGA | CCTSCTGAAG | CTTGAG | 96 |

SEQ ID NO 11

FIG. 6

| | | | | | |
|---|---|---|---|---|---|
| CAAGCCACCC | AAGAACTCTT | AAATTTCCTC | ACTACCTGTG | GCTACAAGGT | 50 |
| TTCCAAACCA | AAGGCTCAGC | TCTGCTCACA | GGAGATTAGA | TACTTAGGGT | 100 |
| TAAAATTATC | CAAAGGCACC | AGGGGCCTCA | GTGAGGAACG | TATCCAGCCT | 150 |
| ATACTGGGTT | ATCCTCATCC | CAAAACCCTA | AAGCAACTAA | GAGGGTTCCT | 200 |
| TAGCATGATC | AGGTTTCTGC | CGAAAACAAG | ATTCCCAGGT | ACAACCAAAA | 250 |
| TAGCCAGACC | ATTATATACA | CTAATTAAGG | AAACTCAGAA | AGCCAATACC | 300 |
| TATTTAGTAA | GATGGACACC | TAAACAGAAG | GCTTCCAGG | CCCTAAAGAA | 350 |
| GGCCCTAACC | CAAGCCCCAG | TGTTCAGCTT | GCCAACAGGG | CAAGATTTTT | 400 |
| CTTTATATGG | CACAGAAAAA | ACAGGAATCG | CTCTAGGAGT | CCTTACACAG | 450 |
| GTCCGAGGGA | TGAGCTTGCA | ACCCGTGGCA | TACCTGAATA | AGGAAATTGA | 500 |
| TGTAGTGGCA | AAGGGTTGGC | CTCATNGTTT | ATGGGTAATG | GNGGCAGTAG | 550 |
| CAGTCTNAGT | ATCTGAAGCA | GTTAAAATAA | TACAGGGAAG | AGATCTTNCT | 600 |
| GTGTGGACAT | CTCATGATGT | GAACGGCATA | CTCACTGCTA | AAGGAGACTT | 650 |
| GTGGTTGTCA | GACAACCATT | TACTTAANTA | TCAGGCTCTA | TTACTTGAAG | 700 |
| AGCCAGTGCT | GNGACTGCGC | ACTTGTGCAA | CTCTTAAACC | C | 741 |

SEQ ID NO 9 (PSJ 17)

FIG. 7

```
TCAGGGATAGCCCCCATCTATTTGGCCAGGCATTAGCCCAAGACTTGAGTC
AATTCTCATACCTGGACACTCTTGTCCTTCAGTACATGGATGATTTACTTT
TAGTCGCCCGTTCAGAAACCTTGTGCCATCAAGCCACCCAAGAACTCTTAA
CTTTCCTCACTACCTGTGGCTACAAGGTTTCCAAACCAAAGGCTCGGCTCT
GCTCACAGGAGATTAGATACTNAGGGCTAAAATTATCCAAAGGCACCAGG
GCCCTCAGTGAGGAACGTATCCAGCCTATACTGGCTTATCCTCATCCCAAA
ACCCTAAAGCAACTAAGAGGGTTCCTTGGCATAACAGGTTTCTGCCGAAA
ACAGATTCCCAGGTACASCCCAATAGCCAGACCATTATATACACTAATTA
NGGAAACTCAGAAAGCCAATACCTATTTAGTAAGATGGACACCTACAGAA
GTGGCTTTCCAGGCCCTAAGAAGGCCCTAACCCAAGCCCCAGTGTTCAGC
TTGCCAACAGGGCAAGATTTTTCTTTATATGCCACAGAAAAAACAGGAAT
AGCTCTAGGAGTCCTTACGCAGGTCTCAGGGATGAGCTTGCAACCCGTGGT
ATACCTGAGTAAGGAAATTGATGTAGTGGCAAAGGGTT
```

SEQ ID NO 8 (M003-P004)

FIG. 8

```
     10              20              30              40              50              60              70
     *               *               *               *               *               *               *
CCC TTT GCC ACT ACA TCA ATT TTA GGA GTA AGG AAA CCC AAC GGA CAG TGG AGG TTA GTG CAA GAA CTC AGG
 P   F   A   T   T   S   I   L   G   V   R   K   P   N   G   Q   W   R   L   V   Q   E   L   R>
                                         TRANSLATION OF F11-1 (A)

80              90             100             110             120             130             140
     *               *               *               *               *               *               *
ATT ATC AAT GAG GCT GTT CCT CTA TAC CCA GCT GTT CCT AAC CCT TAT ACA GTG CTT TCC CAA ATA CCA
 I   I   N   E   A   V   P   L   Y   P   A   V   P   N   P   Y   T   V   L   S   Q   I   P>
                                         TRANSLATION OF F11-1 (A)

150             160             170             180             190             200             210
     *               *               *               *               *               *               *
GAG GAA GCA GAG TGG TTT ACA GTC CTG GAC CTT AAG GAT GCC TTT TGC ATC CCT GTA CGT CCT GAC TCT
 E   E   A   E   W   F   T   V   L   D   L   K   D   A   F   C   I   P   V   R   P   D   S>
                                         TRANSLATION OF F11-1 (A)

220             230             240             250             260             270             280
     *               *               *               *               *               *               *
CAA TTC TTG TTT GCC TTT GAA GAT CCT TTG AAC CCA ACG TCT CAA CTC ACC TGG ACT GTT TTA CCC CAA GGG
 Q   F   L   F   A   F   E   D   P   L   N   P   T   S   Q   L   T   W   T   V   L   P   Q   G>
                                         TRANSLATION OF F11-1 (A)

290
     *
TTC AAG GGA
 F   K   G>
```

SEQ ID NO 2 (F11-1)

FIG. 9a

```
        10          20          30          40          50          60          70
         *           *           *           *           *           *           *
CCC TTT GCC ACT ACA TCA ATT TTA GGA GTA AGG AAA CCC AAC GGA CAG TGG AGG TTA GTG CAA GAA CTC AGG
 P   F   A   T   T   S   I   L   G   V   R   K   P   N   G   Q   W   R   L   V   Q   E   L   R>
___a___a___a___a___a___a___a___TRANSLATION OF MSRV-1 POL *  (A)___a___a___a___a___a___a___a__>
        80          90         100         110         120         130         140
         *           *           *           *           *           *           *
ATT ATC AAT GAG GCT GTT GTT CCT CTA TAC CCA GCT GTA CCT AAC CCT TAT ACA GTG CTT TCC CAA ATA CCA
 I   I   N   E   A   V   V   P   L   Y   P   A   V   P   N   P   Y   T   V   L   S   Q   I   P>
___a___a___a___a___a___a___a___TRANSLATION OF MSRV-1 POL *  (A)___a___a___a___a___a___a___a__>
       150         160         170    A    180         190         200         210
         *           *           *           *           *           *           *
GAG GAA GCA GAG TGG TTT ACA GTC CTG GAC CTT AAG GAT GCC TTT TTC TGC ATC CCT GTA CGT CCT GAC TCT
 E   E   A   E   W   F   T   V   L   D   L   K   D   A   F   F   C   I   P   V   R   P   D   S>
___a___a___a___a___a___a___a___TRANSLATION OF MSRV-1 POL *  (A)___a___a___a___a___a___a___a__>
       220         230         240         250         260         270         280
         *           *           *           *           *           *           *
CAA TTC TTG TTT GCC TTT GAA GAT CCT TTG AAC CCA ACG TCT CAA CTC ACC TGG ACT GTT TTA CCC CAA GGG
 Q   F   L   F   A   F   E   D   P   L   N   P   T   S   Q   L   T   W   T   V   L   P   Q   G>
___a___a___a___a___a___a___a___TRANSLATION OF MSRV-1 POL *  (A)___a___a___a___a___a___a___a__>
       290         300         310         320         330    B    340         350         360
         *           *           *           *           *           *           *
TTC AGG GAT AGC CCC CAT CTA TTT GGC CAG GCA TTA GCC CAA GAC TTG AGT CAA TTC TCA TAC CTG GAC ACT
 F   R   D   S   P   H   L   F   G   Q   A   L   A   Q   D   L   S   Q   F   S   Y   L   D   T>
___a___a___a___a___a___a___a___TRANSLATION OF MSRV-1 POL *  (A)___a___a___a___a___a___a___a__>
       370         380         390         400         410         420         430
         *           *           *           *           *           *           *
CTT GTC CTT CAG TAC ATG GAT GAT TTA CTT TTA GTC GCC CGT TCA GAA ACC TTG TGC CAT CAA GCC ACC CAA
 L   V   L   Q   Y   M   D   D   L   L   L   V   A   R   S   E   T   L   C   H   Q   A   T   Q>
___a___a___a___a___a___a___a___TRANSLATION OF MSRV-1 POL *  (A)___a___a___a___a___a___a___a__>
       440         450         460         470         480         490         500
         *           *           *           *           *           *           *
GAA CTC TTA ACT TTC CTC ACT ACC TGT GGC TAC AAG GTT TCC AAA CCA AAG GCT CGG CTC TGC TCA CAG GAG
 E   L   L   T   F   L   T   T   C   G   Y   K   V   S   K   P   K   A   R   L   C   S   Q   E>
___a___a___a___a___a___a___a___TRANSLATION OF MSRV-1 POL *  (A)___a___a___a___a___a___a___a__>
       510         520         530         540         550         560         570
         *           *           *           *           *           *           *
ATT AGA TAC TNA GGG CTA AAA TTA TCC AAA GGC ACC AGG GCC CTC AGT GAG GAA CGT ATC CAG CCT ATA CTG
 I   R   Y   X   G   L   K   L   S   K   G   T   R   A   L   S   E   E   R   I   Q   P   I   L>
___a___a___a___a___a___a___a___TRANSLATION OF MSRV-1 POL *  (A)___a___a___a___a___a___a___a__>
       580         590         600         610         620         630         640
         *           *           *           *           *           *           *
GCT TAT CCT CAT CCC AAA ACC CTA AAG CAA CTA AGA GGG TTC CTT GGC ATA ACA GGT TTC TGC CGA AAA CAG
 A   Y   P   H   P   K   T   L   K   Q   L   R   G   F   L   G   I   T   G   F   C   R   K   Q>
___a___a___a___a___a___a___a___TRANSLATION OF MSRV-1 POL *  (A)___a___a___a___a___a___a___a__>
       650         660         670         680         690         700         710         720
         *           *           *           *           *           *           *           *
ATT CCC AGG TAC ASC CCA ATA GCC AGA CCA TTA TAT ACA CTA ATT ANG GAA ACT CAG AAA GCC AAT ACC TAT
 I   P   R   Y   X   P   I   A   R   P   L   Y   T   L   I   X   E   T   Q   K   A   N   T   Y>
___a___a___a___a___a___a___a___TRANSLATION OF MSRV-1 POL *  (A)___a___a___a___a___a___a___a__>
       730         740         750         760         770         780         790
         *           *           *           *           *           *           *
TTA GTA AGA TGG ACA CCT ACA GAA GTG GCT TTC CAG GCC CTA AAG AAG GCC CTA ACC CAA GCC CCA GTG TTC
 L   V   R   W   T   P   T   E   V   A   F   Q   A   L   K   K   A   L   T   Q   A   P   V   F>
___a___a___a___a___a___a___a___TRANSLATION OF MSRV-1 POL *  (A)___a___a___a___a___a___a___a__>
       800         810         820         830         840         850         860
         *           *           *           *           *           *           *
AGC TTG CCA ACA GGG CAA GAT TTT TCT TTA TAT GCC ACA GAA AAA ACA GGA ATA GCT CTA GGA GTC CTT ACG
 S   L   P   T   G   Q   D   F   S   L   Y   A   T   E   K   T   G   I   A   L   G   V   L   T>
___a___a___a___a___a___a___a___TRANSLATION OF MSRV-1 POL *  (A)___a___a___a___a___a___a___a__>
       870         880         890         900         910         920         930
         *           *           *           *           *           *           *
CAG GTC TCA GGG ATG AGC TTG CAA CCC GTG GTA TAC CTG AGT AAG GAA ATT GAT GTA GTG GCA AAG GGT TGG
 Q   V   S   G   M   S   L   Q   P   V   V   Y   L   S   K   E   I   D   V   V   A   K   G   W>
___a___a___a___a___a___a___a___TRANSLATION OF MSRV-1 POL *  (A)___a___a___a___a___a___a___a__>
       940         950         960         970         980         990        1000
         *           *           *           *           *           *           *
CCT CAT NGT TTA TGG GTA ATG GNG GCA GTA GCA GTC TNA GTA TCT GAA GCA GTT AAA ATA ATA CAG GGA AGA
 P   H   X   L   W   V   M   X   A   V   A   V   X   V   S   E   A   V   K   I   I   Q   G   R>
___a___a___a___a___a___a___a___TRANSLATION OF MSRV-1 POL *  (A)___a___a___a___a___a___a___a__>
1010        1020        1030        1040        1050        1060        1070        1080
   *           *           *           *           *           *           *           *
GAT CTT NCT GTG TGG ACA TCT CAT GAT GTG AAC GGC ATA CTC ACT GCT AAA GGA GAC TTG TGG TTG TCA GAC
 D   L   X   V   W   T   S   H   D   V   N   G   I   L   T   A   K   G   D   L   W   L   S   D>
___a___a___a___a___a___a___a___TRANSLATION OF MSRV-1 POL *  (A)___a___a___a___a___a___a___a__>
```

FIG. 9b

```
         1090        1100        1110        1120        1130        1140        1150
           *           *           *           *           *           *           *
AAC CAT TTA CTT AAN TAT CAG GCT CTA TTA CTT GAA GAG CCA GTG CTG NGA CTG CGC ACT TGT GCA ACT CTT
 N   H   L   L   X   Y   Q   A   L   L   L   E   E   P   V   L   X   L   R   T   C   A   T   L>
___a___a___a___a___a___a___a___TRANSLATION OF MSRV-1 POL * (A)___a___a___a___a___a___a___a__>
AAA CCC
 K   P>
___a___>
```

SEQ ID NO 1 (MSRV-1 pol*)

FIG. 13

```
GTGCTGATTGGTGTATTTACAATCCTTTATCTAATCCGAAATGCCCATGTTG
CAATATGGAAAGAAAGGGAGTTCCTAACCTCTGGGGGAACCCCCATTAAA
TACCACAAGTAAATCATGGAGTTATTGCACACAGTGCAAAAACTCAAGGA
GGTGGAAGTCTTACACTGCCAAAGCCATCAGAAAAGGGAAGAGGGGAGAA
GAGCAGCATAAGTGGCTACAGAGGCAAGGAAAGACTAGCAGAAAGGAAA
GAGAGAAAGAGACAGAAAGTCAGAGAGAGAGAGAGGAAGAGACAGAGCA
CAAAGAGGGAGTCAGAGAGAGAGAGAGACAGAGAGTCAGAGAGAAGGAA
AGAGAGAGGAAGAGACAAAGAATGAATCAAACAGAGAGACAGAAAGT
CAGAGAGAGAGAGAGAGGAAGAGACAGAGAAAAGAGGGAGTCAGAA
AAAGAGAGACCAAAGAAGAAGTCCAAAGAGAAAGAAAGAGAGATGGAAG
TAGTAAAGGAAAAACAGTGTACCCTATTCCTTTAAAAGCCGGGGTAAATTT
AAAACCTATAATTGATAACTGAAGGTCTTCTCTGTAACCCTGTAACACTCC
AATACCACCTTGTTGTCAAGTGTAAACAAGGGCGTAGCCCAAAAGCACTG
AGGCCACTAACAACCCATAGCCTTCCTATCAAAATTCCTTAACCCAGCAGG
TTTCCTAACAGGGGATCTAAATCTTAATTAATTACCATACAATGGTCCAAC
CAGACTTAGGAGGAATTCCCTTCAGGACGGGAAGATAGATGCTTCCTCCCA
GGCGATTAAGGGAGAAAGACACAATGGGTATTCAGTAAGTGCCAAGGGA
ACACTTGTAGAAGCAAAGTTAGGAAAATTGCCAAATAATTGGTTTGCTCAA
GAGTTGTTTGCACTCAGCCAAACCTTGAAGTACTTGCAGAATCAGAAAGGA
GCCATCTATACCAATTCTAAGTTAATATGGACTGAAGGAGGTTTTATTAAT
ACCAAAGAGAAATTAAAATCCCAAACTTATAAGGTTTTCAACCAAAGTAA
AGTTTGCTAAAAGTTAACAGCGTAACATGTATTATCCTACTACCACACACT
CTCAAAGGATTTCTCAGACAGTTTGCAAGAAATAATGATATCTATCCTTAC
TCTACAATCCCAAATAGACTCTTTGGCAGCAGTGACTCTCCAAAACCGTCA
AGGCCTAGACCTCCTCACTGCTGAGAAAGGAGGACTCTGCACCTTCTTAAG
GGAAGAGTGTTGTCTTTACACTAACCAGTCAGGGATAGTATGAGATGCTGC
CCGGCATTTACAGAAAAGGCTTCTGAAATCAGACAACGCCTTTCAAATTC
CTATACCAACCTCTGGAGTTGGGCAACATGGTTTCTTCCCTTTCTATGTCCC
ATGGCTGCCATCTTGCTATTACTCGCCTTTGGGCCCTGTATTTTAACCTCC
TTGTCAAATTTGTTTCTTCTAGGATCGAGGCCATCAAGCTACAGATGGTCTT
ACAAATGGAACCCCAAATGAGCTCAACTATCAACTTCTACTGAGGACCCCT
AGACCAACCCCCTGGCCCTTTCACTGGCCTAAAGAGTTCCCCTCTGGAGGA
CACTACCACTGCAGGGCCCCATCTTTGCCCCTATCCAGAAGGAAGTAGCTA
GAGCAGTCATTGCCCAATTCCAAGAGCAGCTGGGGTGTCCCGTTTAGAGT
GGGGATTGAGAGGTGAAGCCAGCTGGACTTCTGGGTCGGGTGGGGACTTG
GAGAACTTTTGTGTCTAGCTAAAGGATTGTAAATGCAACAATCAGTGCTCT
GTGTCTAGCTAAAGGATTGTAAATACACCAATCAGCAC
```

SEQ ID NO 46 (FBd3)

FIG. 15

```
GGCTGCTAAAGGAGACTTGTGGTTGTCAGACAATCGCCTACTTAGGTACCA
GGCCTTATTACTTGAGGGACTGGTGCTTCAGATGCGCACTTGTGCAGCTCT
TAACCCAAACTTATGCTGCCCAGAAGGATCTTTTAGAGGTCCCCTTAGCCA
ACCCTGACCTCAACCTATATATATACTGATGGAAGTTCGTTTGTAGAAAAG
GGATTACAAAGGGNAGGATATNCCATAGGTTAGTGATAAAGCAGTACTTG
AAAGTAAGCCTCTTCCCCCCAGGGACCAGCGCCCCGTTAGCAGAACTAGT
GGCACTGACCCCGAGCCTTAGAACTTGGAAAGGGAGGAGGATAAATGTGT
ATACAGATAGCAAGTATGCTTATCTAATCCGAAATGCCCATGTTG
```

SEQ ID NO 51 (t pol)

FIG. 16

```
TCAGGGATAGCCCCCATCTATTTGGTCAGGCACTGGCCCAAGATCTAGGGA
CATGCCACTTTTAAGAGCCATTTCTCAAGTCCAGGTACTCTGGTCCTTCGGT
ATGTGGATGATTTACTTTTGGCTACCAGTTCAGTAGCCTCATGCCAGCAGG
CTACTCTAGATCTCTTGAACTTTCTAGCTAATCAAGGGTACAAGGCATCTA
GGTTGAAGGCCCAGCTTTGCCTACAGCAGGTCAAATATCTAGGCCTAATCT
TAGCCAGAGGGACCAGGGCACTCAGCAAGGAACAAATACAGCCTATACTG
GCTTATCCTCACCCTAAGACATTAAAACAGTTGCGGGGGTTCCTTGGAATC
ACTGGCTTTTGGTGACTATGGATTCCCAGATACAGCAAGATTGGCAGGCC
CCTCTATACTGTAATCAAGGAGACTCACGAGGGCAAGTACTCATCTAGTAG
AATGGGAACTAGGGACAGAAACAGCCTTCAAAACCTTAAAGCAGGCCCTA
GTACAATCTCCAGCTTTAAGCCTTCCCACAGGACAAAACTTCTCTTTATAC
ATCACAGAGAGGGCAGAGATAGCTCTTGGTGTCCTTATTCAGACTCATGGG
ACTACCCCACAACCAGTGGCACACCTAAGTAAGGAAATTGATGTAGTAGC
AAAAGGCTGGCCTCACTGTTTATGGGTAGCTGTGGTGGTGGCTGTCTTAGT
GTCAGAAGCTATCAAAATAATACAAGGAAAGGATCTCACTGTCTGGACTA
CTCATGATGTAATGGCATACTAGGTGCCAAAAGAAGTTTATGGGTATCAGA
CAACCACCTGCTTAGATACCAGGGACTACTCCTGGAGGATTGGGCTTCAAG
TGCGTTTTTTGTGGCCTCAACCCTGCCACTTTTCCTCCAGAGGATGGAGAG
CCGCTTGAGCATGCTTGCCAACAGGTTGTAGGCCAGAATTATTCCACCCGA
GATGATCTCTTAGAGTACCCTTAGCTAATCCTGACCTTAACCTATATACCA
ATGGAAGTTCATTTGTGGAAAACGGGATATGAAGGGCAGGTTATGTCATAG
TTAGTGATGTAATCATACTTGCAAGTAAGCCTCTTACCCCAGGGGCCAGCA
CTCAGTTAGCAGAACTAGTCACACTTACCTTAACCTTAGAACTGGGAAAGG
GAAAAGAATAAATATGTATACAGATAGTAAGTATGCTTATCTAATCCTAC
ATGCCCATGCTGCAATATGGAAGGAAAGGGAGTTCCTAACCCCTGGGGGA
ACCCCCATTAAATACCACAAGGYAAATCATGGAGTTATTGCACGCAGTGC
AAAAACTCAAGGAGGTGGCAGTCTTACACTGCCGAAGCYATCAAAAAGGG
GAAGGAGAGGGGAGAACAGCAGCATAAGTGGTTGGCAGAGGCAGTGAAA
GACCAGCAGAGAGAAGGAGAGAGACAACGTCAACGACAGAAGGAAAGAA
GAGGAGGAGACAGAGAGGAAGAGACAGAGAGACAGTTAGTCCAAGAGAG
AGACAGAGAGAGGAAGAGACAGACAGAAAGTCCAAGAGAGAAGGAAAGA
GAGGAAGAGACCAAGGAGTCCNAGAGAGAGAAAGAGATAGAAGTAGTAA
AGAAAAAACATTGTACCCTATTCCTTTAAAAGCCGGGGTATATTTAAAACC
TATAATTGATAATTGAGTTCTTGCACCCTCCTCCAGGGGATYGCTGGGAGG
AAACCCTCAACCGATATGTGAAATTGTGGGTCGTCCCTATGTCTCAATTA
CCAGCCAATACCCCCTTGTTTTTAGTGTGAACGAGGGTGTAGAGCGCAGAC
AGGGAGACCTCTGACAATCCATACCCTTCCTATCCAAAATCCTTAACCCAG
CAGGTTTTCTAAAAGGGGATCTAAATCTTAATTAATTACCATACAAAGGTC
AAACCAGATCTAGGAGGAACTTCCTTCAGGACAGGATGATAGATGGTTCCT
CCCAGGCGATTAAAGAAAATAAAAAGACACATGGGCAGCCAGTAAGTGAT
AAGGGAACACTAGTAGAAGCAGTTAGGAGAAGTTGCCTAATAATTGGTCT
ACTCCAAATGTGTGAGTTGTTCGCACTCAGCCCAAATCTTAAAGTACTTAC
AGAATTAGGGAGGAGCCATTTACACCAATTCTAAGTTAATATGGACTGGAT
GAGGTTTTATTAATAGCGAAGGAGAATTAAATCCTAAACTNACAAGGTTTT
CAACTAAAGTAAATTTTACTAAAAGCTAACAGTGTAACATGCATTATCCTA
CTACAACACACTCTCANAGGATTCCTCAGACAGTTTACAAGAAATAACAA
AATCTATCTGGTAAGGATAGTAACTACAATCCCAAATACATTCTTTGGCAG
CAGTGACTCTC
```

SEQ ID NO 52 (JLBc1)

FIG. 17

```
TCAGGGATAGCCCCCATCTATTTGATCAGGCACTAGCCCAAGATCTAGGCC
ACTTCTGAAGTCCAGGCATTCTAGTCCTTCAGTATGTGGATGATTTACTTTT
GGCTACCAGTTTGGAAGCCTCATGCCAGCAGGCTACTTGAGATCTCTTGAA
CTTTCTAGCTAATCAAGGGTGTATGGCATCTAAATTGAAAGTCCAGCTCTG
CCTACAACAAGTCAAATATCTAGGCCTAATCTTAGATAGAAGAACCAGGG
CCCTCAGCAAGGAATGAATAAAGCCTATGCTGGCTTATCGGCACCCTAAGA
CATTAAAACAATTGTGGGGGTTCCTTGGAATCACTGGCTTTTGCCGACTAT
GGATCCCTGGATAGAGTGAGATAGCCAGGCCCCCTCTATTACTCTTATCAA
GGAGACCCAGAGGGCAAATACTTATCTAGTATTATGGGNACCAGAGGCAG
AAAAAGCCTTCCAAACCTTAAAGGAGACCCTAGTACAAGCTCCAGCTTTAA
GCCTTCCCACAGGACAAANCTTCTCTTTATATGTCACAGAGAGAGCAGGAA
TAGCTCCTGGAGTCCTTACTCAGACTTTTGGACGACCCCACGGCCAGTGGC
RTACCTAAGTAAGGAAATTGATGTAGTAGCAAAAGGCTGGCCTCACTGTTT
ATGGGTAGTTGCGGCTGTGGCAGTCTTACTGTCAAAGGCTATCAAAATAAT
ACAAGGAAAGGATTTCACTATCTGGACTACTCATGAGGAAAATGGCATATT
AGGTGCCAAAGGAAGTTTTTGGCTATCAGACAACCACCTGCTCAGATTCCA
GGCACTACTGATTGAGAGACCAGTGCTTTAAATATGTATGTGTGTGTGG
CCCTCAACCCTGCCACTGTTCTCCCAGAAGATGGAGAACCAATGAAGCATT
ACTGTCAACAAATTAGAGTCCAGAGTTATGCTGCCTGAGAGGATCTCTTAG
AAGTCCCCTTAGCTAATCCTGACCTTAACCTATATGCTGATGGAAGTTCAC
TTGTGGAGAATGGGATACGAAAGCACATTATGCCATAGTTAGTGAGGTA
ACAGTACTTGAAAGTAAGCCTATTCCCCCATGGACCAGAGCCCAGTTAGCA
GAACTAGTGGCACTTACCCAAGCCTTAGAACTAGGAAAGGGAAAAATAAT
AAATGTGTATACAGATAGCAAGTATGCTTATCTAATCCTACATGCCCATGC
TGCAGTATGGAAAGAAAGGGAGTTCCTAACCTCTGGGGGAACCCCCATTA
AATACCACAAGGCAAATCATGGAGTTATTGCATGTAGTGCAAAACCTCAA
GTAGGTGGCAGTTTTACACTGCCTGAAGCTATGGGGAAGGAGAGAGGAGA
ACAGCAGCATAAGTGGCTAGCAGAGGCAGCGAAAGACTAGCAGAGAGGA
GAGGTAGGGGAAAGACAGAAAGTCAAAGAAAAGAAGTCAAAGACAGACA
GAGAAAGAGACAGAGGGAGCCAGAGAGAAAGAAAAGAGAGAACGAAAGA
GACAGAATGTCAAAGAACAGAAGAGAGAGGCAGCGCCAGAAGAGTTAAG
AAAGTGAGAAAGAGAGATGGAAATAGTAAAGAAAAAACAGTGTACCCTAT
TCCTTTAAAAGCCAGGGTAAATTTAAAACGTATAATTTTATAATTGGAAGG
TCTTCTCCATAACCCTATAACATTAAAATACCACCTTGTTGTCAGTGTAAAC
AAGAGCATAGCCCAAAAGCACTGAGGCCACTGACAACCCATAGCCTTCCT
ATCAAAATCCTTAACTCTGCAGGTTTCCTAACAGGGGATCTAAATCTCAA
CTAATCACCATACAATGGTCCGACCAGACCTAGGAGCGACTCCCCTCAGG
ACAGAAGGATGGATGGTTCCTCCCAGGCCATTAAGGGAAAGAGACACAAT
GGGTATTCAGTAAGTGATAAGGGAACTCTTGTAGAAGCAGTTAGGAAGATT
GCCTAATATTTGGTCTGCTCAAATGTGCCAGCTGTTTGCACTCAGCTAAAC
CTTAAATTACTTACAGAATTAGGAAGGAGCCATCTATACCAATTCTGAGTT
AATATGAGCTGAACAAGTTCTTATTAATAGCAAAGAATCATTGAAATCTCA
AACTTGCAAAGTTTTCAACAAAAGTAAAGTTTGCTGAAAGTTAGCAGTGTA
ACATGTATTATCCTAACTTCTAATCTTGTGGAAATCAGACCCTATCAGTGC
CCCTCAAAGCTGAAGTCCATCAGCATATGGCCATACAACTAATACCCCTAT
TTATAGGGTTAGGAATGGCCACTGCTACAGGAATGGGAGTAACAGGTTTAT
CTACTTCATTATCCTATTACCACACACTCTTAAAGGATTTCTCAGACAGTTT
ACAAGAAATAACAAAATCTATCCTTACTCTNTARTCCCAAATAGRTTCTTT
GGCAGCAGTGACTCTC
```

SEQ ID NO 53 (JLBc2)

FIG. 23

```
   1  TTCCTGAGTT  CTTGCACTAA  CCTCAAATGA  GAGAAGTGCC  GCCATAACTG  CAACCCAAGA
  61  GTTTGGCGAT  CCCTGGTATC  TCAGTCAGGT  CAATGACAGG  ATGACAACAG  AGGAAAGATA
 121  ATGATTCCCC  ACAGGCCAGC  AGGCAGTTCC  CAGTGTAGAC  CCTCATTAGG  ACACAGAATC
 181  AGAACATGGA  GATTGGTGCC  GCAGACATTT  GCTAACTTGC  GTGCTAGAAG  GACTAAGGAA
 241  AACTAGGAAG  ATATGAATTA  TTCAATGATG  TCCACTATAA  CACAGGGGAA  AGGAAGAAAA
 301  TCCTACTGCC  TTTCTGGAGA  GACTAAGGGA  GGCATTGAGG  AAGCATACCA  GGCAAGTGGA
 361  CATTGGAGGC  TCTGGAAAAG  GGAAAAGTTG  GGAAAAGTAT  ATGTCTAATA  GGGCTTGCTT
 421  CCAGTGTGGT  CTACAAGGAC  ACTTTAAAAA  AGATTGTCCA  ATAGAAATAA  GCCACCACCT
 481  CGTCCATGCC  CCTTATGTCA  AGGGAATCAC  TGGAAGGCCC  ACTGCCCCAG  GGGATGAAGG
 541  TCCTCTGAGT  CAGAAGCCAC  TAACCAGATG  ATCCAGCAGC  AGGACTGAGG  GTGCCCGGGG
 601  CAAGCGCCAG  CCCATGCCAT  CACCCTCACA  GAGCCCCAGG  TATGCTTGAC  CATTGAGGGT
 661  CAGAAGGGTA  CTGTCTCCTG  GACACTGGCG  GGCCTTCTCA  GTCTTACTTT  CCTGTCCTGG
 721  ACAACTGTCC  TCCAGATCTG  TCACTGTCCG  AGGGGTCCTA  GGACAGCCAG  TCACTAGATA
 781  CTTCTCCCAG  CCACTAAGTT  GTGACTGGGG  AACTTTACTC  TTCCACATGC  TTTTCTAATT
 841  ATGCCTGAAA  GCCCCACTCT  CTTGTTAGGG  GAGAGACATT  CTAGCAAAAG  CAGGGGCCAT
 901  TATACATGTG  AATATAGGAG  AAGGAACAAC  TGTTTGTTGT  CCCCTGCTTG  AGGAAGGAAT
 961  TAATCCTGAA  GTCCGGGCAA  CAGAAGGACA  ATATGGACAA  GCAAAGAATG  CCCGTCCTGT
1021  TCAAGTTAAA  CTAAAGGATT  CCACCTCCTT  TCCCTACCAA  AGGCAGTACC  CCCTCAGACC
1081  CGAGACCCAA  CAAGAACTCC  AAAAGATTGT  AAAGGACCTA  AAAGCCCAAG  GCCTAGTAAA
1141  ACCAAGCAAT  AGCCCTTGCA  AGACTCCAAT  TTTAGGAGTA  AGGAAACCCA  ACGGAC
```

*SEQ ID NO 56* (GM3)

FIG. 27a

```
ATG ATC CAG CAG CAG GAC NGA GGG TGC CCG GGG CAA GCG CCA GCC CAT GCC ATC ACC CTC ACA GAG CCC CAG GTA TGC TTG ACC ATT GAG  90
 M   I   Q   Q   Q   D   X   G   C   P   G   Q   A   P   A   H   A   I   T   L   T   E   P   Q   V   C   L   T   I   E

GGT CAG AAG GGT NAC TGT CTC CTG GAC ACT GGC GGN GCC TTC TCA GTC TTA CTT TCC TGT CCT GGA CAA CTG TCC TCC AGA TCT GTC ACT 180
 G   Q   K   G   X   C   L   L   D   T   G   G   A   F   S   V   L   L   S   C   P   G   Q   L   S   S   R   S   V   T

GTC CGA GGG GTC CTA GGA CAG CCA GTC ACT AGA TAC TTC TCC CAG CCA CTA AGT TGT GAC TGG GGA ACT TTA CTC TTC CCA CAT GCT TTT 270
 V   R   G   V   L   G   Q   P   V   T   R   Y   F   S   Q   P   L   S   C   D   W   G   T   L   L   F   P   H   A   F

CTA ATT ATG CCT GAA AGC CCC ACT CTC TTG TTG GGG AGA GAC ATT CTA GCA AAA GCA GGG GCC ATT ATA CAT GTG AAT ATA GGA GAA GGA 360
 L   I   M   P   E   S   P   T   L   L   L   G   R   D   I   L   A   K   A   G   A   I   I   H   V   N   I   G   E   G

ACA ACT GTT TGT TGT CCC CTG CTT GAG GAA GGA ATT AAT CCT GAA GTC CGG GCA ACA GAA GGA CAA TAT GGA CAA GCA AAG AAT GCC CGT 450
 T   T   V   C   C   P   L   L   E   E   G   I   N   P   E   V   R   A   T   E   G   Q   Y   G   Q   A   K   N   A   R

CCT GTT CAA GTT AAA CTA AAG GAT TCC ACC TCC TTT CCC TAC CAA AGG CAG TAC CCC CTC AGA CCC GAG ACC CAA CAA GAA CTC CAA AAG 540
 P   V   Q   V   K   L   K   D   S   T   S   F   P   Y   Q   R   Q   Y   P   L   R   P   E   T   Q   Q   E   L   Q   K

ATT GTA AAG GAC CTA AAA GCC CAA GGC CTA GTA AAA CCA AGC AAT AGC CCT TGC AAG ACT CCA ATT TTA GGA GTA AGG AAA CCC AAC GGA 630
 I   V   K   D   L   K   A   Q   G   L   V   K   P   S   N   S   P   C   K   T   P   I   L   G   V   R   K   P   N   G

CAG TGG AGG TTA GTG CAA GAA CTC AGG ATT ATC AAT GAG GCT GTT GTT CCT CTA TAC CCA GCT GTA CCT AAC CCT TAT ACA GTG CTT TCC 720
 Q   W   R   L   V   Q   E   L   R   I   I   N   E   A   V   V   P   L   Y   P   A   V   P   N   P   Y   T   V   L   S

CAA ATA CCA GAG GAA GCA GAG TGG TTT ACA GTC CTG GAC CTT AAG GAT GCC TTT TTC TGC ATC CCT GTA CGT CCT GAC TCT CAA TTC TTG 810
 Q   I   P   E   E   A   E   W   F   T   V   L   D   L   K   D   A   F   F   C   I   P   V   R   P   D   S   Q   F   L

TTT GCC TTT GAA GAT CCT TTG AAC CCA ACG TCT CAA CTC ACC TGG ACT GTT TTA CCC CAA GGG TTC AGG GAT AGC CCC CAT CTA TTT GGC 900
 F   A   F   E   D   P   L   N   P   T   S   Q   L   T   W   T   V   L   P   Q   G   F   R   D   S   P   H   L   F   G

CAG GCA TTA GCC CAA GAC TTG AGT CAA TTC TCA TAC CTG GAC ACT CTT GTC CTT CAG TAC ATG GAT GAT TTA CTT TTA GTC GCC CGT TCA 990
 Q   A   L   A   Q   D   L   S   Q   F   S   Y   L   D   T   L   V   L   Q   Y   M   D   D   L   L   L   V   A   R   S

GAA ACC TTG TGC CAT CAA GCC ACC CAA GAA CTC TTA ACT TTC CTC ACT ACC TGT GGC TAC AAG GTT TCC AAA CCA AAG GCT CGG CTC TGC 1080
 E   T   L   C   H   Q   A   T   Q   E   L   L   T   F   L   T   T   C   G   Y   K   V   S   K   P   K   A   R   L   C
```

*SEQ ID NO 57* (POL)

FIG. 27b

SEQ ID NO 57 (POL)

FIG. 27c

```
CTC AAG GAG GTG GAA GTC TTA CAC TGC CAA AGC CAT CAG AAA AGG GAA GGA GAA GAG CAG CAT AAG TGG CTA CAG AGG CAA GGA AAG  2250
 L   K   E   V   E   V   L   H   C   Q   S   H   Q   K   R   E   G   E   E   Q   H   K   W   L   Q   R   Q   G   K

ACT AGC GAG AAG GAG AAA GAG ACA GAG GAG ACA GAG GAG CAT CAC AAA GAG GGA GTC AGG AGA GAG AGA GAG  2340
 T   S   E   K   E   K   E   T   E   E   T   E   E   H   H   K   E   G   V   R   R   E   R   E

AGA CAG AGA GTC AGA AGC AGT GGA AGA GAT AAA GAA TGA .  2391
 R   Q   R   V   R   S   S   G   R   D   K   E   *
```

*SEQ ID NO 57* (POL)

FIG. 28

GATGCCTTTTTCTGCATCCCTGTACGTCCTGACTCTCAATTCTTGTTTGCCTTTGAAG
ATCCTTTGAACCCAACGTCTCAACTCACCTGGACTGTTTTACCCCAAGGGTTCAGGGA
TAGCCCCATCTATTTGGCCAGGCATTAGCCCAAGATGCCTTTTGCATCCCTGTACGTG
ACTCTCAATTCTTGTTTGCCTTTGCCTTTGAAGATGCTTTGAACCCAACGTCTCAACT
CACCTGGACTGTTTTACGCCAAGGGTTCAGGGATAGCCCCCATCTATTTGGC
CAGGCATTAGCCCAA

SEQ ID NO 40

Asp-Ala-Phe-Phe-Cys-Ile-Pro-Val-Arg-Pro-Asp-Ser-Gln-Phe-
Leu-Phe-Ala-Phe-Glu-Asp-Pro-Leu-Asn-Pro-Thr-Ser-Gln-Leu-
Thr-Trp-Thr-Val-Leu-Pro-Gln-Gly-Phe-Arg-Asp-Ser-Pro-His-
Leu-Phe-Gly-Gln-Ala-Leu-Ala-Gln

SEQ ID NO 39 (POL2B)

FIG. 34

Cys-Ile-Pro-Val-Arg-Pro-Asp-Ser-Gln-Phe-Leu

*SEQ ID NO 41*

Val-Leu-Pro-Gln-Gly-Phe-Arg-Asp-Ser-Pro-His-Leu-Phe-Gly-
Gln-Ala-Leu-Ala

*SEQ ID NO 42*

Leu-Phe-Ala-Phe-Glu-Asp-Pro-Leu

*SEQ ID NO 43*

Phe-Ala-Phe-Glu-Asp-Pro-Leu-Asn

*SEQ ID NO 44*

FIG. 35

```
           10         20         30         40         50
       1234567890 1234567890 1234567890 1234567890 1234567890
       CTTCCCCAAC TAATAAGGAC CCCCCTTTCA ACCCAAACAG TCCAAAAGGA    50
        L  P  Q  L  I  R  T   P  L  S   T  Q  T  V  Q  K  D
       F  P  N    .  .  G  P  P  F  Q  P  K  Q    S  K  R  T
         S  P  T   N  K  D   P  P  F  N  P  N  S   P  K  G

CATAGACAAA GGAGTAAACA ATGAACCAAA GAGTGCCAAT ATTCCCTGGT   100
        I  D  K   G  V  N  N  E  P  K   S  A  N   I  P  W  L
       .  T  K    E  .  T   M  N  Q  R  V  P  I   F  P  G
         H  R  Q  R  S  K  Q  .  T  K   E  C  Q  Y  S  L  V

TATGCACCCT CCAAGCGGTG GGAGAAGAAT TCGGCCCAGC CAGAGTGCAT   150
        C  T  L   Q  A  V    G  E  E  F  G  P  A   R  V  H
       Y  A  P  S  K  R  W   E  K  N   S  A  Q  P  E  C  M
         M  H  P  P  S  G  G  R  R  I   R  P  S   Q  S  A  C

GTACCTTTTT CTCTCTCACA CTTGAAGCAA ATTAAAATAG ACNTAGGTNA   200
        V  P  F  S  L  S  H   L  K  Q   I  K  I  D  X  G  X
       Y  L  F    L  S  H  T  .  S  K   L  K  .   T  .  V  N
         T  F  F   S  L  T   L  E  A  N  .  N  R   X  R  X

ATTNTCAGAT AGCCCTGATG GYTATATTGA TGTTTTACAA GGATTAGGAC   250
        X  S  D   S  P  D  G   Y  I  D   V  L  Q   G  L  G  Q
       X  Q  I    A  L  M    X  I  L  M  F  Y  K  D  .  D
       I  X  R  .  P  .  W   L  Y  .    C  F  T  R  I  R  T

AATCCTTTGA TCTGACATGG AGAGATATAA TATTACTGCT AAATCAGACG   300
        S  F  D   L  T  W    R  D  I  I  L  L  L   N  Q  T
       N  P  L  I  .  H  G   E  I  .    Y  Y  C  .  I  R  R
         I  L  .   S  D  M  E  R  Y  N   I  T  A   K  S  D  A

CTAACCTCAA ATGAGAGAAG TGCTGCCATA ACTGGAGCCC GAGAGTTTGG   350
        L  T  S  N  E  R  S   A  A  I   T  G  A  R  E  F  G
       .  P  Q    M  R  E  V  L  P  .   L  E  P   E  S  L  A
         N  L  K   .  E  K   C  C  H  N  W  S  P   R  V  W

CAATCTCTGG TATCTCAGTC AGGTCAATGA TAGGATGACA ACGGAGGAAA   400
        N  L  W   Y  L  S  Q   V  N  D   R  M  T   T  E  E  R
       I  S  G    I  S  V    R  S  M  I  G  .  Q   R  R  K
       Q  S  L  V  S  Q  S   G  Q  .    .  D  D  N  G  G  K

GAGAACGATT CCCCACAGGG CAGCAGGCAG TTCCCAGTGT AGCTCCTCAT   450
        E  R  F   P  T  G    Q  Q  A  V  P  S  V   A  P  H
       E  N  D  S  P  Q  G   S  R  Q    F  P  V  .  L  L  I
         R  T  I   P  H  R  A  A  G  S   S  Q  C   S  S  S  L

TGGGACACAG AATCAGAACA TGGAGATTGG TGCCGCAGAC ATTTA        495
        W  D  T  E  S  E  H   G  D  W   C  R  R  H  L
       G  T  Q    N  Q  N  M  E  I  G   A  A  D   I
         G  H  R   I  R  T   W  R  L  V  P  Q  T   F
```

FIG. 36

```
         10          20          30          40          50
  1234567890  1234567890  1234567890  1234567890  1234567890
  CTTCCCCAAC  TAATAAGGAC  CCCCCTTTCA  ACCCAAACAG  TCCAAAAGGA      50
   L  P  Q  L    I  R  T     P  L  S     T  Q  T  V    Q  K  D

CATAGACAAA  GGAGTAAACA  ATGAACCAAA  GAGTGCCAAT  ATTCCCTGGT     100
   I  D  K     G  V  N  N    E  P  K     S  A  N    I  P  W  L

TATGCACCCT  CCAAGCGGTG  GGAGAAGAAT  TCGGCCCAGC  CAGAGTGCAT     150
   C  T  L     Q  A  V     G  E  E  F    G  P  A     R  V  H

GTACCTTTTT  CTCTCTCACA  CTTGAAGCAA  ATTAAAATAG  ACCTAGGTAA     200
   V  P  F  S    L  S  H     L  K  Q     I  K  I  D    L  G  K

ATTCTCAGAT  AGCCCTGATG  GYTATATTGA  TGTTTTACAA  GGATTAGGAC     250
   F  S  D     S  P  D  G    Y  I  D     V  L  Q     G  L  G  Q

AATCCTTTGA  TCTGACATGG  AGAGATATAA  TATTACTGCT  AAATCAGACG     300
   S  F  D     L  T  W     R  D  I  I    L  L  L     N  Q  T

CTAACCTCAA  ATGAGAGAAG  TGCTGCCATA  ACTGGAGCCC  GAGAGTTTGG     350
   L  T  S  N    E  R  S     A  A  I     T  G  A  R    E  F  G

CAATCTCTGG  TATCTCAGTC  AGGTCAATGA  TAGGATGACA  ACGGAGGAAA     400
   N  L  W     Y  L  S  Q    V  N  D     R  M  T     T  E  E  R

GAGAACGATT  CCCCACAGGG  CAGCAGGCAG  TTCCCAGTGT  AGCTCCTCAT     450
   E  R  F     P  T  G     Q  Q  A  V    P  S  V     A  P  H

TGGGACACAG  AATCAGAACA  TGGAGATTGG  TGCCGCAGAC  ATTTACAACT     500
   W  D  T  E    S  E  H     G  D  W     C  R  R  H    L  Q  L

TGCGTGCTAN  AAGGACTNAG  GAAAACTAGG  AAGACTANGA  ATTATTCAAN     550
   A  C  X     K  D  X  G    K  L  G     R  L  X     I  I  Q  X

GATGTCCACT  ANNACACAGG  GGAAAGGAAG  AAAATCCTAC  TGCCTTTCTG     600
   C  P  L     X  H  R     G  K  E  E    N  P  T     A  F  L

GAGAGACTAA  GGGAGGCATT  GAGGAAGCAT  ACCAGGCAAG  TGGACATTGG     650
   E  R  L  R    E  A  L     R  K  H     T  Q  V     D  I  G

AGGCTCTGGA  AAAGGGAAAA  GTTGGGCAAA  TTATATGCCT  AATAGGGCTT     700
   G  S  G     K  G  K  S    W  A  N     Y  M  P     N  R  A  C

GCTTCCAGTG  CAGTCTACAA  GGACGCTTTA  GAAAAGATTG  TCCAAGTAGA     750
   F  Q  C     S  L  Q     G  R  F  R    K  D  C     P  S  R

AATAAGCCGC  CCCTCGTCCA  TGCCCCTTAT  GTCAAGGGAA  TCACTGGAAG     800
   N  K  P  P    L  V  H     A  P  Y     V  K  G  I    T  G  R

GCCTACTGCC  CCAGGGGACG  AAGGTCCTCT  GAGTCAGAAG  CCACTAACCT     850
   P  T  A     P  G  D  E    G  P  L     S  Q  K     P  L  T  .

```
          10          20          30          40          50
      1234567890  1234567890  1234567890  1234567890  1234567890
      AAGGAAACTC  AGAAAGCCAA  TACCCATTTA  GTAAGATGGA  CACCAGAAGC    50
       K E T Q     K A N       T H L      V R W T     P E A
      R K L       R K P I      P I .      . D G     H Q K Q
     G N S       E S Q       Y P F S     K M D     T R S

AGAAGCAGCT  TTCCAGGCCC  TAAAGAAATC  CCTAACCCAA  GCCCCAGTGT   100
       E A A       F Q A L     K K S       L T Q      A P V L
      K Q L       S R P       . R N P     . P K      P Q C
     R S S F     P G P       K E I       P N P S    P S V

TAAGCTTGCC  AACGGGGCAA  GACTTTTCTT  TATATGTCAC  AGAAAAACAG   150
       S L P       T G Q       D F S L     Y V T      E K Q
      . A C Q     R G K       T F L      Y M S Q    K N R
     K L A       N G A R     L F F       I C H     R K T G

GAATAGCTCT  AGGAGTCCTT  ACACAGGTCC  AAGGGACAAG  CTTGCAACCT   200
       E . L .     E S L       H R S       K G Q A    C N L
      N S S       R S P Y     T G P       R D K      L A T C
     I A L       G V L       T Q V Q     G T S     L Q P

GTGGCATACC  TGAGTAAGGA  AACTGATGTA  NTGGCAAAGG  GTTGGCCTCA   250
       W H T       . V R K     L M X       W Q R      V G L I
      G I P       E . G       N . C X     G K G      L A S
     V A Y L     S K E       T D V       X A K G    W P H

TTGTTTACAG  GTAGGGCAGC  AGTAGCAGTC  TTAGTTTCTG  AAACAGTTAA   300
       V Y R       . G S       S S S L     S F .      N S .
      L F T G     R A A       V A V       L V S E    T V K
     C L Q       V G Q Q     . Q S       . F L     K Q L K

AATAATACAG  GGAAGAGATC  TTACTGTGTG  GACATCTCAT  GATGTGAACG   350
       N N T G     K R S       Y C V       D I S .    C E R
      I I Q       G R D L     T V W       T S H      D V N G
     . Y R       E E I       L L C G     H L M     M . T

GCATACTCAC  TGCTAAAGAG  GACTTGTGGC  TGTCAGACAA  CCATTTACTT   400
       H T H       C . R G     L V A       V R Q      P F T
      I L T       A K E       D L W L     S D N      H L L
     A Y S L     L K R       T C G       C Q T T    I Y L

AAATAGCAGG  TTCTATTACT  TGAAGTGCCA  GTGCTGCGAC  TGCACATTTG   450
       I A G       S I T       . S A S     A A T      A H L
      K . Q V     L L L       E V P       V L R L    H I C
     N S R       F Y Y L     K C Q       C C D     C T F V

TGCAACTCTT  AACCCAGCCA  CATTTCTTCC  AGACAATGAA  GAAAGATAG    500
       C N S .     P S H       I S S       R Q . R    K D R
      A T L       N P A T     F L P       D N E      E K I E
     Q L L       T Q P       H F F Q     T M K     K R .
```

FIG. 38b

|  10<br>1234567890 |  20<br>1234567890 |  30<br>1234567890 |  40<br>1234567890 |  50<br>1234567890 |     |
| --- | --- | --- | --- | --- | --- |
| AACATAACTG<br>T . L<br>H N C<br>N I T V | TCAACAAGTA<br>S T S N<br>Q Q V<br>N K . | ATTGCTCAAA<br>C S N<br>I A Q T<br>L L K | CCTATGCTGC<br>L C C<br>Y A A<br>P M L L | TCGAGGGGAC<br>S R G P<br>R G D<br>E G T | 550 |
| CTTCTAGAGG<br>S R G<br>L L E V<br>F . R | TTCCCTTGAC<br>S L D<br>P L T<br>F P . L | TGATCCCGAC<br>. S R P<br>D P D<br>I P T | CTCAACTTGT<br>Q L V<br>L N L Y<br>S T C | ATACTGATGG<br>Y . W<br>T D G<br>I L M E | 600 |
| AAGTTCCTTG<br>K F L G<br>S S L<br>V P W | GCAGAAAAAG<br>R K R<br>A E K G<br>Q K K | GACTTTGAAA<br>T L K<br>L . K<br>D F E K | AGCGGGGTAT<br>S G V C<br>A G Y<br>R G M | GCAGTGATCA<br>S D Q<br>A V I S<br>Q . S | 650 |
| GTGATAATGG<br>. . W<br>D N G<br>V I M E | AATACTTGAA<br>N T . K<br>I L E<br>Y L K | AGTAATCGCC<br>. S P<br>S N R L<br>V I A | TCACTCCAGG<br>H S R<br>T P G<br>S L Q E | AACTAGTGCT<br>N . C S<br>T S A<br>L V L | 700 |
| CACCTGGCAG<br>P G R<br>H L A E<br>T W Q | AACTAATAGC<br>T N S<br>L I A<br>N . . P | CCTCACTTGG<br>P H L G<br>L T W<br>S L G | GCACTAGAAT<br>T R I<br>A L E L<br>H . N | TAGGAGAAGG<br>R R R<br>G E G<br>. E K E | 750 |
| AAAAAGGGTA<br>K K G K<br>K R V<br>K G . | AATATATATT<br>Y I F<br>N I Y S<br>I Y I | CAGACTCTAA<br>R L .<br>D S K<br>Q T L S | GTATGCTTAC<br>V C L P<br>Y A Y<br>M L T | CTAGTCCTCC<br>S P P<br>L V L H<br>. S S | 800 |
| ATGCCCATGC<br>C P C<br>A H A<br>M P M Q | AGCAATATGG<br>S N M E<br>A I W<br>Q Y G | AGAGAGAGGG<br>R E G<br>R E R E<br>E R G | AATTCCTAAC<br>I P N<br>F L T<br>N S . L | TTCTGAGGGA<br>F . G N<br>S E G<br>L R E | 850 |
| ACACCTATCA<br>T Y Q<br>T P I N<br>H L S | ACCATCAGGG<br>P S G<br>H Q G<br>T I R E | AAGCCATTAG<br>K P L G<br>S H .<br>A I R | GAGATTATTA<br>D Y Y<br>E I I I<br>R L L | TTGGCTGTAC<br>W L Y<br>G C T<br>L A V Q | 900 |
| AGAAACCTAA<br>R N L K<br>E T .<br>K P K | AGAGGTGGCA<br>R W Q<br>R G G S<br>E V A | GTCTTACACT<br>S Y T<br>L T L<br>V L H C | GCCAGGGTCA<br>A R V I<br>P G S<br>Q G H | TCAGGAAGAA<br>R K K<br>S G R R<br>Q E E | 950 |
| GAGGAAAGGG<br>R K G<br>G K G<br>E E R E | AAATAGAAGG<br>K . K A<br>N R R<br>I E G | CAATCGCCAA<br>I A K<br>Q S P S<br>N R Q | GCGGATATTG<br>R I L<br>G Y .<br>A D I E | AAGCAAAAAA<br>K Q K K<br>S K K<br>A K K | 1000 |

FIG. 38c

|          10 |          20 |          30 |          40 |          50 |      |
|  1234567890 |  1234567890 |  1234567890 |  1234567890 |  1234567890 |      |
| AGCCGCAAGG  | CAGGACTCTC  | CATTAGAAAT  | GCTTATAGAA  | GGACCCCTAG  | 1050 |
|   P  Q  G   |   R  T  L   | H  .  K  C  | L  .  K     | D  P  .     |      |
| S  R  K  A  |   G  L  S   |   I  R  N   | A  Y  R  R  |   T  P  S   |      |
| A  A  R     | Q  D  S  P  |   L  E  M   |   L  I  E   | G  P  L  V  |      |
|             |             |             |             |             |      |
| TATGGGGTAA  | TCCCCTCTGG  | GAAACCAAGC  | CCCAGTACTC  | AGCAGGAAAA  | 1100 |
| Y  G  V  I  |   P  S  G   |   K  P  S   |   P  S  T  Q |  Q  E  K   |      |
| M  G  .     | S  P  L  G  | N  Q  A     | P  V  L     | S  R  K  N  |      |
|   W  G  N   | P  L  W     | E  T  K  P  | Q  Y  S     | A  G  K     |      |
|             |             |             |             |             |      |
| ATAGAATAGG  | AAACCTCACA  | AGGACATACT  | TTCCTCCCCT  | CCAGATGGCT  | 1150 |
| .  N  R     | K  P  H  K  |   D  I  L   |   S  S  P   | P  D  G  .  |      |
|   R  I  G   | N  L  T     | R  T  Y  F  | P  P  L     |   Q  M  A   |      |
| I  E  .  E  |   T  S  Q   |   G  H  T   | F  L  P  S  |   R  W  L   |      |
|             |             |             |             |             |      |
| AGCCACTGAG  | GAAGGAA     |             |             |             | 1167 |
|   P  L  R   |   K  E      |             |             |             |      |
| S  H  .  G  | R           |             |             |             |      |
| A  T  E     | E  G        |             |             |             |      |

FIG. 39a

```
          10          20          30          40          50
  1234567890  1234567890  1234567890  1234567890  1234567890
  AACTTGCGTG  CTAGAAGGAC  TAAGGAAAAC  TAGGAAGACT  ATGAATTATT    50
   N L R A     R R T       K E N      . E D Y      E L F
  T C V       L E G L     R K T       R K T       M N Y S
   L A C      . K D       . G K L      G R L      . I I

CAATGATGTC  CACTATAACA  CAGGGGAAAG  GAAGAAAATC  CTACTGCCTT   100
   N D V       H Y N T     G E R       K K I       L L P F
  M M S       T I T       Q G K G     R K S       Y C L
  Q . C P     L . H       R G K       E E N P     T A F

TCTGGAGAGA  CTAAGGGAGG  CATTGAGGAA  GCATACCAGG  CAAGTGGACA   150
   W R D      . G R        H . G S     I P G       K W T
  S G E T     K G G       I E E       A Y Q A     S G H
   L E R      L R E A      L R K       H T R      Q V D I

TTGGAGGCTC  TGGAAAAGGG  AAAAGTTGGG  CAAATTGAAT  GCCTAATAGG   200
   L E A L     E K G       K V G       Q I E C     L I G
  W R L       W K R E     K L G       K L N       A . . G
   G G S       G K G       K S W A    N . M       P N R

GCTTGCTTCC  AGTGCAGTCT  ACAAGGACGC  TTTAGAAAAG  ATTGTCCAAG   250
   L A S       S A V Y     K D A       L E K       I V Q V
  L L P       V Q S       T R T L     . K R       L S K
  A C F Q     C S L       Q G R       F R K D     C P S

TAGAAATAAG  CCGCCCCTCG  TCCATGCCCC  TTATGTCAAG  GGAATCACTG   300
   E I S       R P S       S M P L     M S R       E S L
  . K . A     A P R       P C P       L C Q G     N H W
   R N K      P P L V      H A P       Y V K       G I T G

GAAGGCCTAC  TGCCCCAGGG  GACGAAGGTC  CTCTGAGTCA  GAAGCCACTA   350
   E G L L     P Q G       T K V       L . V R     S H .
  K A Y       C P R G     R R S       S E S       E A T N
   R P T      A P G       D E G P      L S Q       K P L

ACCTGATGAT  CCAGCAGCAG  GACTGAGGGT  GCCCGGGGCA  AGTGCCAGCC   400
   P D D      P A A G       L R V      P G A       S A S P
   L M I     Q Q Q         D . G C    P G Q       V P A
  T . . S     S S R        T E G      A R G K     C Q P

CATGCCATCA  CCCTCAGAGC  CCCGGGTATG  TTTGACCATT  GAGAGCCAGG   450
   C H H      P Q S        P G Y V     . P L       R A R
  H A I T     L R A       P G M       F D H .     E P G
  M P S       P S E P      R V C       L T I      E S Q E

AAGTTAACTG  TCTCCTGGAC  ACTGGCGCAG  CCTTCTCAGT  CTTACTTTCC   500
   K L T V     S W T       L A Q       P S Q S     Y F P
  S . L       S P G H      W R S       L L S       L T F L
   V N C      L L D        T G A A     F S V       L L S
```

FIG. 39b

```
         10         20         30         40         50
     1234567890 1234567890 1234567890 1234567890 1234567890
     TGTCCCAGAC AATTGTCCTC CAGATCTGTC ACTATCCGAG GGGTCCTAAG        550
      V P D      N C P P    D L S      L S E      G S . D
       S Q T      I V L      Q I C H    Y P R     G P K
      C P R Q    L S S       R S V      T I R G   V L R

ACAGCCAGTC ACTACATACT TCTCTCAGCC ACTAAGTTGT GACTGGGGAA        600
      S Q S      L H T       S L S H    . V V     T G E
       T A S H    Y I L       L S A      T K L .   L G N
      Q P V      T T Y F     S Q P      L S C     D W G T

CTTTACTCTT TTCACATGCT TTTCTAATTA TGCCTGAAAG CCCCACTCCC        650
      L Y S F     H M L      F . L      C L K A    P L P
       F T L      F T C F    S N Y      A . K     P H S L
      L L F       S H A      F L I M    P E S      P T P

TTGTTAGGGA GAGACATTTT AGCAAAAGCA GGGGCCATTA TACACCTGAA        700
      C . G      E T F .     Q K Q      G P L      Y T . T
       V R E      R H F      S K S R    G H Y     T P E
      L L G R    D I L       A K A      G A I I    H L N

CATAGGAAAA GGAATACCCA TTTGCTGTCC CCTGCTTGAG GAAGGAATTA        750
      . E K      E Y P       F A V P    C L R      K E L
       H R K R    N T H       L L S      P A . G   R N .
      I G K      G I P I     C C P      L L E     E G I N

ATCCTGAAGT CTGGGCAATA GAAGGACAAT ATGGACAAGC AAAGAATGCC        800
      I L K S    G Q .       K D N      M D K Q    R M P
       S . S     L G N R     R T I      W T S      K E C P
      P E V      W A I       E G Q Y    G Q A     K N A

CGTCCTGTTC AAGTTAAACT AAAGGATTCT GCCTCCTTTC CCTACCAAAG        850
      V L F      K L N .     R I L      P P F      P T K G
       S C S      S . T       K G F C    L L S     L P K
      R P V Q    V K L       K D S      A S F P   Y Q R

GAAGTACCCT CTTAGACCCG AGGCCCTACA AGGACTCAAA AGATTGTTAA        900
      S T L      L D P       R P Y K    D S K      D C .
       E V P S   . T R       G P T      R T Q K   I V K
      K Y P      L R P E     A L Q      G L K     R L L R

GGACCTAAAA GCCCAAGGCC TAGTAAAACC ATGCAGTAGC CCCTGCAATA        950
      G P K S    P R P       S K T      M Q . P    L Q Y
       D L K     A Q G L      V K P     C S S      P C N T
      T . K      P K A       . . N H    A V A     P A I

CTCCAATTTT AGGAGTAAGG AAACCCAACG GACAGTGGAG GTTAGTGCAA       1000
      S N F      R S K E      T Q R     T V E      V S A R
       P I L     G V R        K P N G   Q W R      L V Q
      L Q F .    E . G        N P T     D S G G    . C K
```

FIG. 39c

|  | 10<br>1234567890 | 20<br>1234567890 | 30<br>1234567890 | 40<br>1234567890 | 50<br>1234567890 |  |
|---|---|---|---|---|---|---|
|  | GATCTCAGGA<br>S Q D<br>D L R I<br>I S G | TTATTAATGA<br>Y . .<br>I N E<br>L L M R | GGCTGTTTTT<br>G C F S<br>A V F<br>L F F | CCTCTATACC<br>S I P<br>P L Y P<br>L Y T | CAGCTGTATC<br>S C I<br>A V S<br>Q L Y L | 1050 |
|  | TAGCCCTTAT<br>. P L Y<br>S P Y<br>A L I | ACTCTGCTTT<br>S A F<br>T L L S<br>L C F | CCCTAATACC<br>P N T<br>L I P<br>P . Y Q | AGAGGAAGCA<br>R G S R<br>E E A<br>R K Q | GAGTAGTTTA<br>V V Y<br>E . F T<br>S S L | 1100 |
|  | CAGTCCTGGA<br>S P G<br>V L D<br>Q S W T | CCTTAAGGAT<br>P . G C<br>L K D<br>L R M | GCCTCTTTCT<br>L F L<br>A S F C<br>P L S | GCATCCCTGT<br>H P C<br>I P V<br>A S L Y | ACATCCTGAT<br>T S . F<br>H P D<br>I L I | 1150 |
|  | TCTCAATTCT<br>S I L<br>S Q F L<br>L N S | TGTTTGTCTT<br>V C L<br>F V F<br>C L S L | TGAAGATCCT<br>. R S F<br>E D P<br>K I L | TTGAACCCAA<br>E P N<br>L N P M<br>. T Q | TGTCTCAATT<br>V S I<br>S Q F<br>C L N S | 1200 |
|  | CACCTGGACT<br>H L D C<br>T W T<br>P G L | GTTTTACCCC<br>F T P<br>V L P Q<br>F Y P | AGGGGTTCCG<br>G V P<br>G F R<br>R G S G | GGATAGCCCC<br>G . P P<br>D S P<br>I A P | CATCTATTTG<br>S I W<br>H L F G<br>I Y L | 1250 |
|  | GCCAGGCATT<br>P G I<br>Q A L<br>A R H . | AGCCCAAGAC<br>S P R L<br>A Q D<br>P K T | TTGAGCCAAT<br>E P I<br>L S Q F<br>. A N | TCTCATACCT<br>L I P<br>S Y L<br>S H T W | GGACATCTTG<br>G H L V<br>D I L<br>T S C | 1300 |
|  | TCCTTCGGTA<br>L R Y<br>S F G M<br>P S V | TGGGATGATT<br>G M I<br>G . F<br>W D D L | TAATTTTAGC<br>. F . P<br>N F S<br>I L A | CACCCGTTCA<br>P V Q<br>H P F R<br>T R S | GAAACCTTGT<br>K P C<br>N L V<br>E T L C | 1350 |
|  | GCCATCAAGC<br>A I K P<br>P S S<br>H Q A | CACCCAAGCG<br>P K R<br>H P S V<br>T Q A | TTCTTAAATT<br>S . I<br>L K F<br>F L N F | TCCTCACTCC<br>S S L R<br>P H S<br>L T P | GTGTGGCTAC<br>V A T<br>V W L Q<br>C G Y | 1400 |
|  | AAGGTTTCCA<br>R F P<br>G F Q<br>K V S K | AACCAAAGGC<br>N Q R L<br>T K G<br>P K A | TCAGCTCTGC<br>S S A<br>S A L L<br>Q L C | TCACAGCAGG<br>H S R<br>T A G<br>S Q Q V | TTAAATACTT<br>L N T .<br>. I L<br>K Y L | 1450 |
|  | AGGGTTAAAA<br>G . N<br>R V K I<br>G L K | TTATCCAAAG<br>Y P K<br>I Q R<br>L S K G | GCACCAGGGC<br>A P G P<br>H Q G<br>T R A | CCTCTGTGAG<br>S V R<br>P L . G<br>L C E | GAATGTATCC<br>N V S<br>M Y P<br>E C I Q | 1500 |

FIG. 39d

```
         10          20          30          40          50
 1234567890  1234567890  1234567890  1234567890  1234567890
 AACCTGTACT  GGCTTATCTT  CATCCCAAAA  CCCTAAAGCA  ACTAAGAAGG   1550
 N  L  Y  W   L  I  F    I  P  K    P  .  S  N   .  E  G
  T  C  T    G  L  S  S   S  Q  N    P  K  A    T  K  K  V
   P  V  L    A  Y  L    H  P  K  T   L  K  Q    L  R  R

TCCTTGGCAT  AACAGGTTTC  TGCCGAA                              1577
 P  W  H     N  R  F  L   P
  L  G  I    T  G  F     C  R
   S  L  A  .  Q  V  S   A  E
```

FIG. 40

|  10<br>1234567890 |  20<br>1234567890 |  30<br>1234567890 |  40<br>1234567890 |  50<br>1234567890 | |
|---|---|---|---|---|---|
| TCCAGCAGCA<br>S  S  S  R | GGACTGAGGG<br>T  E  G | TGCCCGGGGC<br>A  R  G | AAGTGCCAGC<br>K  C  Q  P | CCATGCCATC<br>M  P  S | 50 |
| ACCCTCAGAG<br>P  S  E | CCCCGGGTAT<br>P  R  V  C | GTTTGACCAT<br>L  T  I | TGAGAGCCAG<br>E  S  Q | GAAGTTAACT<br>E  V  N  C | 100 |
| GTCTCCTGGA<br>L  L  D | CACTGGCGCA<br>T  G  A | GCCTTCTCAG<br>A  F  S  V | TCTTACTTTC<br>L  L  S | CTGTCCAGA<br>C  P  R | 150 |
| CAATTGTCCT<br>Q  L  S  S | CCAGATCTGT<br>R  S  V | CACTATCCGA<br>T  I  R | GGGGTCCTAA<br>G  V  L  R | GACAGCCAGT<br>Q  P  V | 200 |
| CACTACATAC<br>T  T  Y | TTCTCTCAGC<br>F  S  Q  P | CACTAAGTTG<br>L  S  C | TGACTGGGGA<br>D  W  G | ACTTTACTCT<br>T  L  L  F | 250 |
| TTTCACATGC<br>S  H  A | TTTTCTAATT<br>F  L  I | ATGCCTGAAA<br>M  P  E  S | GCCCCACTCC<br>P  T  P | CTTGTTAGGG<br>L  L  G | 300 |
| AGAGACATTT<br>R  D  I  L | TAGCAAAAGC<br>A  K  A | AGGGGCCATT<br>G  A  I | ATACACCTGA<br>I  H  L  N | ACATAGGAAA<br>I  G  K | 350 |
| AGGAATACCC<br>G  I  P | ATTTGCTGTC<br>I  C  C  P | CCCTGCTTGA<br>L  L  E | GGAAGGAATT<br>E  G  I | AATCCTGAAG<br>N  P  E  V | 400 |
| TCTGGGCAAT<br>W  A  I | AGAAGGACAA<br>E  G  Q | TATGGACAAG<br>Y  G  Q  A | CAAAGAATGC<br>K  N  A | CCGTCCTGTT<br>R  P  V | 450 |
| CAAGTTAAAC<br>Q  V  K  L | TAAAGGATTC<br>K  D  S | TGCCTCCTTT<br>A  S  F | CCCTACCAAA<br>P  Y  Q  R | GGAAGTACCC<br>K  Y  P | 500 |
| TCTTAGACCC<br>L  R  P | GAGGCCCTAC<br>E  A  L  Q | AAGGACTCAA<br>G  L  K | AAGATTGTTA<br>R  L  L | AGGACCT<br>R  T | 547 |

VIRAL MATERIAL AND NUCLEOTIDE FRAGMENTS ASSOCIATED WITH MULTIPLE SCLEROSIS, FOR DIAGNOSTIC, PROPHYLACTIC AND THERAPEUTIC PURPOSES

This is a Division of application Ser. No. 08/691,563 filed Aug. 2, 1996, which issued as U.S. Pat. No. 6,001,987 on Dec. 14, 1999.

Multiple sclerosis (MS) is a demyelinating disease of the central nervous system (CNS) the cause of which remains as yet unknown.

Many studies have supported the hypothesis of a viral aetiology of the disease, but none of the known viruses tested has proved to be the causal agent sought: a review of the viruses sought for several years in MS has been compiled by E. Norrby (1) and R. T. Johnson (2).

Recently, a retrovirus different from the known human retroviruses has been isolated in patients suffering from MS (3, 4, and 5). The authors were also able to show that this retrovirus could be transmitted in vitro, that patients suffering from MS produced antibodies capable of recognizing proteins associated with the infection of leptomeningeal cells by this retrovirus, and that the expression of the latter could be strongly stimulated by the immediate-early genes of some herpes-viruses (6).

All these results point to the role in MS of at least one unknown retrovirus or of a virus having reverse transcriptase activity which is detectable according to the method published by H. Perron (3) and qualified as "LM7-like RT" activity. The content of the publication identified by (3) is incorporated in the present description by reference.

Recently, the Applicant's studies have enabled two continuous cell lines infected with natural isolates originating from two different patients suffering from MS to be obtained by a culture method as described in the document WO-A-93/20188, the content of which is incorporated in the present description by reference. These two lines, derived from human choroid plexus cells, designated LM7PC and PLI-2, were deposited with the ECACC on Jul. 22nd 1992 and Jan. 8th 1993, respectively, under numbers 92072201 and 93010817, in accordance with the provisions of the Budapest Treaty. Moreover, the viral isolates possessing LM7-like RT activity were also deposited with the ECACC under the overall designation of "strains". The "strain" or isolate harboured by the PLI-2 line, designated POL-2, was deposited with the ECACC on Jul. 22nd, 1992 under No. V92072202. The "strain" or isolate harboured by the LM7PC line, designated MS7PG, was deposited with the ECACC on Jan. 8th 1993 under No. V93010816.

Starting from the cultures and isolates mentioned above, characterized by biological and morphological criteria, the next step was to endeavour to characterize the nucleic acid material associated with the viral particles produced in these cultures.

The portions of the genome which have already been characterized have been used to develop tests for molecular detection of the viral genome and imunoserological tests, using the amino acid sequences encoded by the nucleotide sequences of the viral genome, in order to detect the immune response directed against epitopes associated with the infection and/or viral expression.

These tools have already enabled an association to be confirmed between MS and the expression of the sequences identified in the patents cited later. However, the viral system discovered by the Applicant is related to a complex retroviral system. In effect, the sequences to be found encapsidated in the extracellular viral particles produced by the different cultures of cells of patients suffering from MS show clearly that there is coencapsidation of retroviral genomes which are related but different from the "wild-type" retroviral genome which produces the infective viral particles. This phenomenon has been observed between replicative retroviruses and endogenous retroviruses belonging to the same family, or even heterologous retroviruses. The notion of endogenous retroviruses is very important in the context of our discovery since, in the case of MSRV-1, it has been observed that endogenous retroviral sequences comprising sequences homologous to the MSRV-1 genome exist in normal human DNA. The existence of endogenous retroviral elements (ERV) related to MSRV-1 by all or part of their genome explains the fact that the expression of the MSRV-1 retrovirus in human cells is able to interact with closely related endogenous sequences. These interactions are to be found in the case of pathogenic and/or infectious endogenous retroviruses (for example some ecotropic strains of the urine leukaemia virus), and in the case of exogenous retroviruses whose nucleotide sequence may be found partially or wholly, in the form of ERVs, in the host animal's genome (e.g. mouse exogenous mammary tumor virus transmitted via the milk). These interactions consist mainly of (i) a trans-activation or coactivation of ERVs by the replicative retrovirus (ii) and "illegitimate" encapsidation of RNAs related to ERVS, or of ERVS—or even of cellular RNAs—simply possessing compatible encapsidation sequences, in the retroviral particles produced by the expression of the replicative strain, which are sometimes transmissible and sometimes with a pathogenicity of their own, and (iii) more or less substantial recombinations between the coencapsidated genomes, in particular in the phases of reverse transcription, which lead to the formation of hybrid genomes, which are sometimes transmissible and sometimes with a pathogenicity of their own.

Thus, (i) different sequences related to MSRV-1 have been found in the purified viral particles; (ii) molecular analysis of the different regions of the MSRV-1 retroviral genome should be carried out by systematically analyzing the coencapsidated, interfering and/or recombined sequences which are generated by the infection and/or expression of MSRV-1; furthermore, some clones may have defective sequence portions produced by the retroviral replication and template errors and/or errors of transcription of the reverse transcriptase; (iii) the families of sequences related to the same retroviral genomic region provide the means for an overall diagnostic detection which may be optimized by the identification of invariable regions among the clones expressed, and by the identification of reading frames responsible for the production of antigenic and/or pathogenic polypeptides which may be produced only by a portion, or even by just one, of the clones expressed, and, under these conditions, the systematic analysis of the clones expressed in the region of a given gene enables the frequency of variation and/or of recombination of the MSRV-1 genome in this region to be evaluated and the optimal sequences for the applications, in particular diagnostic applications, to be defined; (iv) the pathology caused by a retrovirus such as MSRV-1 may be a direct effect of its expression and of the proteins or peptides produced as a result thereof, but also an effect of the activation, the encapsidation or the recombination of related or heterologous genomes and of the proteins or peptides produced as a result thereof; thus, these genomes associated with the expression of and/or infection by MSRV-1 are an integral part of the potential pathogenicity of this virus, and hence constitute means of diagnostic detection and special therapeutic targets. Similarly, any agent associated with or cofactor of these interactions responsible for the pathogenesis in question, such as MSRV-2 or the glyotoxic factor which are described in the patent application published under No. FR-2,716,198, may participate in the development of an overall and very effective strategy for the diagnosis, prognosis, therapeutic monitoring and/or integrated therapy of MS in particular, but also of any other disease associated with the same agents.

In this context, a parallel discovery has been made in another autoimmune disease, rheumatoid arthritis (RA), which has been described in the French Patent Application filed under No. 95/02960. This discovery shows that, by applying methodological approaches similar to the ones which were used in the Applicant's work on MS, it was possible to identify a retrovirus expressed in RA which shares the sequences described for MSRV-1 in MS, and also the coexistence of an associated MSRV-2 sequence also described in MS. As regards MSRV-1, the sequences detected in common in MS and RA relate to the pol and gag genes. In the current state of knowledge, it is possible to associate the gag and pol sequences described with the MSRV-1 strains expressed in these two diseases.

The present patent application relates to various results which are additional to those already protected by the following French Patent Applications:

No. 92/04322 of Apr. 3, 1992, published under No. 2,689, 519;
No. 92/13447 of Nov. 3, 1992, published under No. 2,689, 521;
No. 92/13443 of Nov. 3, 1992, published under No. 2,689, 520;
No. 94/01529 of Feb. 4, 1994, published under No. 2,715, 936;
No. 94/01531 of Feb. 4, 1994, published under No. 2,715, 939;
No. 94/01530 of Feb. 4, 1994, published under No. 2,715, 936;
No. 94/01532 of Feb. 4, 1994, published under No. 2,715, 937;
No. 94/14322 of Nov. 24, 1994, published under No. 2,727, 428;
and No. 94/15810 of Dec. 23, 1994; published under No. 2,728,585.

The present invention relates, in the first place, to a viral material, in the isolated or purified state, which may be recognized or characterized in different ways:

its genome comprises a nucleotide sequence chosen from the group including the sequences SEQ ID NO:46, SEQ ID NO:51, SEQ ID NO:52, SEQ ID NO:53, SEQ ID NO:56, SEQ ID NO:58, SEQ ID NO:59, SEQ ID NO:60, SEQ ID NO:61, SEQ ID NO:89, their complementary sequences and their equivalent sequences, in particular nucleotide sequences displaying, for any succession of 100 contiguous monomers, at least 50% and preferably at least 70% homology with the said sequences SEQ ID NO:46, SEQ ID NO:51, SEQ ID NO:52, SEQ ID NO:53, SEQ ID NO:56, SEQ ID NO:58, SEQ ID NO:59, SEQ ID NO:60 SEQ ID NO:61, SEQ ID NO:89, respectively, and their complementary sequences;

the region of its genome comprising the env and pol genes and a portion of the gag gene, excluding the subregion having a sequence identical or equivalent to SEQ ID NO:1, codes for any polypeptide displaying, for any contiguous succession of at least 30 amino acids, at least 50% and preferably at least 70% homology with a peptide sequence encoded by any nucleotide sequence chosen from the group including SEQ ID NO:46, SEQ ID NO:51, SEQ ID NO:52, SEQ ID NO:53, SEQ ID NO:56, SEQ ID NO:58, SEQ ID NO:59, SEQ ID NO:60 SEQ ID NO:61 SEQ ID NO:89 and their complementary sequences;

the pol gene comprises a nucleotide sequence partially or totally identical or equivalent to SEQ ID NO:57, excluding SEQ ID NO:1.

the gag gene comprises a nucleotide sequence partially or totally identical or equivalent to SEQ ID NO:88.

As indicated above, according to the present invention, the viral material as defined above is associated with MS. And as defined by reference to the pol or gag gene of MSRV-1, and more especially to the sequences SEQ ID NOS 51, 56, 57, 59, 60, 61, 88 and 89, this viral material is associated with RA.

The present invention also relates to different nucleotide fragments each comprising a nucleotide sequence chosen from the group including:

(a) all the genomic sequences, partial and total, of the pol gene of the MSRV-1 virus, except for the total sequence of the nucleotide fragment defined by SEQ ID NO:1;

(b) all the genomic sequences, partial and total, of the env gene of MSRV-1;

(c) all the partial genomic sequences of the gag gene of MSRV-1;

(d) all the genomic sequences overlapping the pol gene and the env gene of the MSRV-1 virus, and overlapping the pol gene and the gag gene;

(e) all the sequences, partial and total, of a clone chosen from the group including the clones FBd3 (SEQ ID NO:46), t pol (SEQ ID NO:51), JLBc1 (SEQ ID NO:52), JLBc2 (SEQ ID NO:53) and GM3 (SEQ ID NO:56), FBd13 (SEQ ID NO:58), LB19 (SEQ ID NO:59), LTRGAG12 (SEQ ID NO:60), FP6 (SEQ ID NO:61), G+E+A (SEQ ID NO:89), excluding any nucleotide sequence identical to or lying within the sequence defined by SEQ ID NO:1;

(f) sequences complementary to the said genomic sequences;

(g) sequences equivalent to the said sequences (a) to (e), in particular nucleotide sequences displaying, for any succession of 100 contiguous monomers, at least 50% and preferably at least 70% homology with the said sequences (a) to (d).

provided that this nucleotide fragment does not comprise or consist of the sequence ERV-9 as described in LA MANTIA et al. (18).

The term genomic sequences, partial or total, includes all sequences associated by coencapsidation or by coexpression, or recombined sequences.

Preferably, such a fragment comprises:

either a nucleotide sequence identical to a partial or total genomic sequence of the pol gene of the MSRV-1 virus, except for the total sequence of the nucleotide fragment defined by SEQ ID NO:1, or identical to any sequence equivalent to the said partial or total genomic sequence, in particular one which is homologous to the latter;

or a nucleotide sequence identical to a partial or total genomic sequence of the env gene of the MSRV-1 virus, or identical to any sequence complementary to the said nucleotide sequence, or identical to any sequence equivalent to the said nucleotide sequence, in particular one which is homologous to the latter.

In particular, the invention relates to a nucleotide fragment comprising a coding nucleotide sequence which is partially or totally identical to a nucleotide sequence chosen from the group including:

- the nucleotide sequence defined by SEQ ID NO:40, SEQ ID NO:62 or SEQ ID NO:89;
- sequences complementary to SEQ ID NO:40, SEQ ID NO:62 or SEQ ID NO:89;
- sequences equivalent, and in particular homologous to SEQ ID NO:40, SEQ ID NO:62 or SEQ ID NO:89;
- sequences coding for all or part of the peptide sequence defined by SEQ ID NO:39, SEQ ID NO:63 or SEQ ID NO:90;
- sequences coding for all or part of a peptide sequence equivalent, in particular homologous to SEQ ID NO:39, SEQ ID NO:63 or SEQ ID NO:90, which is capable of being recognized by sera of patients infected with the MSRV-1 virus, or in whom the MSRV-1 virus has been reactivated.

The invention also relates to any nucleic acid probe for detection of a pathogenic and/or infective agent associated with MS, which is capable of hybridizing specifically with any fragment such as is defined above, belonging or lying within the genome of the said pathogenic agent. It relates, in addition, to any nucleic acid probe for detection of a pathogenic and/or infective agent associated with RA, which is capable of hybridizing specifically with any fragment as defined above by reference to the pol and gag genes, and especially with respect to the sequences SEQ ID NOS 40, 51, 56, 59, 60, 61, 62, 89 and SEQ ID NOS 39, 63 and 90.

The invention also relates to a primer for the amplification by polymerization of an RNA or a DNA of a viral material, comprising a nucleotide sequence identical or equivalent to at least one portion of the nucleotide sequence of any fragment such as is defined above, in particular a nucleotide sequence displaying, for any succession of 10 contiguous monomers, at least 70% homology with at least the said portion of the said fragment. Preferably, the nucleotide sequence of such a primer is identical to any one of the sequences chosen from the group including SEQ ID NO:47 to SEQ ID NO:50, SEQ ID NO:55 and SEQ ID NO:64 SEQ ID NO:86.

Generally speaking the invention also encompasses any RNA or DNA, and in particular replication vector, comprising a genomic fragment of the viral material such as is defined above, or a nucleotide fragment such as is defined above.

The invention also relates to the different peptides encoded by any open reading frame belonging to a nucleotide fragment such as is defined above, in particular any polypeptide, for example any oligopeptide forming or comprising an antigenic determinant recognized by sera of patients infected with the MSRV-1 virus and/or in whom the MSRV-1 virus has been reactivated. Preferably, this polypeptide is antigenic, and is encoded by the open reading frame beginning, in the 5'–3' direction, at nucleotide 181 and ending at nucleotide 330 of SEQ ID NO:1.

In particular, the invention relates to an antigenic polypeptide recognized by the sera of patients infected with the MSRV-1 virus, and/or in whom the MSRV-1 virus has been reactivated, whose peptide sequence is partially or totally identical or is equivalent to the sequence defined by SEQ ID NO:39, SEQ ID NO:63 and SEQ ID NO:87; such a sequence is identical, for example, to any sequence chosen from the group including the sequences SEQ ID NO:41 to SEQ ID NO:44, SEQ ID NO:63 and SEQ ID NO:87.

The present invention also proposes mono- or polyclonal antibodies directed against the MSRV-1 virus, which are obtained by the immunological reaction of a human or animal body to an immunogenic agent consisting of an antigenic polypeptide such as is defined above.

The invention next relates to:

- reagents for detection of the MSRV-virus, or of an exposure to the latter, comprising, as reactive substance, a peptide, in particular an antigenic peptide, such as is defined above, or an anti-ligand, in particular an antibody to the said peptide;
- all diagnostic, prophylactic or therapeutic compositions comprising one or more peptides, in particular antigenic peptides, such as are defined above, or one or more anti-ligands, in particular antibodies to the peptides, discussed above; such a composition is preferably, and by way of example, a vaccine composition.

The invention also relates to any diagnostic, prophylactic or therapeutic composition, in particular for inhibiting the expression of at least one pathogenic and/or infective agent associated with MS comprising a nucleotide fragment such as is defined above or a polynucleotide, in particular oligonucleotide, whose sequence is partially identical to that of the said fragment, except for that of the fragment having the nucleotide sequence SEQ ID NO:1. Likewise, it relates to any diagnostic, prophylactic or therapeutic composition, in particular for inhibiting the expression of at least one pathogenic and/or infective agent associated with RA, comprising a nucleotide fragment such as is defined above by reference to the pol and gag genes, and especially with respect to the sequences SEQ ID NOS 40, 51, 56, 59, 60, 61, 62 and 89.

According to the invention, these same fragments or polynucleotides, in particular oligonucleotides, may participate in all suitable compositions for detecting, according to any suitable process or method, a pathological and/or infective agent associated with MS and with RA, respectively, in a biological sample. In such a process, an RNA and/or a DNA presumed to belong or originating from the said pathological and/or infective agent, and/or their complementary RNA and/or DNA, is/are brought into contact with such a composition.

The present invention also relates to any process for detecting the presence or exposure to such a pathological and/or infective agent, in a biological sample, by bringing this sample into contact with a peptide, in particular an antigenic peptide such as is defined above, or an anti-ligand, in particular an anti-body to this peptide, such as is defined above.

In practice, and for example, a device for detection of the MSRV-1 virus comprises a reagent such as is defined above, supported by a solid support which is immunologically compatible with the reagent, and a means for bringing the biological sample, for example a sample of blood or of cerebrospinal fluid, likely to contain anti-MSRV-1 antibodies, into contact with this reagent under conditions permitting a possible immunological reaction, the foregoing items being accompanied by means for detecting the immune complex formed with this reagent.

Lastly, the invention also relates to the detection of anti-MSRV-1 antibodies in a biological sample, for example a sample of blood or of cerebrospinal fluid, according to which this sample is brought into contact with a reagent such as is defined above, consisting of an antibody, under conditions permitting their possible immunological reaction, and the presence of the immune complex thereby formed with the reagent is then detected.

Before describing the invention in detail, different terms used in the description and the claims are now defined:

strain or isolate is understood to mean any infective and/or pathogenic biological fraction containing, for example, viruses and/or bacteria and/or parasites, generating pathogenic and/or antigenic power, harboured by a culture or a living host; as an example, a viral strain according to the above definition can contain a coinfective agent, for example a pathogenic protist, the term "MSRV" used in the present description denotes any pathogenic and/or infective agent associated with MS, in particular a viral species, the attenuated strains of the said viral species or the defective-interfering particles or particles containing coencapsidated genomes, or alternatively genomes recombined with a portion of the MSRV-1 genome, derived from this species. Viruses, and especially viruses containing RNA, are known to have a variability resulting, in particular, from relatively high rates of spontaneous mutation (7), which will be borne in mind below for defining the notion of equivalence, human virus is understood to mean a virus capable of infecting, or of being harboured by human beings, in view of all the natural or induced variations and/or recombination which may be encountered when implementing the present invention, the subjects of the latter, defined above and in the claims, have been expressed including the equivalents or derivatives of the different biological materials defined below, in particular of the homologous, nucleotide or peptide sequences, the variant of a virus or of a pathogenic and/or infective agent according to the invention comprises at least one antigen recognized by at least one antibody directed against at least one corresponding antigen of the said virus and/or said pathogenic and/or infective agent, and/or a genome any part of which is detected by at least one hybridization probe and/or at least one nucleotide amplification primer specific for the said virus and/or pathogenic and/or infective agent, such as, for example, for the MSRV-1 virus, the primers and probes having a nucleotide sequence chosen from SEQ ID No. 20 to SEQ ID No. 24, SEQ ID No. 26, SEQ ID No. 16 to SEQ ID No. 19, SEQ ID No. 31 to SEQ ID No. 33, SEQ ID No. 45, SEQ ID No. 47, SEQ ID No. 48, SEQ ID No. 49, SEQ ID No. 50, SEQ ID No. 45 and their complementary sequences, under particular hybridization conditions well known to a person skilled in the art, according to the invention, a nucleotide fragment or an oligonucleotide or polynucleotide is an arrangement of monomers, or a biopolymer, characterized by the informational sequence of the natural nucleic acids, which is capable of hybridizing with any other nucleotide fragment under predetermined conditions, it being possible for the arrangement to contain monomers of different chemical structures and to be obtained from a molecule of natural nucleic acid and/or by genetic recombination and/or by chemical synthesis; a nucleotide fragment may be identical to a genomic fragment of the MSRV-1 virus discussed in the present invention, in particular a gene of this virus, for example pol or env in the case of the said virus, thus, a monomer can be a natural nucleotide of nucleic acid whose constituent elements are a sugar, a phosphate group and a nitrogenous base; in RNA the sugar is ribose, in DNA the sugar is 2-deoxyribose; depending on whether the nucleic acid is DNA or RNA, the nitrogenous base is chosen from adenine, guanine, uracil, cytosine and thymine; or the nucleotide can be modified in at least one of the three constituent elements; as an example, the modification can occur in the bases, generating modified bases such as inosine, 5-methyldeoxy-cytidine, deoxyuridine, 5-(dimethylamino)deoxyuridine, 2,6-diaminopurine, 5-bromodeoxyuridine and any other modified base promoting hybridization; in the sugar, the modification can consist of the replacement of at least one deoxyribose by a polyamide (8), and in the phosphate group, the modification can consist of its replacement by esters chosen, in particular, from diphosphate, alkyl- and arylphosphonate and phosphorothioate esters, "informational sequence" is understood to mean any ordered succession of monomers whose chemical nature and order in a reference direction constitute or otherwise an item of functional information of the same quality as that of the natural nucleic acids, hybridization is understood to mean the process during which, under suitable working conditions, two nucleotide fragments having sufficiently complementary sequences pair to form a complex structure, in particular double or triple, preferably in the form of a helix, a probe comprises a nucleotide fragment synthesized chemically or obtained by digestion or enzymatic cleavage of a longer nucleotide fragment, comprising at least six monomers, advantageously from 10 to 100 monomers and preferably 10 to 30 monomers, and possessing a specificity of hybridization under particular conditions; preferably, a probe possessing fewer than 10 monomers is not used alone, but is used in the presence of other probes of equally short size or otherwise; under certain special conditions, it may be useful to use probes of size greater than 100 monomers; a probe may be used, in particular, for diagnostic purposes, such molecules being, for example, capture and/or detection probes, the capture probe may be immobilized on a solid support by any suitable means, that is to say directly or indirectly, for example by covalent bonding or passive adsorption, the detection probe may be labelled by means of a label chosen, in particular, from radioactive isotopes, enzymes chosen, in particular, from peroxidase and alkaline phosphatase and those capable of hydrolysing a chromogenic, fluorogenic or luminescent substrate, chromophoric chemical compounds, chromogenic, fluorogenic or luminescent compounds, nucleotide base analogues and biotin, the probes used for diagnostic purposes of the invention may be employed in all known hybridization techniques, and in particular the techniques termed "DOT-BLOT" (9), "SOUTHERN BLOT" (10), "NORTHERN BLOT", which is a technique identical to the "SOUTHERN BLOT" technique but which uses RNA as target, and the SANDWICH technique (11); advantageously, the SANDWICH technique is used in the present invention, comprising a specific capture probe and/or a specific detection probe, on the understanding that the capture probe and the detection probe must possess an at least partially different nucleotide sequence, any probe according to the present invention can hybridize in vivo or in vitro with RNA and/or with DNA in order to block the phenomena of replication, in particular translation and/or transcription, and/or to degrade the said DNA and/or RNA, a primer is a probe comprising at least six monomers, and advantageously from 10 to 30 monomers, possessing a specificity of hybridization under particular conditions for the initiation of an enzymatic polymerization, for example in an amplification technique such as PCR (polymerase chain reaction), in an elongation process such as sequencing, in a method of reverse transcription or the like, two nucleotide or peptide sequences are termed equivalent or derived with respect to one another, or with respect to a reference sequence, if functionally the corresponding biopolymers can perform substantially the same rôle, without being identical, as regards the application or use in question, or in the technique in which they participate; two sequences are, in particular, equivalent if they are obtained as a result of natural variability, in particular spontaneous mutation of the species from which they have been identified, or induced variability, as are two homologous sequences, homology being defined below, "variability" is understood to mean any spontaneous or induced modification of a sequence, in particular by substitution and/or insertion and/or deletion of nucleotides and/or of nucleotide fragments, and/or extension and/or shortening of the sequence at one or both ends; an unnatural variability can result from the genetic engineering techniques used, for example the choice of synthesis primers, degenerate or otherwise, selected for amplifying a nucleic acid; this variability can manifest itself in modifications of any starting sequence, considered as reference, and capable of being expressed by a degree of homology relative to the said reference sequence, homology characterizes the degree of identity of two nucleotide or peptide fragments compared; it is measured by the percentage identity which is determined, in particular, by direct comparison of nucleotide or peptide sequences, relative to reference nucleotide or peptide sequences, this percentage identity has been specifically determined for the nucleotide fragments, clones in particular, dealt with in the present invention, which are homologous to the fragments identified, for the MSRV-1 virus, by SEQ ID No. 1 to No. 9, SEQ ID NO:46, SEQ ID NO:51 to SEQ ID NO:53, SEQ ID NO:40, SEQ ID NO:56 and SEQ ID NO:57, as well as for the probes and primers homologous to the probes and primers identified by SEQ ID NO:20 to SEQ ID NO:24, SEQ ID NO:26, SEQ ID NO:16 to SEQ ID NO:19, SEQ ID NO:31 to SEQ ID NO:33, SEQ ID NO:45, SEQ ID NO:47, SEQ ID NO:48, SEQ ID NO:49, SEQ ID NO:50, SEQ ID NO:55, SEQ ID NO:40, SEQ ID NO:56 and SEQ ID NO:57; as an example, the smallest percentage identity observed between the different general consensus sequences of nucleic acids obtained from fragments of MSRV-1 viral RNA, originating from the LM7PC and PLI-2 lines according to a protocol detailed later, is 67% in the region described in FIG. 1, any nucleotide fragment is termed equivalent or derived from a reference fragment if it possesses a nucleotide sequence equivalent to the sequence of the reference fragment; according to the above definition, the following in particular are equivalent to a reference nucleotide fragment:

a) any fragment capable of hybridizing at least partially with the complement of the reference fragment,
b) any fragment whose alignment with the reference fragment results in the demonstration of a larger number of identical contiguous bases than with any other fragment originating from another taxonomic group,
c) any fragment resulting, or capable of resulting, from the natural variability of the species from which it is obtained,
d) any fragment capable of resulting from the genetic engineering techniques applied to the reference fragment,
e) any fragment containing at least eight contiguous nucleotides encoding a peptide which is homologous or identical to the peptide encoded by the reference fragment,
f) any fragment which is different from the reference fragment by insertion, deletion or substitution of at least one monomer, or extension or shortening at one or both of its ends; for example, any fragment corresponding to the reference fragment flanked at one or both of its ends by a nucleotide sequence not coding for a polypeptide, polypeptide is understood to mean, in particular, any peptide of at least two amino acids, in particular an oligopeptide or protein, extracted, separated or substantially isolated or synthesized through human intervention, in particular those obtained by chemical synthesis or by expression in a recombinant organism, polypeptide partially encoded by a nucleotide fragment is understood to mean a polypeptide possessing at least three amino acids encoded by at least nine contiguous monomers lying within the said nucleotide fragment, an amino acid is termed analogous to another amino acid when their respective physicochemical properties, such as polarity, hydrophobicity and/or basicity and/or acidity and/or neutrality are substantially the same; thus, a leucine is analogous to an isoleucine.

any polypeptide is termed equivalent or derived from a reference polypeptide if the polypeptides compared have substantially the same properties, and in particular the same antigenic, immunological, enzymological and/or molecular recognition properties; the following in particular are equivalent to a reference polypeptide:

a) any polypeptide possessing a sequence in which at least one amino acid has been replaced by an analogous amino acid,
b) any polypeptide having an equivalent peptide sequence, obtained by natural or induced variation of the said reference polypeptide and/or of the nucleotide fragment coding for the said polypeptide,
c) a mimotope of the said reference polypeptide,
d) any polypeptide in whose sequence one or more amino acids of the L series are replaced by an amino acid of the D series, and vice versa,
e) any polypeptide into whose sequence a modification of the side chains of the amino acids has been introduced, such as, for example, an acetylation of the amine functions, a carboxylation of the thiol functions, an esterification of the carboxyl functions,
f) any polypeptide in whose sequence one or more peptide bonds have been modified, such as, for example, carba, retro, inverso, retro-inverso, reduced and methylenoxy bonds, (g) any polypeptide at least one antigen of which is recognized by an antibody directed against a reference polypeptide, the percentage identity characterizing the homology of two peptide fragments compared is, according to the present invention, at least 50% and preferably at least 70%.

In view of the fact that a virus possessing reverse transcriptase enzymatic activity may be genetically characterized equally well in RNA and in DNA form, both the viral DNA and RNA will be referred to for characterizing the sequences relating to a virus possessing such reverse transcriptase activity, termed MSRV-1 according to the present description.

The expressions of order used in the present description and the claims, such as "first nucleotide sequence", are not adopted so as to express a particular order, but so as to define the invention more clearly.

Detection of a substance or agent is understood below to mean both an identification and a quantification, or a separation or isolation, of the said substance or said agent.

A better understanding of the invention will be gained on reading the detailed description which follows, prepared with reference to the attached figures, in which:

FIG. 1 shows general consensus sequences of nucleic acids of the MSRV-1B clones amplified by the PCR technique in the "pol" region defined by Shih (12), from viral DNA originating from the L47PC and PLI-2 lines, and identified under the references SEQ ID NO:3, SEQ ID NO:4, SEQ ID NO:5 and SEQ ID NO:6, and the common consensus with amplification primers bearing the reference SEQ ID NO:7;

FIG. 2 gives the definition of a functional reading frame for each MSRV-1B/"PCR pol" type family, the said families A to D being defined, respectively, by the nucleotide sequences SEQ ID NO:3, SEQ ID NO:4, SEQ ID NO:5 and SEQ ID NO:6 described in FIG. 1;

FIG. 3 gives an example of consensus of the MSRV-2B sequences., identified by SEQ ID NO:11;

FIG. 4 is a representation of the reverse transcriptase (RT) activity in dpm (disintegrations per minute) in the sucrose fractions taken from a purification gradient of the virions produced by the B lymphocytes in culture from a patient suffering from MS;

FIG. 5 gives, under the same experimental conditions as in FIG. 4, the assay of the reverse transcriptase activity in the culture of a B lymphocyte line obtained from a control free from MS;

FIG. 6 shows the nucleotide sequence of the clone PSJ17 (SEQ ID NO:9);

FIG. 7 shows the nucleotide sequence SEQ ID NO:8 of the clone designated M003-P004;

FIG. 8 shows the nucleotide sequence SEQ ID NO:2 of the clone F11-1; the portion located between the two arrows in the region of the primer corresponds to a variability imposed by the choice of primer which was used for the cloning of F11-1; in this same figure, the translation into amino acids is shown;

FIG. 9 shows the nucleotide sequence SEQ ID NO:1, and a possible functional reading frame of SEQ ID NO:1 in terms of amino acids; on this sequence, the consensus sequences of the pol gene are underlined;

Figure 4:
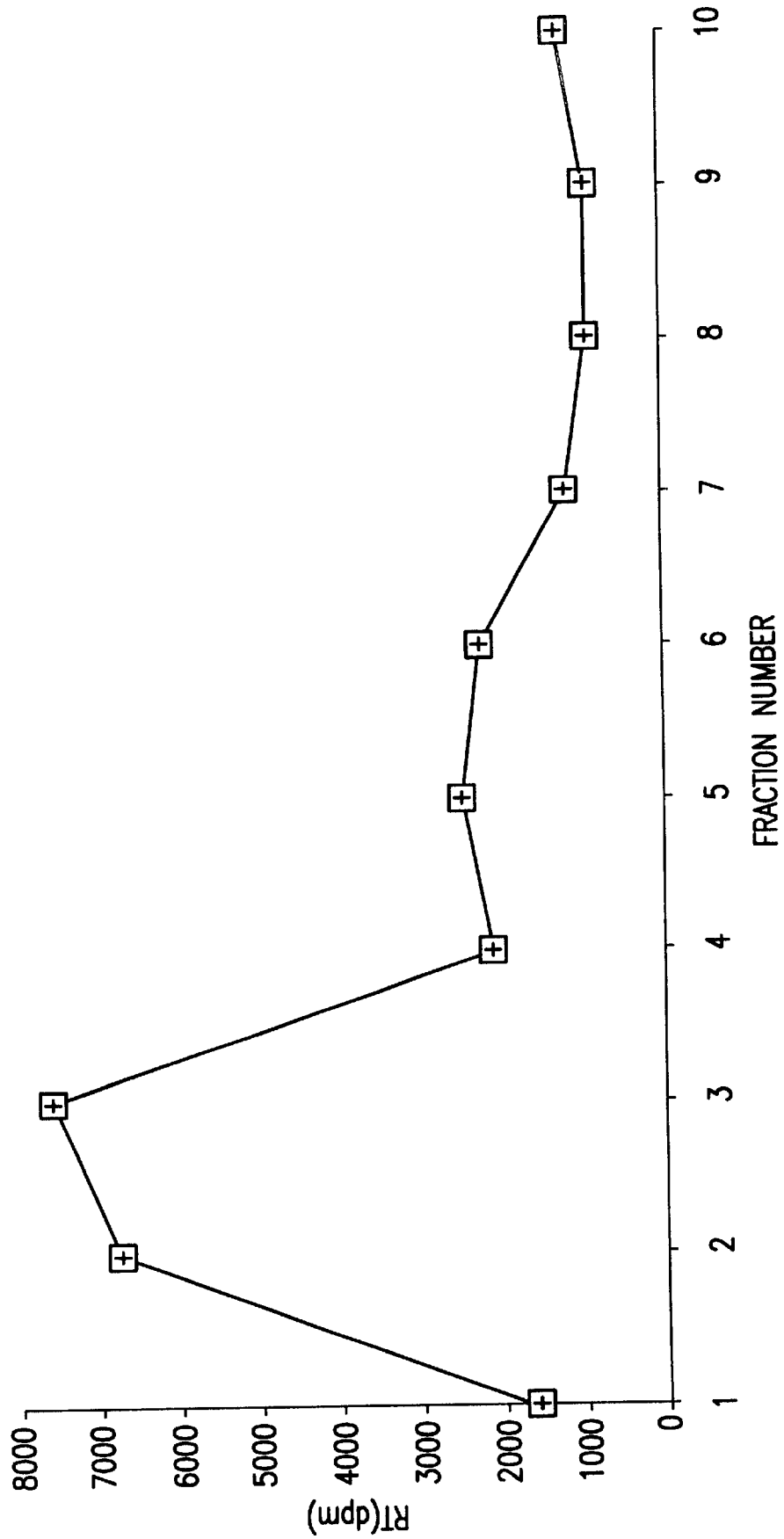
Figure 5:
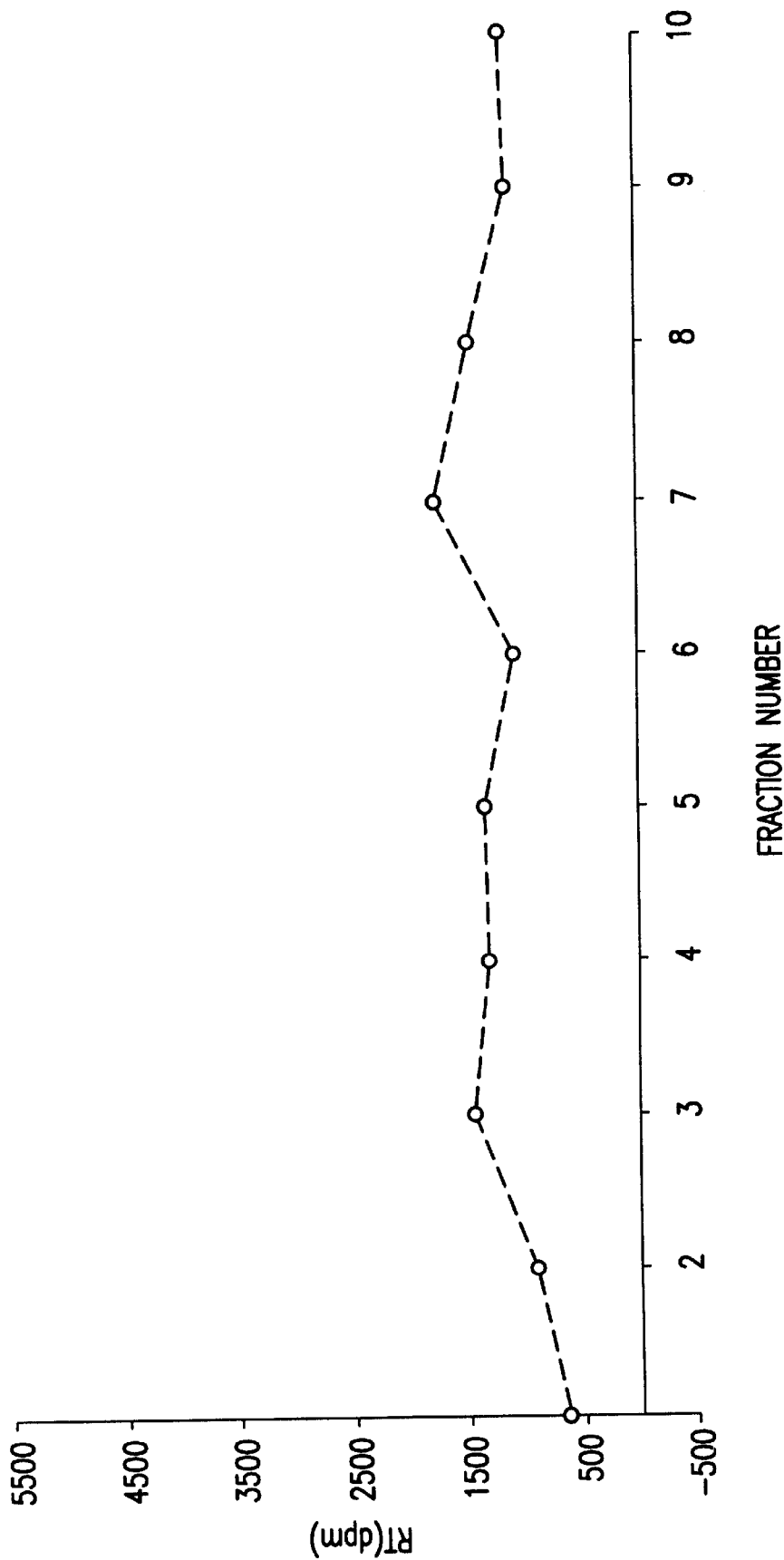
Figure 10:
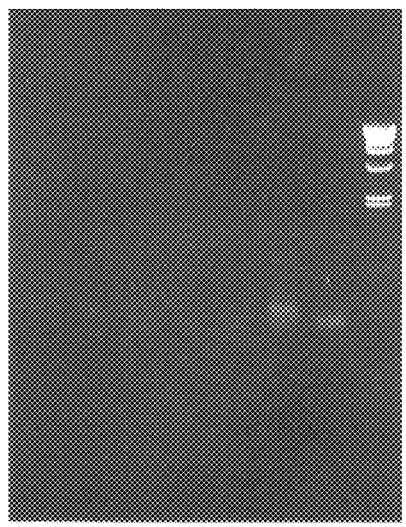
Figure 11:
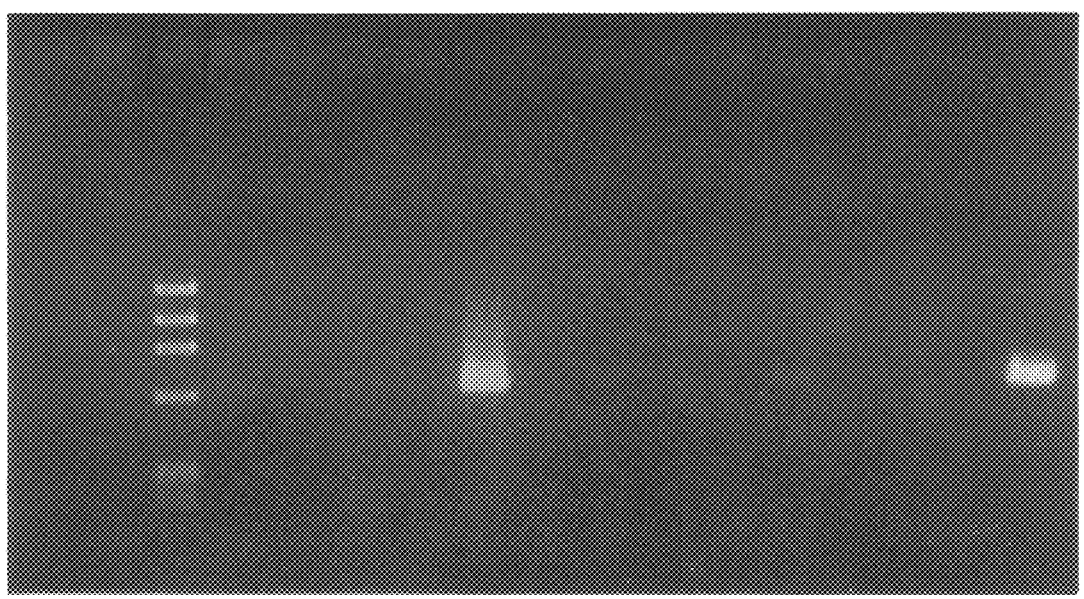
Figure 12:
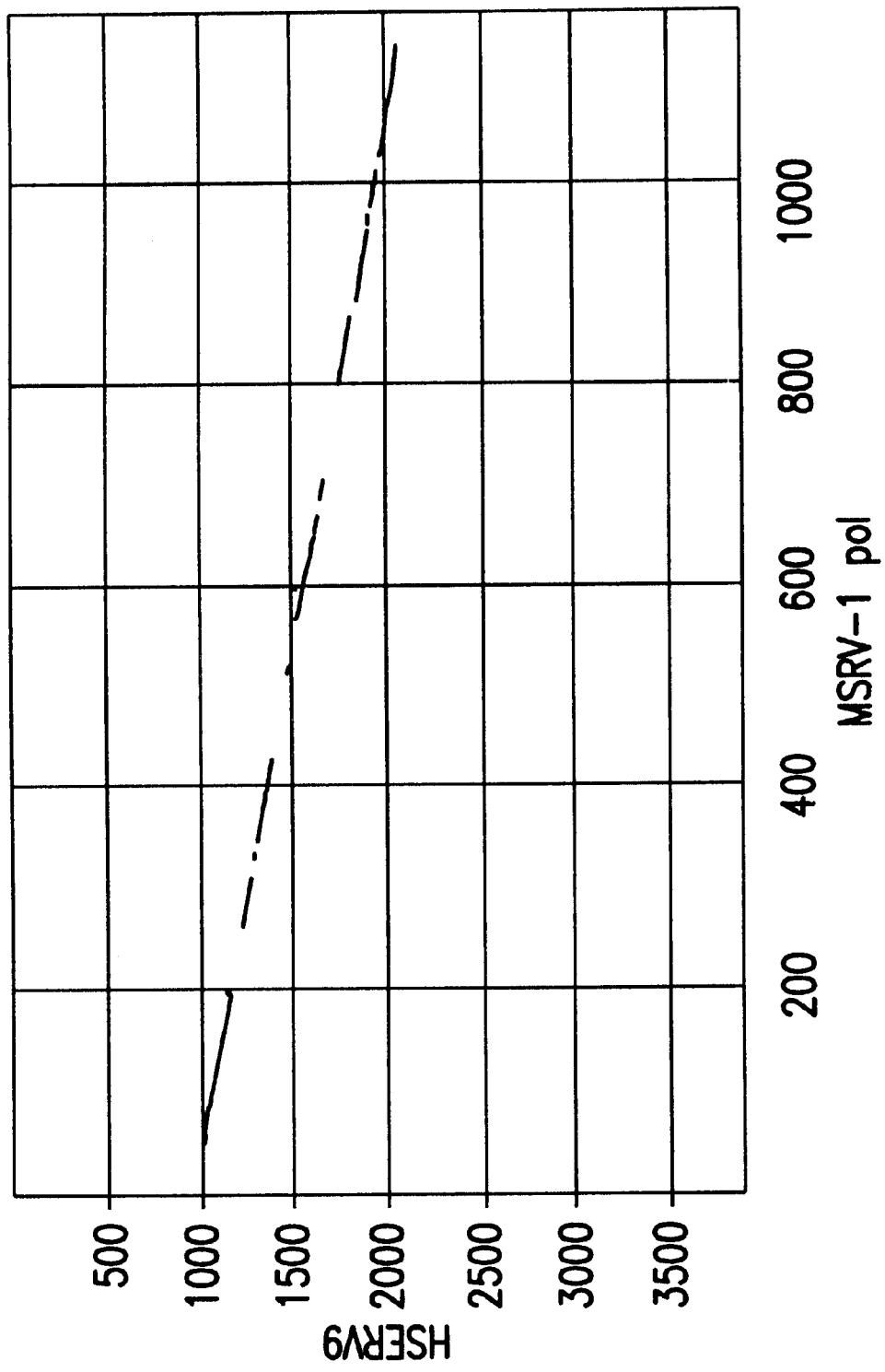
Figure 14:
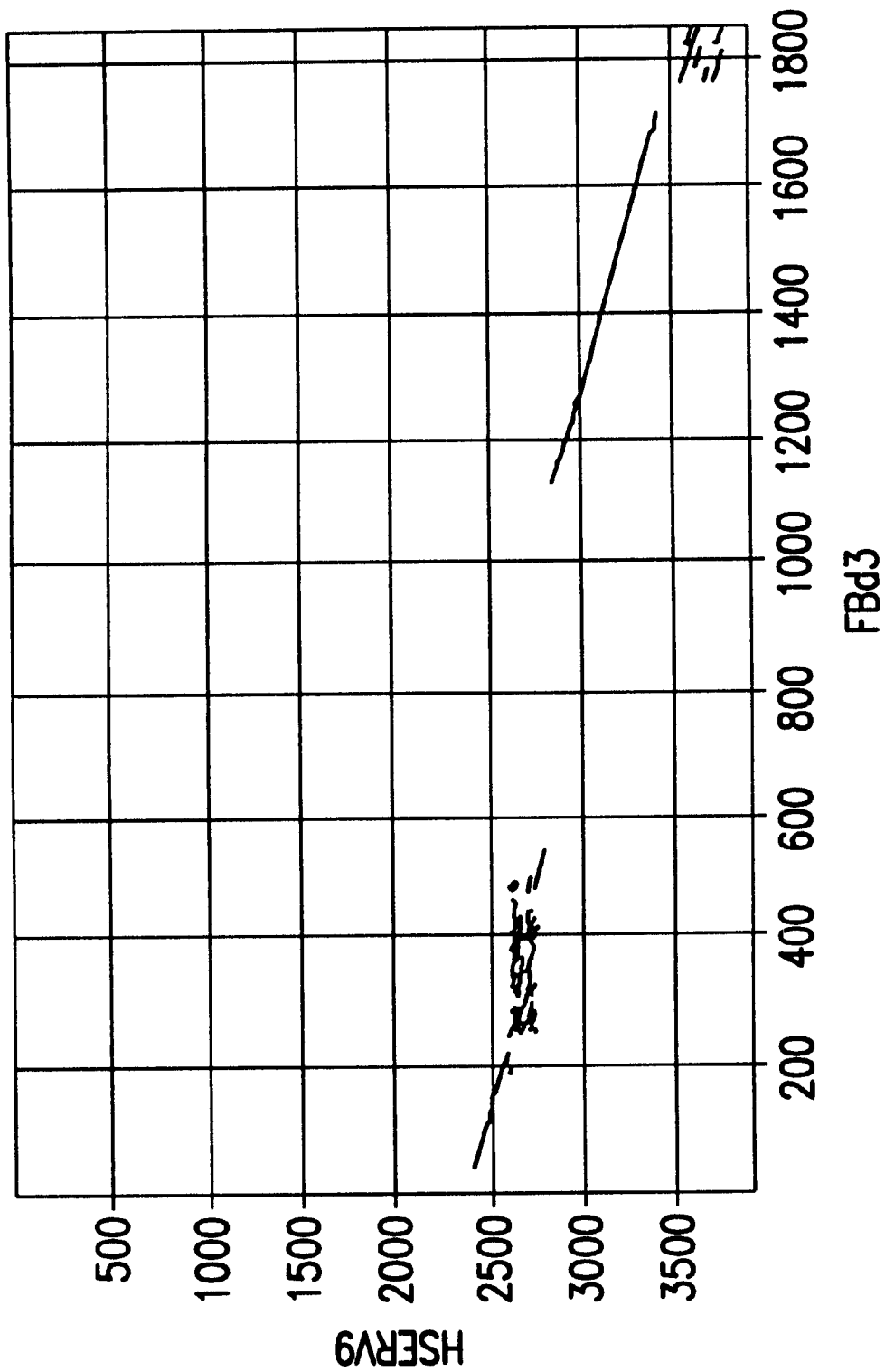
Figure 18:
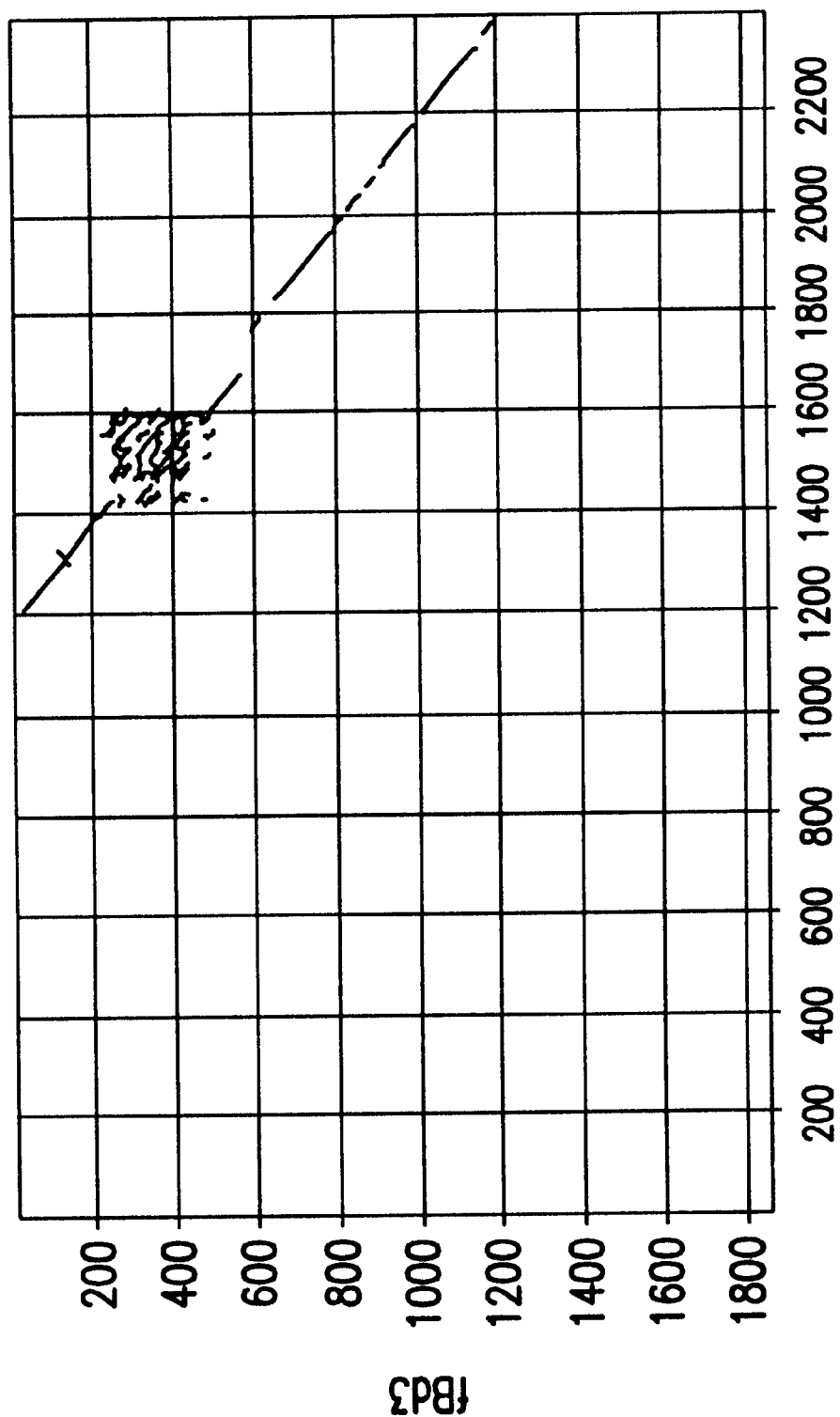
Figure 19:
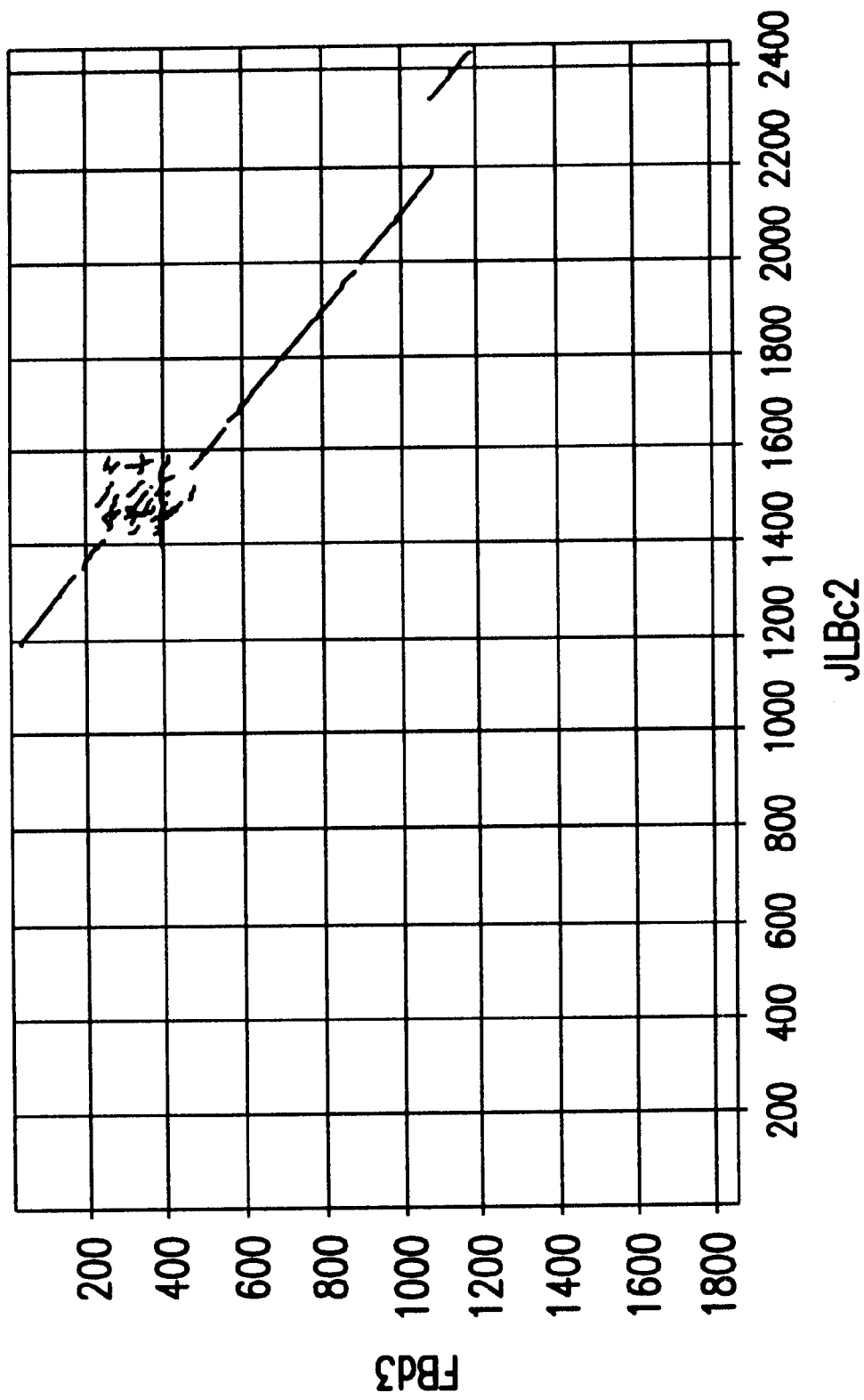
Figure 20:
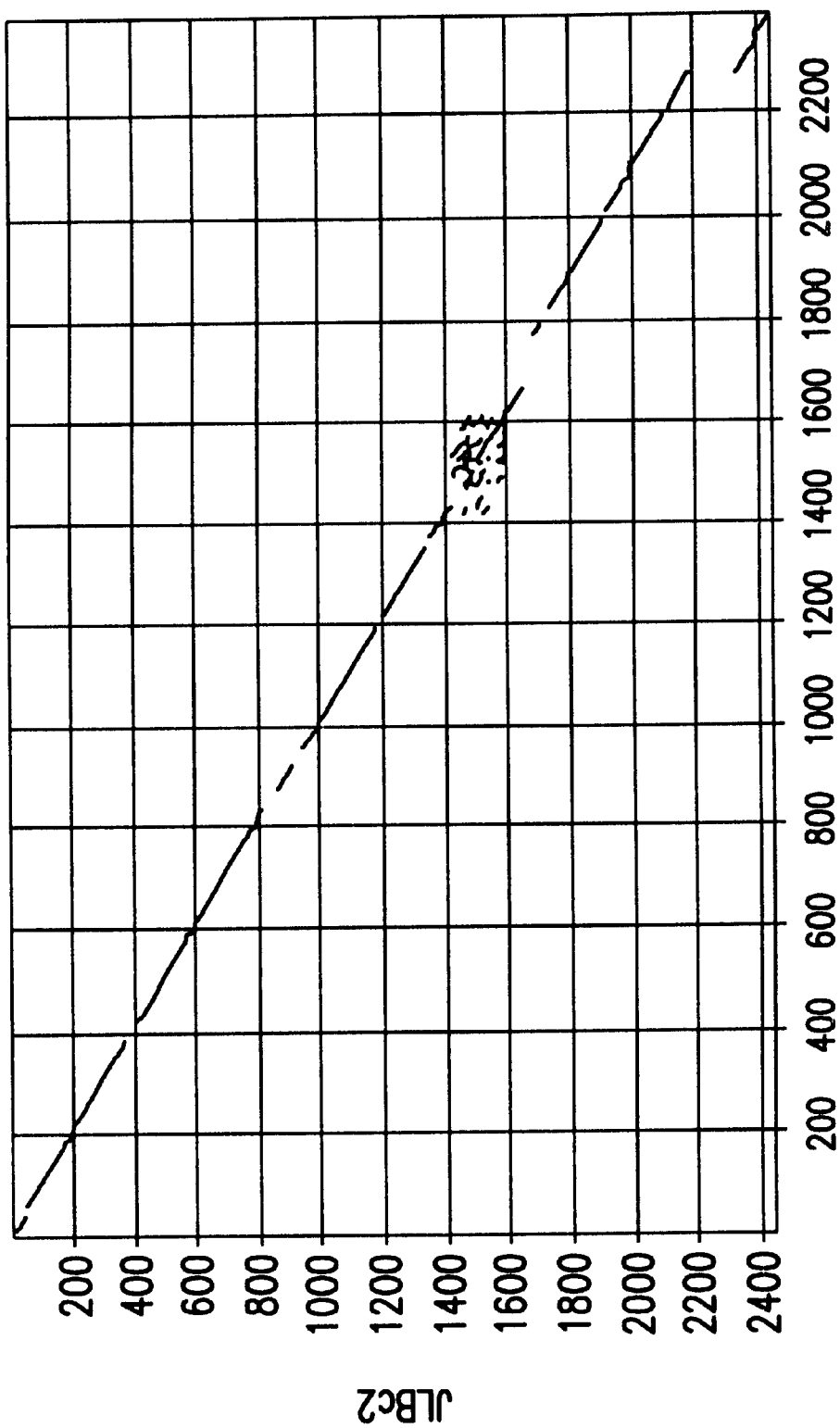
Figure 21:
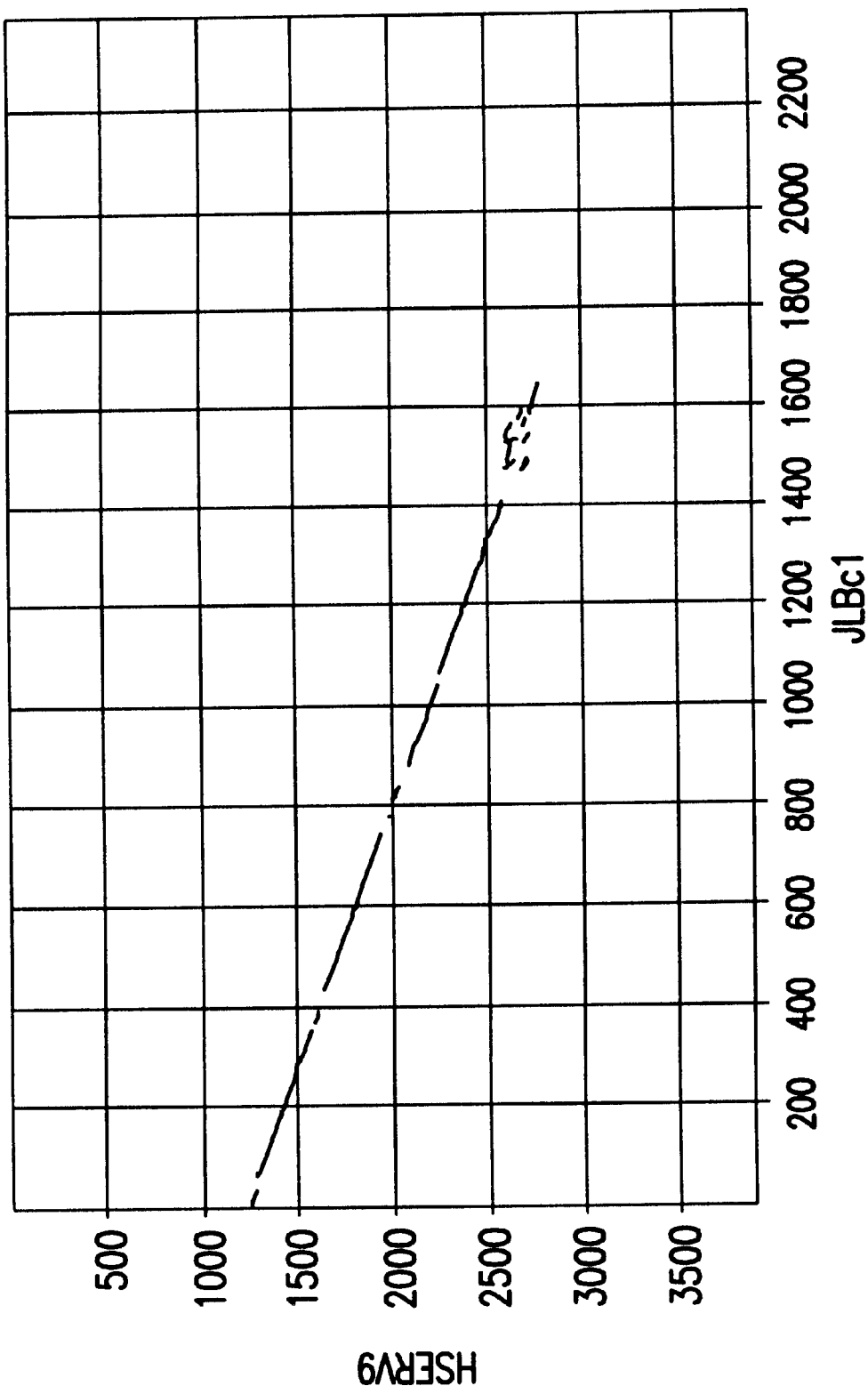
Figure 22:
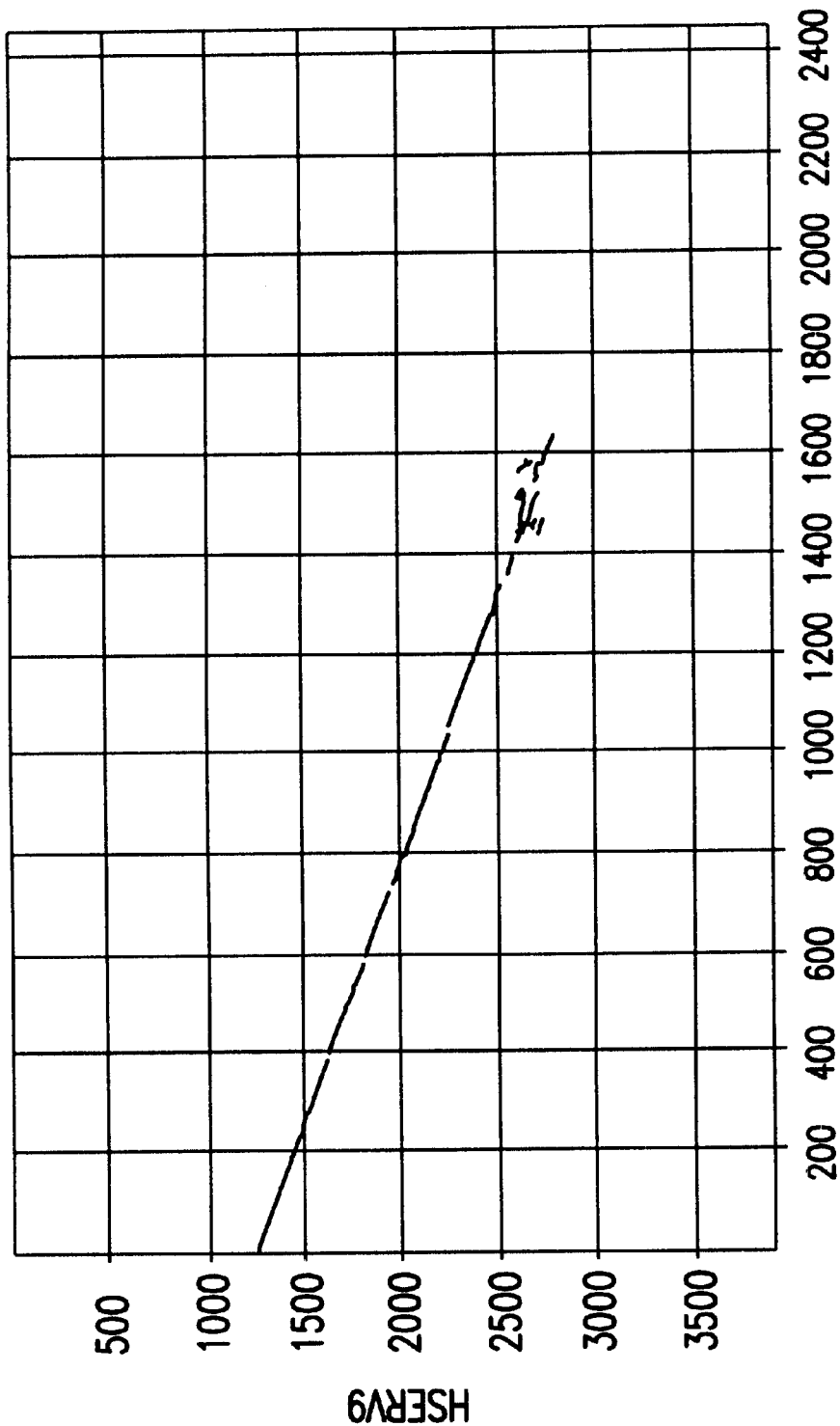
Figure 24:
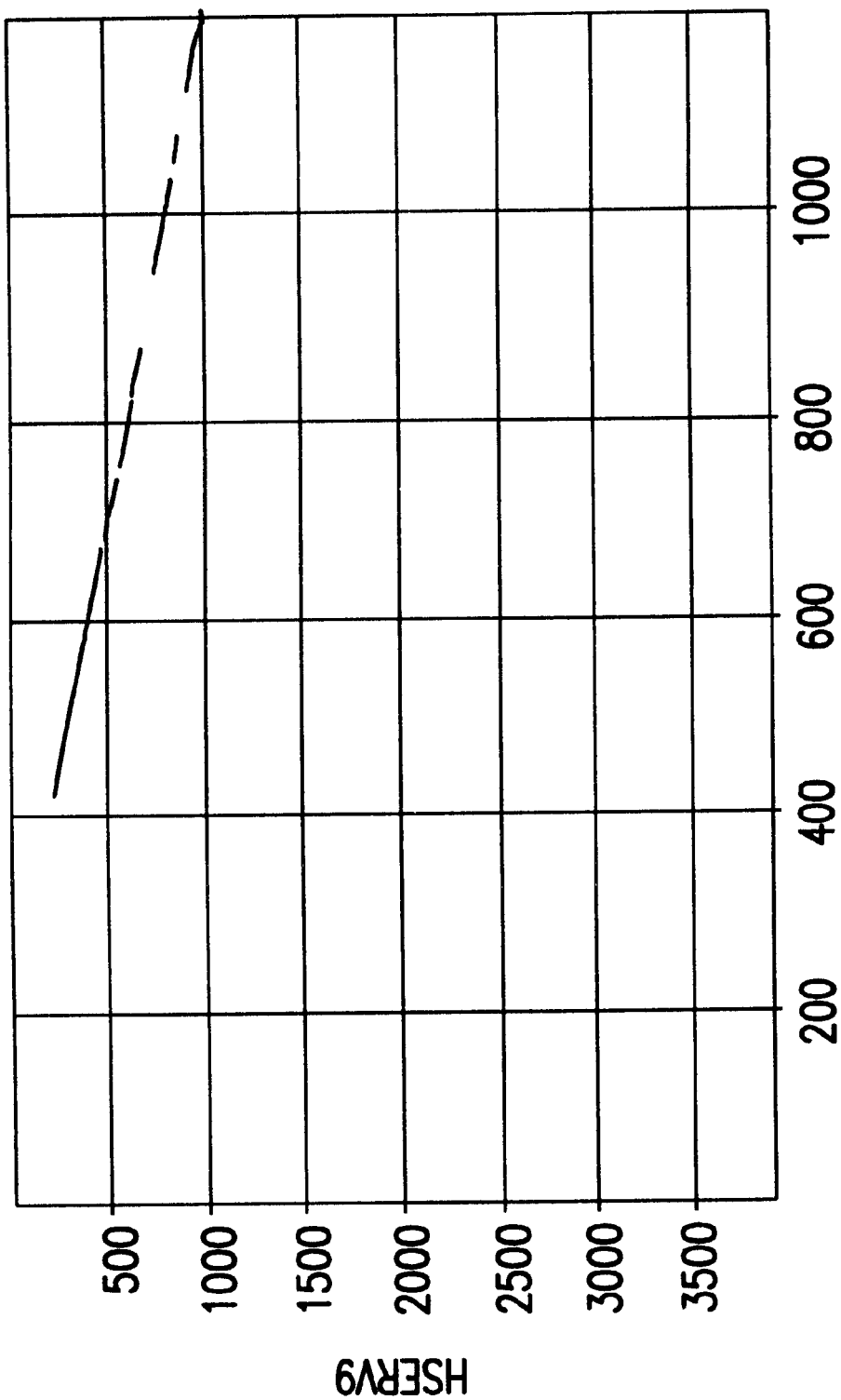
Figure 25:
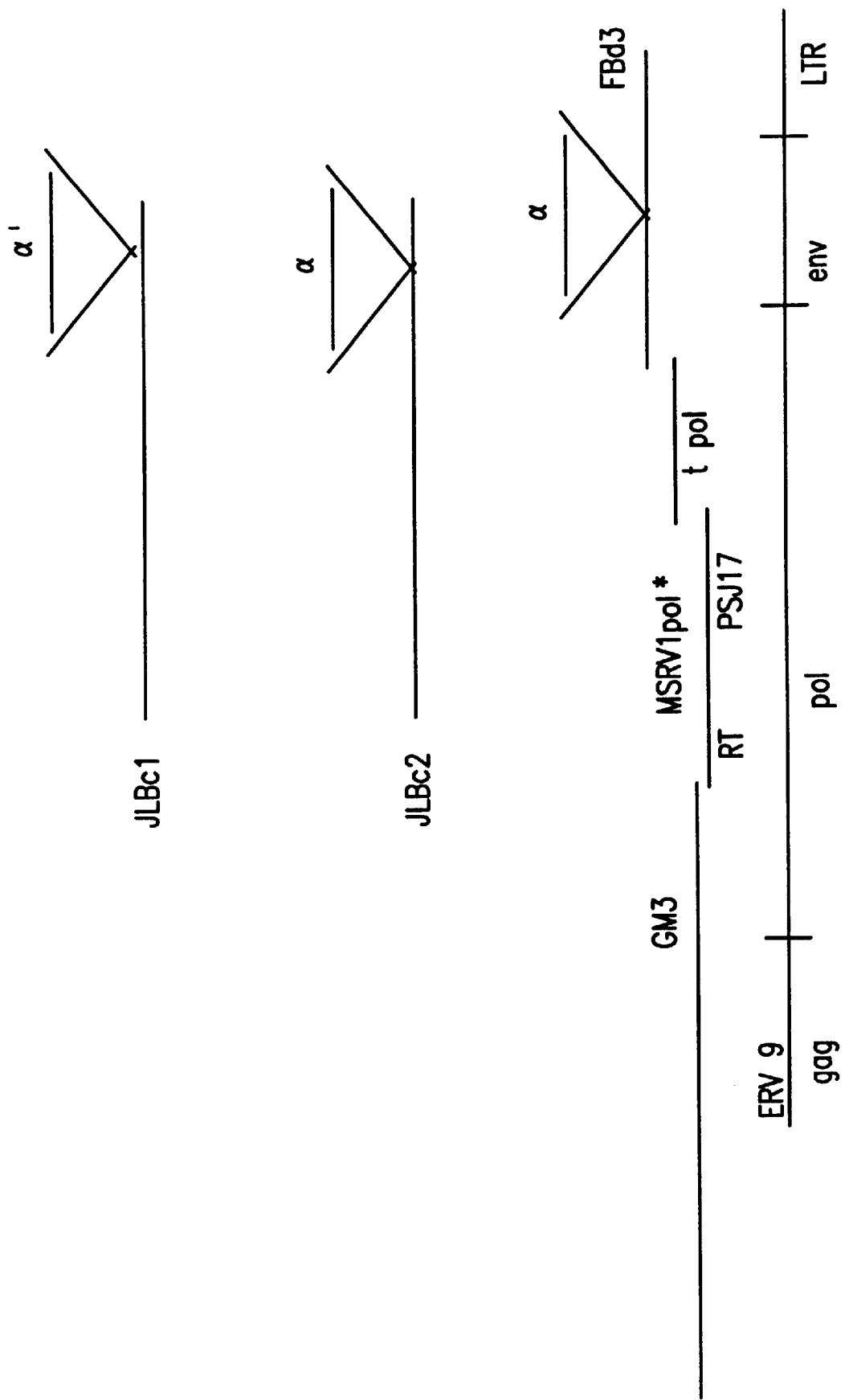
Figure 26:
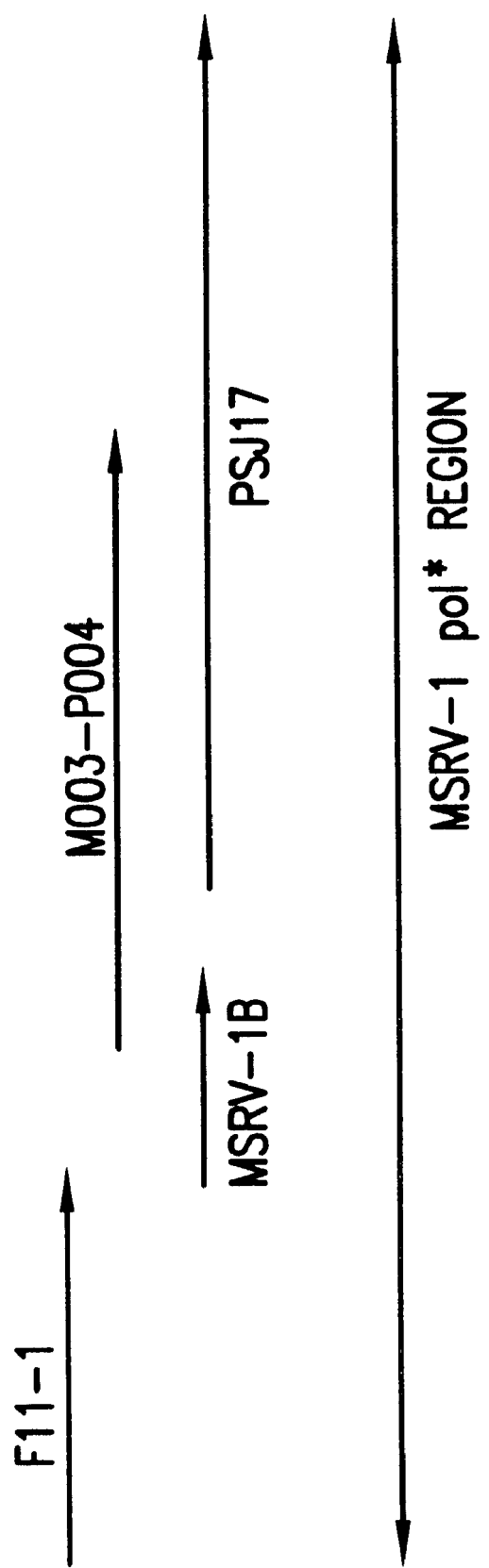
Figure 29:
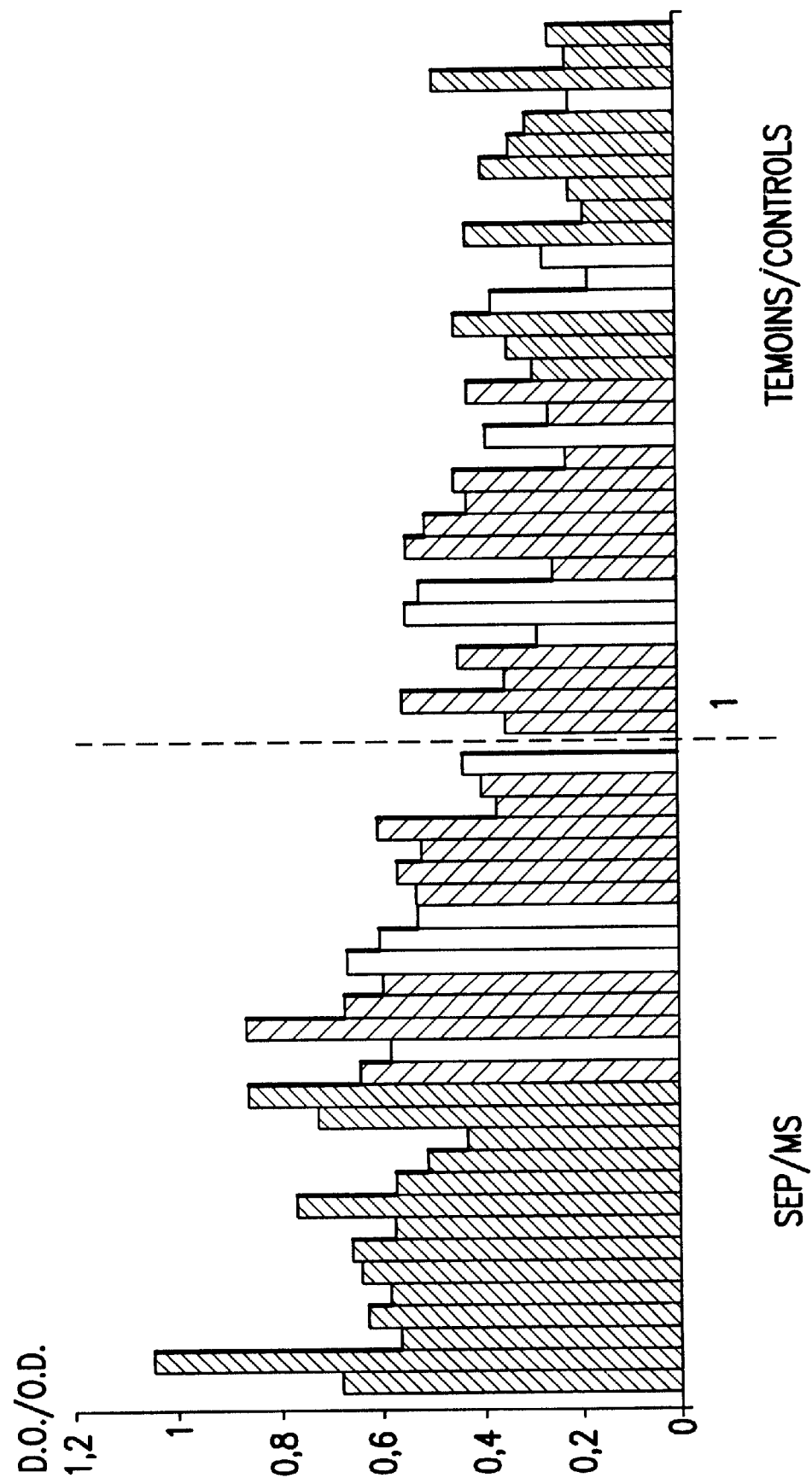
Figure 30:
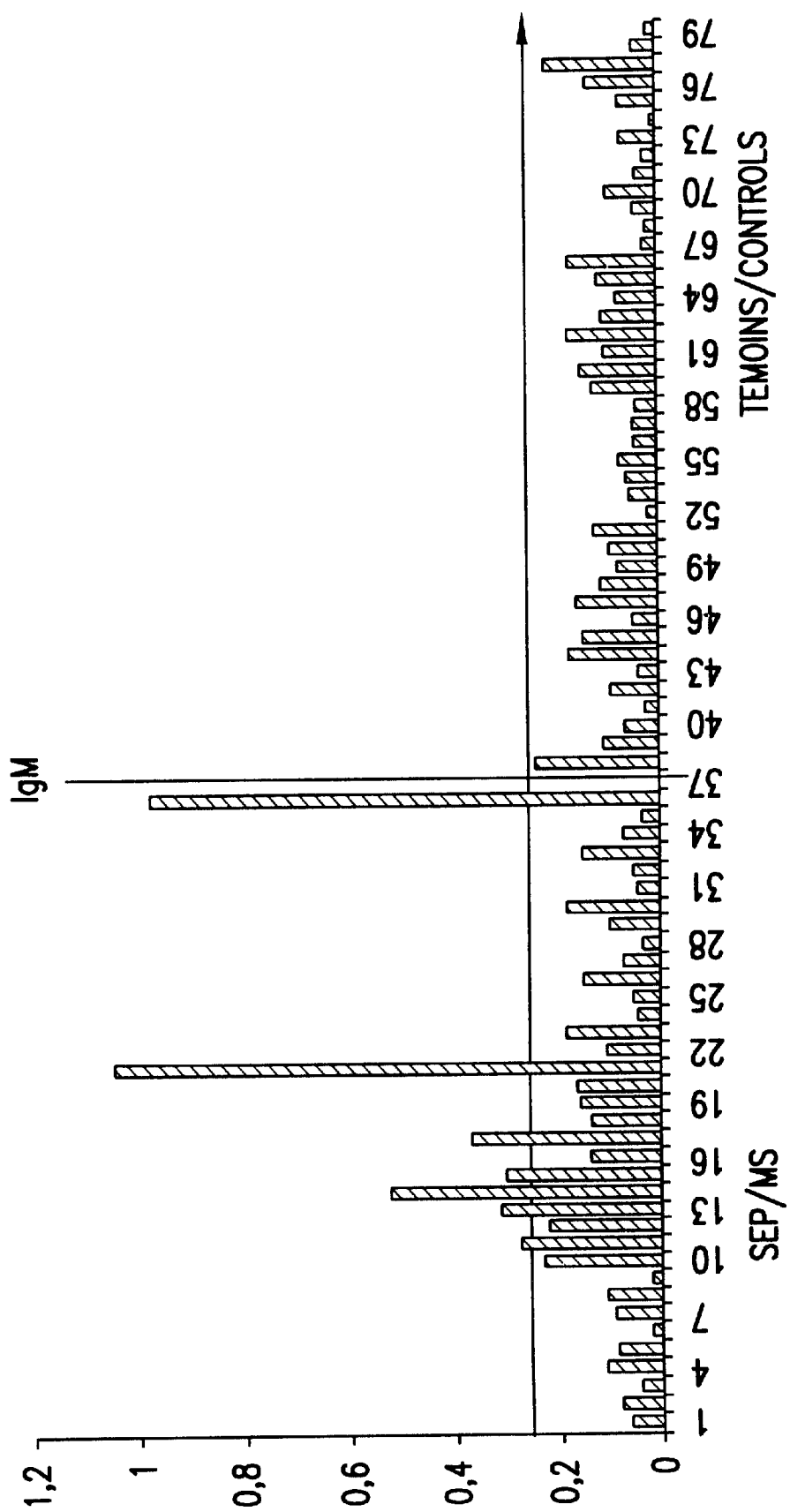
Figure 31:
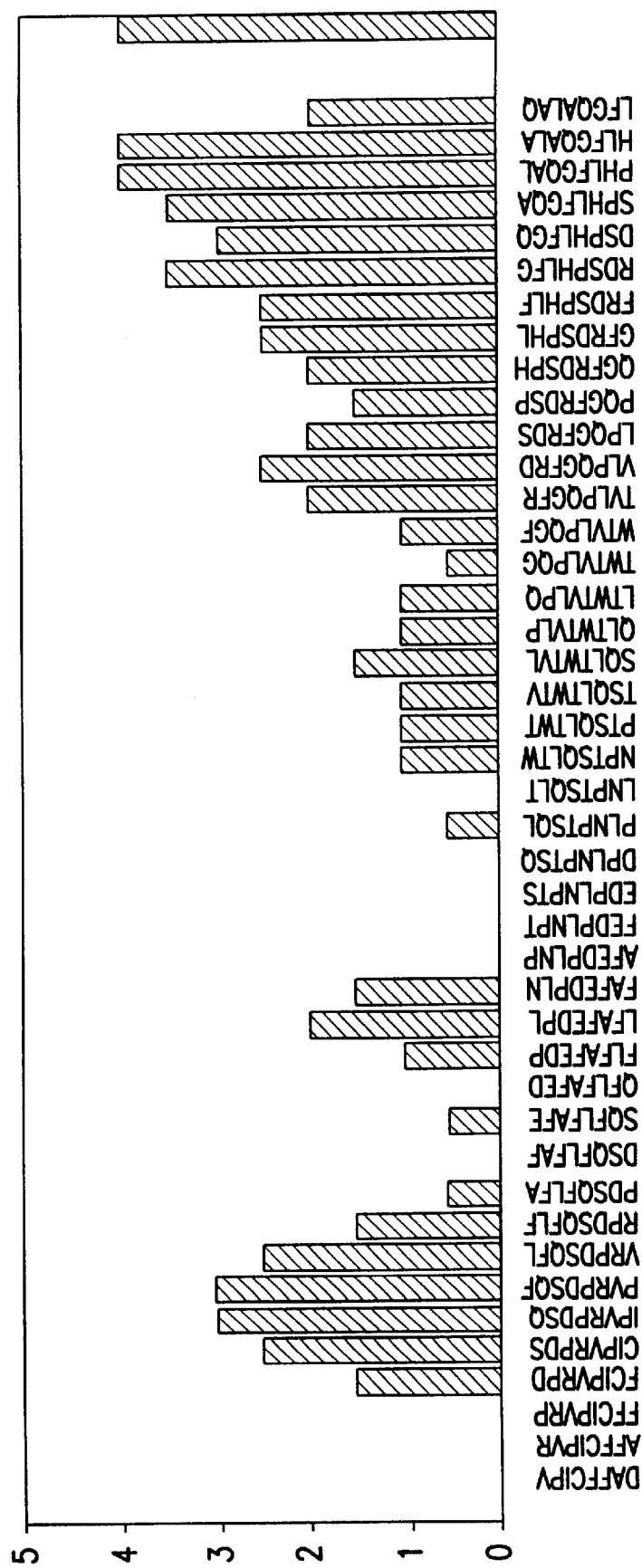
Figure 32:
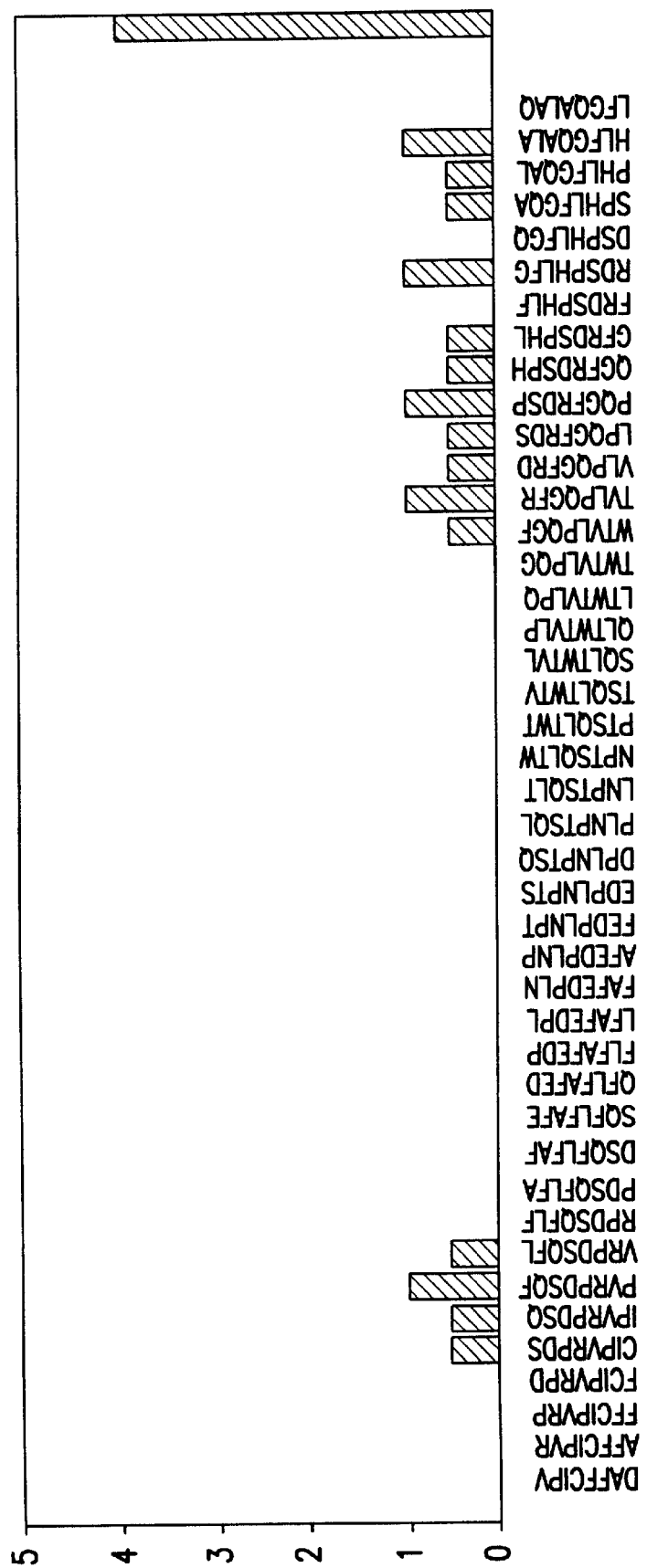
Figure 33:
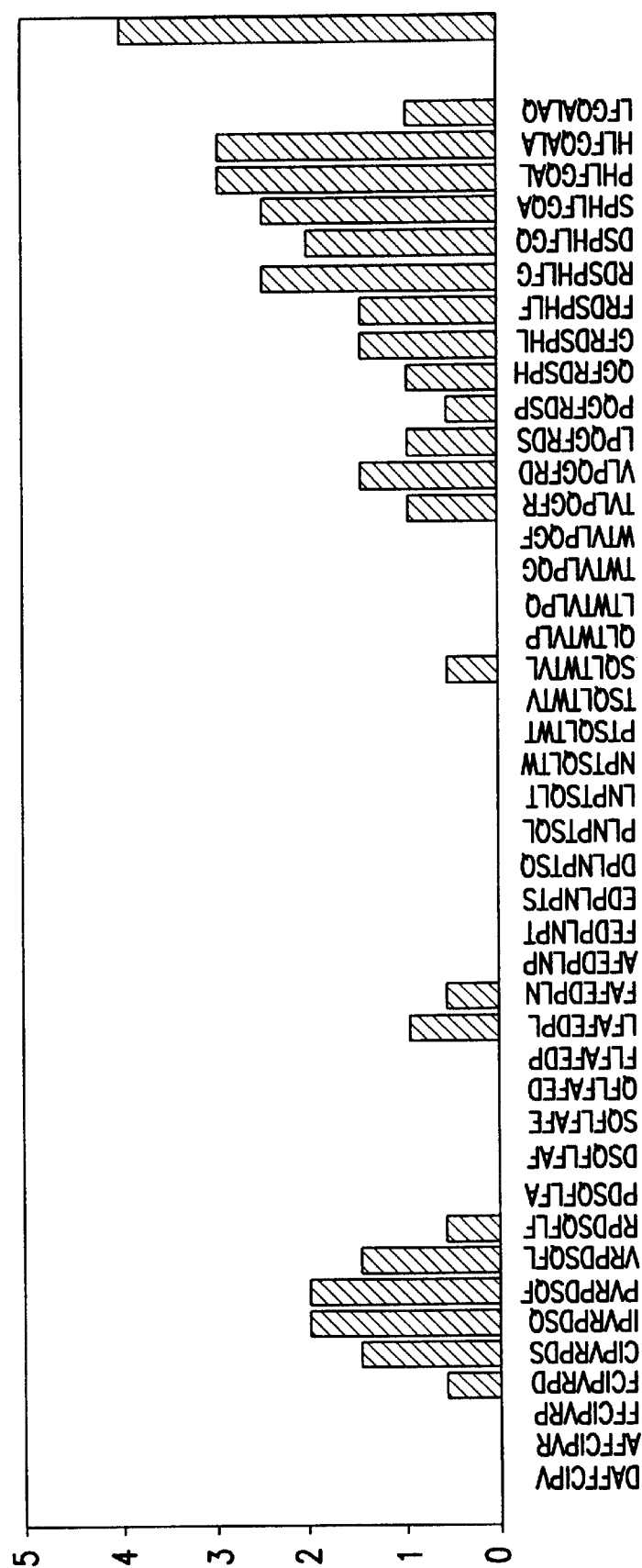
Figure 37:
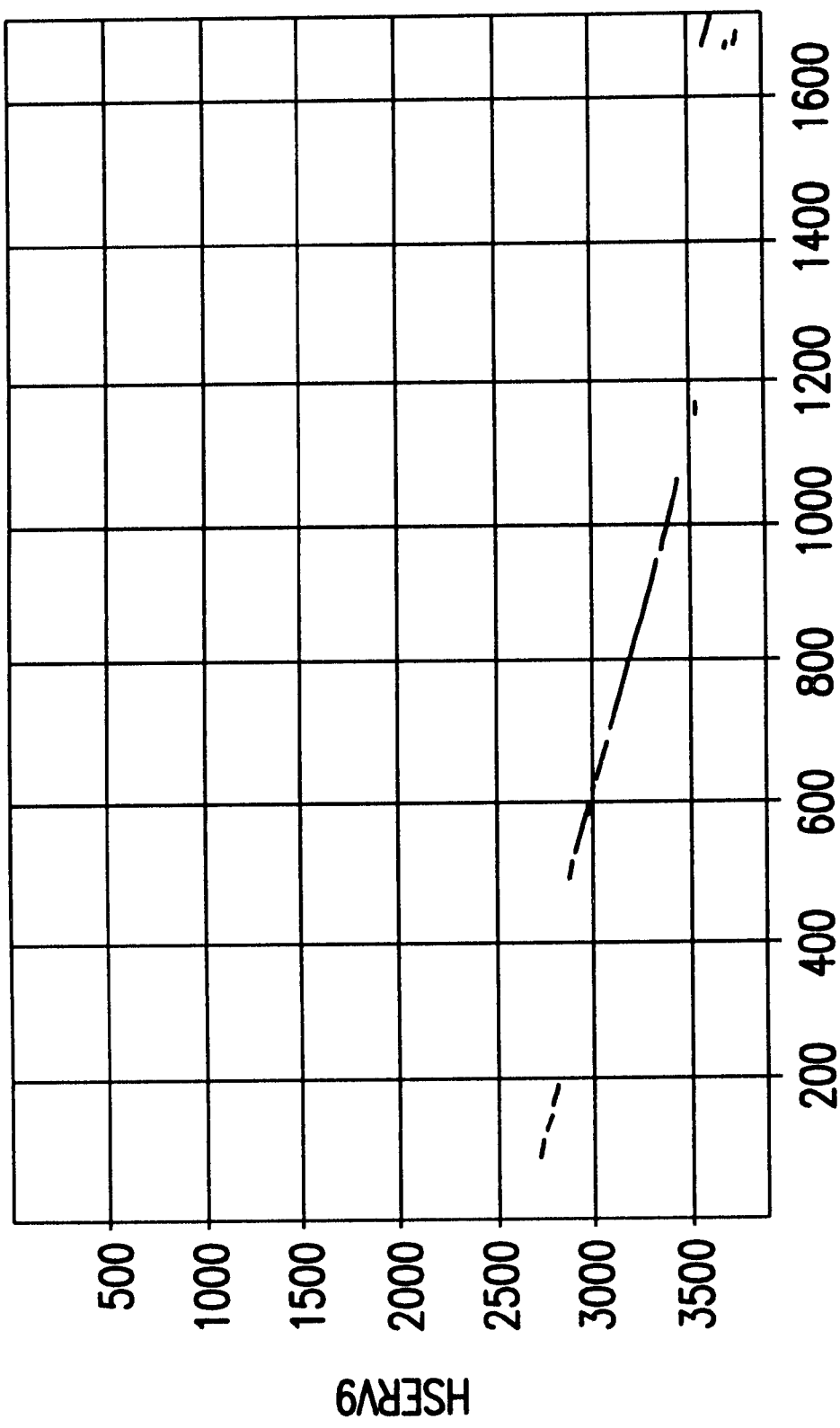
Figure 41:
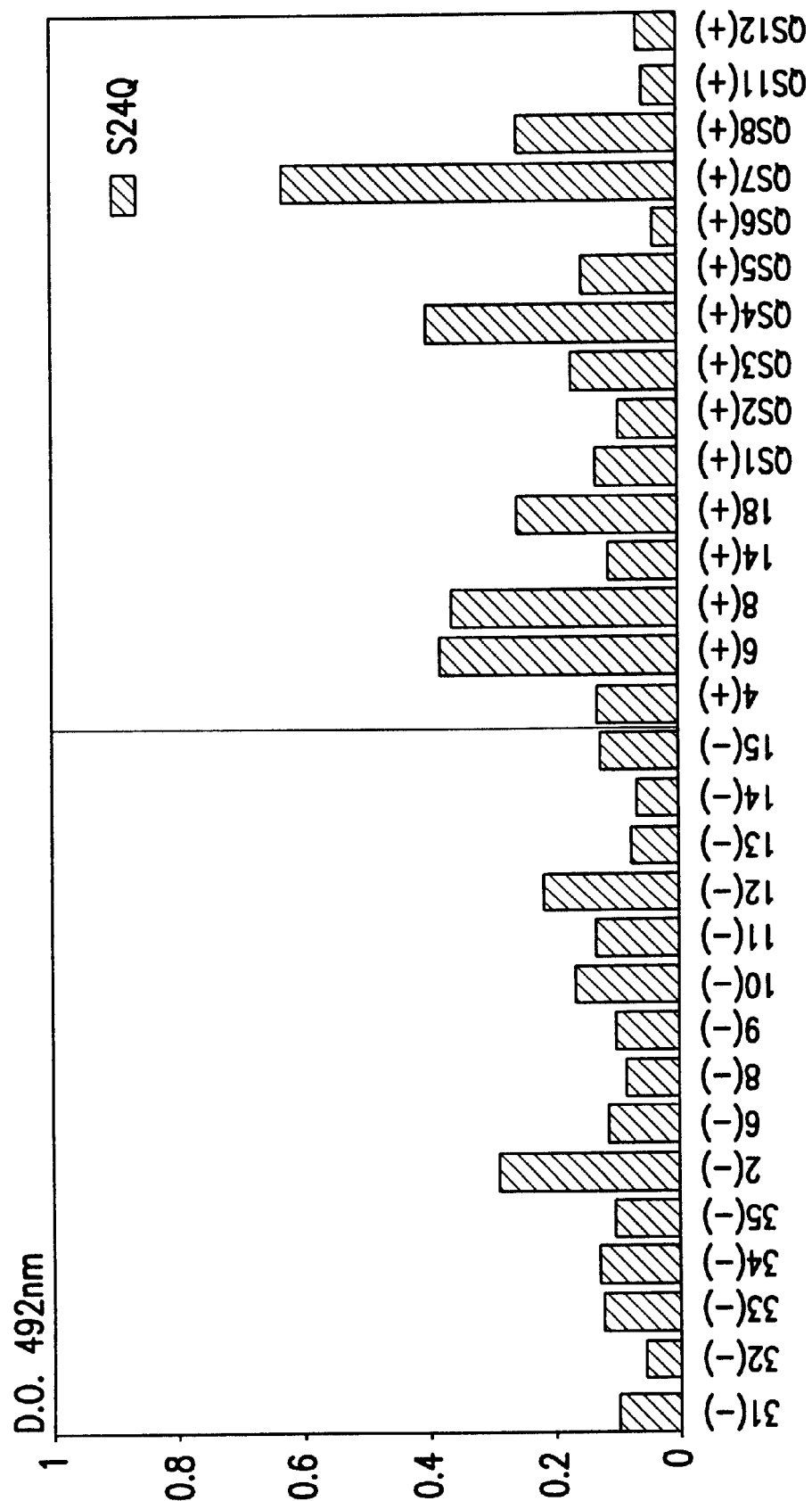
Figure 42:
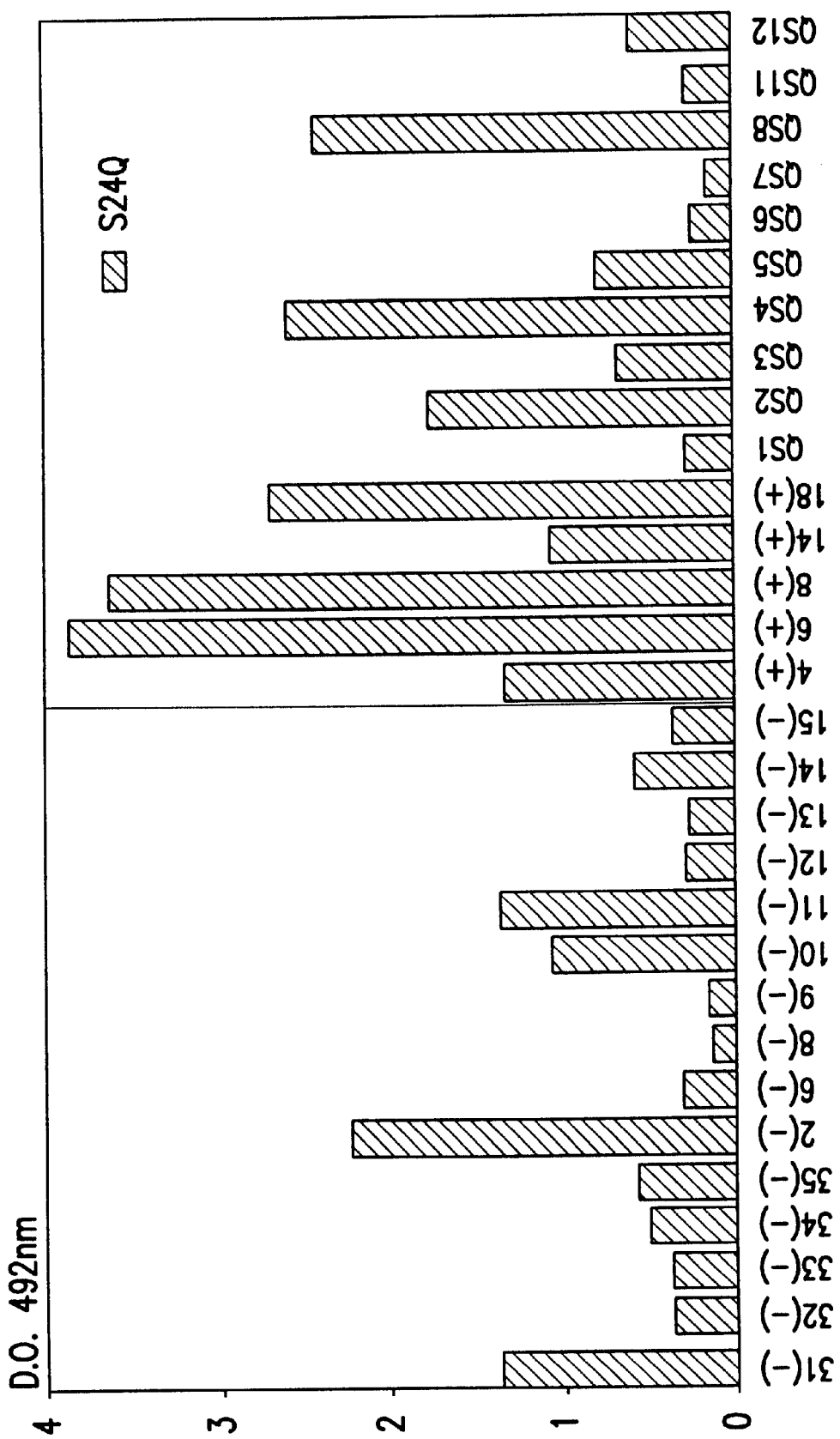

FIGS. 10 and 11 give the results of a PCR, in the form of a photograph under ultraviolet light of an ethidium bromide-impregnated agarose gel, of the amplification products obtained from the primers identified by SEQ ID NO:16, SEQ ID NO:17, SEQ ID NO:18 and SEQ ID NO:19;

FIG. 12 gives a representation in matrix form of the homology between SEQ ID NO:1 of MSRV-1 and that of an endogenous retrovirus designated HSERV9; this homology of at least 65% is demonstrated by a continuous line, the absence of a line meaning a homology of less than 65%;

FIG. 13 shows the nucleotide sequence SEQ ID NO:46 of the clone FBd3;

FIG. 14 shows the sequence homology between the clone FBd3 and the HSERV-9 retrovirus;

FIG. 15 shows the nucleotide sequence SEQ ID NO:51 of the clone t pol;

FIGS. 16 and 17 show, respectively, the nucleotide sequences SEQ ID NO:52 and SEQ ID NO:53 of the clones JLBc1 and JLBc2, respectively;

FIG. 18 shows the sequence homology between the clone JLBc1 and the clone FBd3;

and FIG. 19 the sequence homology between the clone JLBc2 and the clone FBd3;

FIG. 20 shows the sequence homology between the clones JLBc1 and JLBc2;

FIGS. 21 and 22 show the sequence homology between the HSERV-9 retrovirus and the clones JLBc1 and JLBc2, respectively;

FIG. 23 shows the nucleotide sequence SEQ ID NO:56 of the clone GM3;

FIG. 24 shows the sequence homology between the HSERV-9 retrovirus and the clone GM3;

FIG. 25 shows the localization of the different clones studied, relative to the genome of the known retrovirus ERV9;

FIG. 26 shows the position of the clones F11-1, M003-P004, MSRV-1B and PSJ17 in the region hereinafter designated MSRV-1 pol*;

FIG. 27, split into three successive FIGS. 27a, 27b and 27c, shows a possible reading frame covering the whole of the pol gene;

FIG. 28 shows, according to SEQ ID NO:40, the nucleotide sequence coding for the peptide fragment POL2B, having the amino acid sequence identified by SEQ ID NO:39;

FIG. 29 shows the OD values (ELISA tests) at 492 nm obtained for 29 sera of MS patients and 32 sera of healthy controls tested with an anti-IgG antibody;

FIG. 30 shows the OD values (ELISA tests) at 492 nm obtained for 36 sera of MS patients and 42 sera of healthy controls tested with an anti-IgM antibody;

FIGS. 31 to 33 show the results obtained (relative intensity of the spots) for 43 overlapping octapeptides covering the amino acid sequence 61–110, according to the Spotscan technique, respectively with a pool of MS sera, with a pool of control sera and with the pool of MS sera after deduction of a background corresponding to the maximum signal detected on at least one octapeptide with the control serum (intensity=1), on the understanding that these sera were diluted to 1/50. The bar at the far right-hand end represents a graphic scale standard unrelated to the serological test;

FIG. 34 shows the SEQ ID NO:41 and SEQ ID NO:42 of two polypeptides comprising immunodominant [lacuna], while SEQ ID NO:43 and 44 represent immunoreactive polypeptides specific to MS;

FIG. 35 shows the nucleotide sequence SEQ ID NO:59 of the clone LB19 and three potential reading frames of SEQ ID NO:59 in terms of amino acids;

FIG. 36 shows the nucleotide sequence SEQ ID NO:88 (GAG*) and a potential reading frame of SEQ ID NO:88 in terms of amino acids;

FIG. 37 shows the sequence homology between the clone FBd13 and the HSERV-9 retrovirus; according to this representation, the continuous line means a percentage homology greater than or equal to 70% and the absence of a line means a smaller percentage homology;

FIG. 38 shows the nucleotide sequence SEQ ID NO:61 of the clone FP6 and three potential reading frames of SEQ ID NO:61 in terms of amino acids;

FIG. 39 shows the nucleotide sequence SEQ ID NO:89 of the clone G+E+A and three potential reading frames of SEQ ID NO:89 in terms of amino acids;

FIG. 40 shows a reading frame found in the region E and coding for an MSRV-1 retroviral protease identified by SEQ ID NO:90;

FIG. 41 shows the response of each serum of patients suffering from MS, indicated by the symbol (+), and of healthy patients, symbolised by (−), tested with an anti-IgG antibody, expressed as net optical density at 492 nm;

FIG. 42 shows the response of each serum of patients suffering from MS, indicated by the symbols (+) and (QS), and of healthy patients (−), tested with an anti-IgM antibody, expressed as net optical density at 492 nm.

EXAMPLE 1

Obtaining Clones Designated MSRV-1B and MSRV-2B, Defining, Respectively, a Retrovirus MSRV-1 and a Coinfective Agent MSRV2, by "Nested" PCR Amplification of the Conserved pol Regions of Retroviruses on Virion Preparations Originating from the LM7PC and PLI-2 Lines A PCR technique derived from the technique published by Shih (12) was used. This technique enables all trace of contaminant DNA to be removed by treating all the components of the reaction medium with DNase. It concomitantly makes it possible, by the use of different but overlapping primers in two successive series of PCR amplification cycles, to increase the chances of amplifying a cDNA synthesized from an amount of RNA which is small at the outset and further reduced in the sample by the spurious action of the DNAse on the RNA. In effect, the DNase is used under conditions of activity in excess which enable all trace of contaminant DNA to be removed before inactivation of this enzyme remaining in the sample by heating to 85° C. for 10 minutes. This variant of the PCR technique described by Shih (12) was used on a cDNA synthesized from the nucleic acids of fractions of infective particles purified on a sucrose gradient according to the technique described by H. Perron (13) from the "POL-2" isolate (ECACC No. V92072202) produced by the PLI-2 line (ECACC No. 92072201) on the one hand, and from the MS7PG isolate (ECACC No. V93010816) produced by the LM7PC line (ECACC No. 93010817) on the other hand. These cultures were obtained according to the methods which formed the subject of the patent applications published-under Nos WO 93/20188 and WO 93/20189.

After cloning the products amplified by this technique with the TA Cloning Kit® and analysis of the sequence using an Applied Biosystems model 373A Automatic Sequencer, the sequences were analysed using the Geneworks® software on the latest available version of the Genebank® data bank.

The sequences cloned and sequenced from these samples correspond, in particular, to two types of sequence: a first type of sequence, to be found in the majority of the clones (55% of the clones originating from the POL-2 isolates of the PLI-2 culture, and 67% of the clones originating from the MS7PG isolates of the LM7PC cultures), which corresponds to a family of "pol" sequences closely similar to, but different from, the endogenous human retrovirus designated ERV-9 or HSERV-9, and a second type, of sequence which corresponds to sequences very strongly homologous to a sequence attributed to another infective and/or pathogenic agent designated MSRV-2.

The first type of sequence, representing the majority of the clones, consists of sequences whose variability enables four subfamilies of sequences to be defined. These subfamilies are sufficiently similar to one another for it to be possible to consider them to be quasi-species originating from the same retrovirus, as is well known for the HIV-1 retrovirus (14), or to be the outcome of interference with several endogenous pro-viruses coregulated in the producing cells. These more or less defective endogenous elements are sensitive to the same regulatory signals possibly generated by a replicative provirus, since they belong to the same family of endogenous retroviruses (15). This new family of endogenous retroviruses, or alternatively this new retroviral species from which the generation of quasi-species has been obtained in culture, and which contains a consensus of the sequences described below, is designated MSRV-1B.

FIG. 1 presents the general consensus sequences of the sequences of the different MSRV-1B clones sequenced in this experiment, these sequences being identified, respectively, by SEQ ID NO:3, SEQ ID NO:4, SEQ ID NO:5 and SEQ ID NO:6. These sequences display a homology with respect to nucleic acids ranging from 70% to 88% with the HSERV9 sequence referenced X57147 and M37638 in the Genebankr data base. Four "consensus" nucleic acid sequences representative of different quasi-species of a possibly exogenous retrovirus MSRV-1B, or of different subfamilies of an endogenous retrovirus MSRV-1B, have been defined. These representative consensus sequences are presented in FIG. 2, with the translation into amino acids. A functional reading frame exists for each subfamily of these MSRV-1B sequences, and it can be seen that the functional open reading frame corresponds in each instance to the amino acid sequence appearing on the second line under the nucleic acid sequence. The general consensus of the MSRV-1B sequence, identified by SEQ ID NO:7 and obtained by this PCR technique in the "pol" region, is presented in FIG. 1.

The second type of sequence representing the majority of the clones sequenced is represented by the sequence MSRV-2B presented in FIG. 3 and identified by SEQ ID NO:11. The differences observed in the sequences corresponding to the PCR primers are explained by the use of degenerate primers in mixture form used under different technical conditions.

The MSRV-2B sequence (SEQ ID NO:11) is sufficiently divergent from the retroviral sequences already described in the data banks for it to be suggested that the sequence region in question belongs to a new infective agent, designated MSRV-2. This infective agent would, in principle, on the basis of the analysis of the first sequences obtained, be related to a retrovirus but, in view of the technique used for obtaining this sequence, it could also be a DNA virus whose genome codes for an enzyme which incidentally possesses reverse transcriptase activity, as is the case, for example, with the hepatitis B virus, HBV (12). Furthermore, the random nature of the degenerate primers used for this PCR amplification technique may very well have permitted, as a result of unforeseen sequence homologies or of conserved sites in the gene for a related enzyme, the amplification of a nucleic acid originating from a prokaryotic or eukaryotic pathogenic and/or coinfective agent (protist).

EXAMPLE 2

Obtaining Clones Designated MSRV-1B and MSRV-2B, Defining a Family MSRV-1 and MSRV2, by "Nested" PCR Amplification of the Conserved pol Regions of Retroviruses on Preparations of B Lymphocytes from a New Case of MS The same PCR technique, modified according to the technique of Shih (12), was used to amplify and sequence the RNA nucleic acid material present in a purified fraction of virions at the peak of "LM7-like" reverse transcriptase activity on a sucrose gradient according to the technique described by H. Perron (13), and according to the protocols mentioned in Example 1, from a spontaneous lymphoblastoid line obtained by self-immortalization in culture of B lymphocytes from an MS patient who was seropositive for the Epstein-Barr virus (EBV), after setting up the blood lymphoid cells in culture in a suitable culture medium containing a suitable concentration of cyclosporin A. A representation of the reverse transcriptase activity in the sucrose fractions taken from a purification gradient of the virions produced by this line is presented in FIG. 4. Similarly, the culture supernatants of a B line obtained under the same conditions from a control free from MS were treated under the same conditions, and the assay of reverse transcriptase activity in the sucrose gradient fractions proved negative throughout (background), and is presented in FIG. 5. Fraction 3 of the gradient corresponding to the MS B line and the same fraction without reverse transcriptase activity of the non-MS control gradient were analysed by the same RT-PCR technique as before, derived from Shih (12), followed by the same steps of cloning and sequencing as described in Example 1.

It is particularly noteworthy that the MSRV-1 and MSRV-2 type sequences are to be found only in the material associated with a peak of "LM7-like" reverse transcriptase activity originating from the MS B lymphoblastoid line. These sequences were not to be found with the material from the control (non-MS) B lymphoblastoid line in 26 recombinant clones taken at random. Only Mo-MuLV type contaminant sequences, originating from the commercial reverse transcriptase used for the cDNA synthesis step, and sequences without any particular retroviral analogy were to be found in this control, as a result of the "consensus" amplification of homologous polymerase sequences which is produced by this PCR technique. Furthermore, the absence of a concentrated target which competes for the amplification reaction in the control sample permits the amplification of dilute contaminants. The difference in results is manifestly highly significant (chi-squared, $p<0.001$).

EXAMPLE 3

Obtaining a Clone PSJ17, Defining a Retrovirus MSRV-1, by Reaction of Endogenous Reverse Transcriptase with a Virion Preparation Originating from the PLI-2 Line This approach is directed towards obtaining reverse-transcribed DNA sequences from the supposedly retroviral RNA in the isolate using the reverse transcriptase activity present in this same isolate. This reverse transcriptase activity can theoretically function only in the presence of a retroviral RNA linked to a primer tRNA or hybridized with short strands of DNA already reverse-transcribed in the retroviral particles (16). Thus, the obtaining of specific retroviral sequences in a material contaminated with cellular nucleic acids was optimized according to these authors by means of the specific enzymatic amplification of the portions of viral RNAs with a viral reverse transcriptase activity. To this end, the authors determined the particular physicochemical conditions under which this enzymatic activity of reverse transcription on RNAs contained in virions could be effective in vitro. These conditions correspond to the technical description of the protocols presented below (endogenous RT reaction, purification, cloning and sequencing).

The molecular approach consisted in using a preparation of concentrated but unpurified virion obtained from the culture supernatants of the PLI-2 line, prepared according to the following method: the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g (or 30,000 rpm in a type 45 T LKB-HITACHI rotor) for 2 h at 4° C. After removal of the supernatant, the sedimented pellet is taken up in a small volume of PBS and constitutes the fraction of concentrated but unpurified virion. This concentrated but unpurified viral sample was used to perform a so-called endogenous reverse transcription reaction, as described below.

A volume of 200 $\mu$l of virion purified according to the protocol described above, and containing a reverse transcriptase activity of approximately 1–5 million dpm, is thawed at 37° C. until a liquid phase appears, and then placed on ice. A 5-fold concentrated buffer was prepared with the following components: 500 mM Tris-HCl pH 8.2; 75 mM NaCl; 25 mM MgCl2; 75 mM DTT and 0.10% NP 40; 100 $\mu$l of 5×buffer+25 $\mu$l of a 100 mM solution of dATP+25 ml of a 100 mM solution of dTTP+25 ml of a 100 $\mu$M solution of dGTP+25 $\mu$l of a 100 mM solution of dCTP+100 ml of sterile distilled water+200 ml of the virion suspension (RT activity of 5 million DPM) in PBS were mixed and incubated at 42° C. for 3 hours. After this incubation, the reaction mixture is added directly to a buffered phenol/-chloroform/isoamyl alcohol mixture (Sigma ref. P 3803); the aqueous phase is collected and one volume of sterile distilled water is added to the organic phase to re-extract the residual nucleic acid material. The collected aqueous phases are combined, and the nucleic acids contained are precipitated by adding 3M sodium acetate pH 5.2 to 1/10 volume+2 volumes of ethanol+1 $\mu$l of glycogen (Boehringer-Mannheim ref. 901 393) and placing the sample at −20° C. for 4 h or overnight at +4° C. The precipitate obtained after centrifugation is then washed with 70% ethanol and resuspended in 60 ml of distilled water. The products of this reaction were then purified, cloned and sequenced according to the protocol which will now be described: blunt-ended DNAs with. unpaired adenines at the ends were generated: a "filling-in" reaction was first performed: 25 $\mu$l of the previously purified DNA solution were mixed with 2 $\mu$l of a 2.5 mM solution containing, in equimolar amounts, dATP+dGTP+dTTP+dCTP/1 $\mu$l of T4 DNA polymerase (Boehringer-Manmheim ref. 1004 786)/5 $\mu$l of 10×"incubation buffer for restriction enzyme" (Boehringer-Mannheim ref. 1417 975)/1 $\mu$l of a 1% bovine serum albumin solution/16 $\mu$l of sterile distilled water. This mixture was incubated for 20 minutes at 11° C. 50 $\mu$l of TE buffer and 1 $\mu$l of glycogen (Boehringer-Mannheim ref. 901 393) were added thereto before extraction of the nucleic acids with phenol/chloroform/isoamyl alcohol (Sigma ref. P 3803) and precipitation with sodium acetate as described above. The DNA precipitated after centrifugation is resuspended in 10 μl of 10 mM Tris buffer pH 7.5. 5 μl of this suspension were then mixed with 20 μl of 5×Taq buffer, 20 μl of 5 mM dATP, 1 μl (5U) of Taq DNA polymerase (Amplitaq™) and 54 μl of sterile distilled water. This mixture is incubated for 2 h at 75° C. with a film of oil on the surface of the solution. The DNA suspended in the aqueous solution drawn off under the film of oil after incubation is precipitated as described above and-resuspended in 2 μl of sterile distilled water. The DNA obtained was inserted into a plasmid using the TA Cloning™ kit. The 2 μl of DNA solution were mixed with 5 μl of sterile distilled water, 1 μl of a 10-fold concentrated ligation buffer "10×LIGATION BUFFER", 2 μl of "pCR™ VECTOR" (25 ng/ml) and 1 μl of "TA DNA LIGASE". This mixture was incubated overnight at 12° C. The following steps were carried out according to the instructions of the TA Cloning® kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analysed on agarose gel. Plasmids possessing an insert detected under UV light after staining the gel with ethidium bromide were selected for sequencing of the insert, after hybridization with a primer complementary to the Sp6 promoter present on the cloning plasmid of the TA cloning kit®. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

Discriminating analysis on the computerized data banks of the sequences cloned from the DNA fragments present in the reaction mixture enabled a retroviral type sequence to be revealed. The corresponding clone PSJ17 was completely sequenced, and the sequence obtained, presented in FIG. 6 and identified by SEQ ID No. 9, was analysed using the "Geneworks®" software on the updated "Genebank®" data banks. An identical sequence already described could not be found by analysis of the data banks. Only a partial homology with some known retroviral elements was to be found. The most useful relative homology relates to an endogenous retrovirus designated ERV-9, or HSERV-9, according to the references (18).

EXAMPLE 4

PCR Amplification of the Nucleic Acid Sequence Contained Between the 5' Region Defined by the Clone "pol MSRV-1B" and the 3' Region Defined by the Clone PSJ17

Five oligonucleotides, M001, M002-A, M003-BCD, P004 and P005, were defined in order to amplify the RNA originating from purified POL-2 virions. Control reactions were performed so as to check for the presence of contaminants (reaction with water). The amplification consists of an RT-PCR step according to the protocol described in Example 2, followed by a "nested" PCR according to the PCR protocol described in the document EP-A-0,569,272. In the first RT-PCR cycle, the primers M001 and P004 or P005 are used. In the second PCR cycle, the primers M002-A or M003-BCD and the primer P004 are used. The primers are positioned as follows:

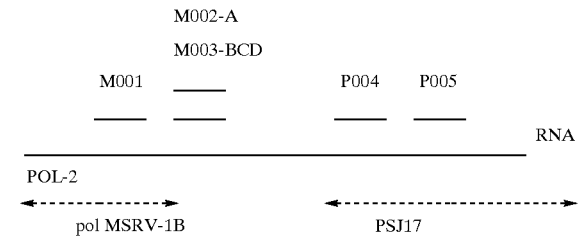

Their composition is:

| | | |
|---|---|---|
| primer M001: | GGTCTTCCICAIGG | (SEQ ID NO:20) |
| primer M002-A: | TTAGGGATAGCCCTCATC TCT | (SEQ ID NO:21) |
| primer M003-BCD: | TCAGGGATAGCCCCCATC TAT | (SEQ ID NO:22) |
| primer P004: | AACCCTTTGCCACTACATCAA TTT | (SEQ ID NO:23) |
| primer P005: | GCGTAAGGACTCCTAGAGCT ATT | (SEQ ID NO:24) |

The "nested" amplification product obtained, and designated M003-P004, is presented in FIG. 7, and corresponds to the sequence SEQ ID NO:8.

EXAMPLE 5

Amplification and Cloning of a Portion of the MSRV-1 Retroviral Genome using a Sequence Already Identified, in a Sample of Virus Purified at the Peak of Reverse Transcriptase Activity A PCR technique derived from the technique published by Frohman (19) was used. The technique derived makes it possible, using a specific primer at the 3' end of the genome to be amplified, to elongate the sequence towards the 5' region of the genome to be analysed. This technical variant is described in the documentation of the firm "Clontech Laboratories Inc.", (Palo-Alto Calif., USA) supplied with its product "5'-AmpliFINDER™ RACE Kit", which was used on a fraction of virion purified as described above.

The specific 3' primers used in the kit protocol for the synthesis of the cDNA and the PCR amplification are, respectively, complementary to the following MSRV-1 sequences:

| | | |
|---|---|---|
| cDNA: | TCATCCATGTACCGAAGG | (SEQ ID NO:25) |
| amplification: | ATGGGGTTCCCAAGTTCCCT | (SEQ ID NO:26) |

The products originating from the PCR were purified after purification on agarose gel according to conventional methods (17), and then resuspended in 10 ml of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 μl of DNA solution were mixed with 5 μl of sterile distilled water, 1 μl of a 10-fold concentrated ligation buffer "10' LIGATION BUFFER", 2 μl of "pCR™ VECTOR" (25 ng/ml) and 1 μl of "TA DNA LIGASE". This mixture was incubated overnight at 12° C. The following steps were carried out according to the instructions of the TA Cloning® kit (British Bio-technology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analysed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning Kit®. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer model 373 A" apparatus according to the manufacturer's instructions.

This technique was applied first to two fractions of virion purified as described below on sucrose from the "POL-2" isolate produced by the PLI-2 line on the one hand, and from the MS7PG isolate produced by the LM7PC line on the other hand. The culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g (or 30,000 rpm in a type 45 T LKB-HITACHI rotor) for 2 h at 4° C. After removal of the supernatant, the sedimented pellet is taken up in a small volume of PBS and constitutes the fraction of concentrated but unpurified virions. The concentrated virus is then applied to a sucrose gradient in sterile PBS buffer (15 to 50% weight/weight) and ultracentrifuged at 35,000 rpm (100,000 g) for 12 h at +40° C. in a swing-out rotor. 10 fractions are collected, and 20 $\mu$l are withdrawn from each fraction after homogenization to assay the reverse transcriptase activity therein accord- ing to the technique described by E. Perron (3). The fractions containing the peak of "LM7-like" RT activity are then diluted in sterile PBS buffer and ultra-centrifuged for one hour at 35,000 rpm (100,000 g) to sediment the viral particles. The pellet of purified virion thereby obtained is then taken up in a small volume of a buffer which is appropriate for the extraction of RNA. The cDNA synthesis reaction mentioned above is carried out on this RNA extracted from purified extracellular virion. PCR amplification according to the technique mentioned above enabled the clone F1-11 to be obtained, whose sequence, identified by SEQ ID NO:2, is presented in FIG. 8.

This clone makes it possible to define, with the different clones previously sequenced, a region of considerable length (1.2 kb) representative of the "pol" gene of the MSRV-1 retrovirus, as presented in FIG. 9. This sequence, designated SEQ ID NO:1, is reconstituted from different clones overlapping one another at their ends, correcting the artefacts associated with the primers and with the amplification or cloning techniques which would artificially interrupt the reading frame of the whole. This sequence will be identified below under the designation "MSRV-1 pol* region". Its degree of homology with the HSERV-9 sequence is shown in FIG. 12.

In FIG. 9, the potential reading frame with its translation into amino acids is presented below the nucleic acid sequence.

EXAMPLE 6

Detection of Specific MSRV-1 and MSRV-2 Sequences in Different Samples of Plasma Originating from Patients Suffering from MS or from Controls A PCR technique was used to detect the MSRV-1 and MSRV-2 genomes in plasmas obtained after taking blood samples from patients suffering from MS and from non-MS controls onto EDTA.

Extraction of the RNAs from plasma was performed according to the technique described by P. Chomzynski (20), after adding one volume of buffer containing guanidinium thiocyanate to 1 ml of plasma stored frozen at −80° C. after collection.

For MSRV-2, the PCR was performed under the same conditions and with the following primers:

5' primer, identified by SEQ ID NO:14 5' GTAGTTC-GATGTAGAAAGCG 3';

3' primer, identified by SEQ ID NO:15 5' GCATCCG-GCAACTGCACG 3'.

However, similar results were also obtained with the following PCR primers in two successive amplifications by "nested" PCR on samples of nucleic acids not treated with DNase.

The primers used for this first step of 40 cycles with a hybridization temperature of 48° C. are the following:

5' primer, identified by SEQ ID NO:27 5' GCCGATAT-CACCCGCCATGG 3', corresponding to a 5' MSRV-2 PCR primer, for a first PCR on samples from patients, 3' primer, identified by SEQ ID NO:28 5' GCATCCG-GCAACTGCACG 3', corresponding to a 3' MSRV-2 PCR primer, for a first PCR on samples from patients.

After this step, 10 $\mu$l of the amplification product are taken and used to carry out a second, so-called "nested" PCR amplification with primers located within the region already amplified. This second step takes place over 35 cycles, with a primer hybridization ("annealing") temperature of 50° C. The reaction volume is 100 $\mu$l.

The primers used for this second step are the following:

5' primer, identified by SEQ ID NO:29 5' CGCGAT-GCTGGTTGGAGAGC 3', corresponding to a 5' MSRV-2 PCR primer, for a nested PCR on samples from patients, 3' primer, identified by SEQ ID NO:30 5' TCTCCACTC-CGAATATTCCG 3', corresponding to a 3' MSRV-2 PCR primer, for a nested PCR on samples from patients.

For MSRV-1, the amplification was performed in two steps. Furthermore, the nucleic acid sample is treated beforehand with DNase, and a control PCR without RT (AMV reverse transcriptase) is performed on the two amplification steps so as to verify that the RT-PCR amplification comes exclusively from the MSRV-1 RNA. In the event of a positive control without RT, the initial aliquot sample of RNA is again treated with DNase and amplified again.

The protocol for treatment with DNase lacking RNAse activity is as follows: the extracted RNA is aliquoted in the presence of "RNAse inhibitor" (Boehringer-Mannheim) in water. treated with DEPC at a final concentration of 1 $\mu$g in 10 $\mu$l; to these 10 $\mu$l, 1 $\mu$l of "RNAse-free DNAse" (Boehringer-Mannheim) and 1.2 $\mu$l of pH 5 buffer containing 0.1 M/l sodium acetate and 5 mM/l MgSO$_4$ is added; the mixture is incubated for 15 min at 20° C. and brought to 95° C. for 1.5 min in a "thermocycler".

The first MSRV-1 RT-PCR step is performed according to a variant of the RNA amplification method as described in Patent Application No. EP-A-0,569,272. In particular, the cDNA synthesis step is performed at 42° C. for one hour; the PCR amplification takes place over 40 cycles, with a. primer hybridization ("annealing") temperature of 53° C. The reaction volume is 100 $\mu$l.

The primers used for this first step are the following:

5' primer, identified by SEQ ID NO:16 5' AGGAGTAAG-GAAACCCAACGGAC 3';

3' primer, identified by SEQ ID NO:17 5' TAAGAGT-TGCACAAGTGCG 3'.

After this step, 10 µl of the amplification product are taken and used to carry out a second, so-called "nested" PCR amplification with primers located within the region already amplified. This second step takes place over 35 cycles, with a primer hybridization ("annealing") temperature of 53° C. The reaction volume is 100 µl.

The primers used for this second step are the following:
5' primer, identified by SEQ ID NO:18 5' TCAGGGAT-AGCCCCCATCTAT 3';
3' primer, identified by SEQ ID NO:19 5' AAC-CCTTTGCCACTACATCAATTT 3'.

FIGS. 10 and 11 present the results of PCR in the form of photographs under ultraviolet light of ethidium bromide-impregnated agarose gels, in which an electrophoresis of the PCR amplification products applied separately to the different wells was performed.

The top photograph (FIG. 10) shows the result of specific MSRV-2 amplification.

Well number 8 contains a mixture of DNA molecular weight markers, and wells 1 to 7 represent, in order, the products amplified from the total RNAs of plasmas originating from 4 healthy controls free from MS (wells 1 to 4) and from 3 patients suffering from MS at different stages of the disease (wells 5 to 7).

In this series, MSRV-2 nucleic acid material is detected in the plasma of one case of MS out of the 3 tested, and in none of the 4 control plasmas. Other results obtained on more extensive series confirm these results.

The bottom photograph (FIG. 11) shows the result of specific amplification. by MSRV-1 "nested" RT-PCR:

well No. 1 contains the PCR product produced with water alone, without the addition of AMV reverse transcriptase; well No. 2 contains the PCR product produced with water alone, with the addition of AMV reverse transcriptase; well number 3 contains a mixture of DNA molecular weight markers; wells 4 to 13 contain, in order, the products amplified from the total RNAs extracted from sucrose gradient fractions (collected in a downward direction), on which gradient a pellet of virion originating from a supernatant of a culture infected with MSRV-1 and MSRV-2 was centrifuged to equilibrium according to the protocol described by H. Perron (13); to well 14 nothing was applied; to wells 15 to 17, the amplified products of RNA extracted from plasmas originating from 3 different patients suffering from MS at different stages of the disease were applied.

The MSRV-1 retroviral genome is indeed to be found in the sucrose gradient fraction containing the peak of reverse transcriptase activity measured according to the technique described by H. Perron (3), with a very strong intensity (fraction 5 of the gradient, placed in well No. 8). A slight amplification has taken place in the first fraction (well No. 4), probably corresponding to RNA released by lysed particles which floated at the surface of the gradient; similarly, aggregated debris has sedimented in the last fraction (tube bottom), carrying with it a few copies of the MSRV-1 genome which have given rise to an amplification of low intensity.

Of the 3 MS plasmas tested in this series, MSRV-1 RNA turned up in one case, producing a very intense amplification (well No. 17).

In this series, the MSRV-1 retroviral RNA genome, probably corresponding to particles of extracellular virus present in the plasma in extremely small numbers, was detected by "nested" RT-PCR in one case of MS out of the 3 tested. Other results obtained on more extensive series confirm these results.

Furthermore, the specificity of the sequences amplified by these PCR techniques may be verified and evaluated by the "ELOSA" technique as described by F. Mallet (21) and in the document FR- A-2,663,040.

For MSRV-1, the products of the nested PCR described above may be tested in two ELOSA systems enabling a consensus A and a consensus B+C+D of MSRV-1 to be detected separately, corresponding to the subfamilies described in Example 1 and FIGS. 1 and 2. In effect, the sequences closely resembling the consensus B+C+D are to be found essentially in the RNA samples originating from MSRV-1 virions purified from cultures or amplified in extracellular biological fluids of MS patients, whereas the sequences closely resembling the consensus A are essentially to be found in normal human cellular DNA.

The ELOSA/MSRV-1 system for the capture and specific hybridization of the PCR products of the subfamily A uses a capture oligonucleotide cpV1A with an amine bond at the 5' end and a biotinylated detection oligonucleotide dpV1A having as their sequence, respectively:

cpV1A identified by SEQ ID NO:31 5' GATCTAGGC-CACTTCTCAGGTCCAGS 3', corresponding to the ELOSA capture oligonucleotide for the products of MSRV-1 nested PCR performed with the primers identified by SEQ ID NO:16 and SEQ ID NO:17, optionally followed by amplification with the primers identified by-SEQ ID NO18 and SEQ ID NO:19 on samples from patients;

dpV1A identified by SEQ ID NO:32; 5' CATCTITTTG-GICAGGCAITAGC 3', corresponding to the ELOSA capture oligonucleotide for the subfamily A of the products of MSRV-1 "nested" PCR performed with the primers identified by SEQ ID NO:16 and SEQ ID NO:17, optionally followed by amplification with the primers identified by SEQ ID NO:18 and SEQ ID NO:19 on samples from patients.

The ELOSA/MSRV-1 system for the capture and specific hybridization of the PCR products of the subfamily B+C+D uses the same biotinylated detection oligonucleotide dpV1A and a capture oligonucleotide cpV1B with an amine bond at the 5' end having as its sequence:

dpV1B identified by SEQ ID NO:33 5' CTTGAGC-CAGTTCTCATACCTGGA 3', corresponding to the ELOSA capture oligonucleotide for the subfamily B+C+D of the products of MSRV-1 "nested" PCR performed with the primers identified by SEQ ID NO:16 and SEQ ID NO:17, optionally followed by amplification with the primers identified by SEQ ID NO:18 and SEQ ID NO:19 on go samples from patients.

This ELOSA detection system enabled it to be verified that none of the PCR products thus amplified from DNase-treated plasmas of MS patients contained a sequence of the subfamily A, and that all were positive with the consensus of the subfamilies B, C and D.

For MSRV-2, a similar ELOSA technique was evaluated on isolates originating from infected cell cultures, using the following PCR amplification primers, 5' primer, identified by SEQ ID NO:34 5' AGTGYTRC-CMCARGGCGCTGAA 3', corresponding to a 5' MSRV-2 PCR primer, for PCR on samples from cultures, 3' primer, identified by SEQ ID NO:35 5' GMGGCCAG-CAGSAKGTCATCCA 3', corresponding to a 3' MSRV-2 PCR primer, for PCR on samples from cultures, and the capture oligonucleotides with an amine bond at the 5' end cpV2 and the biotinylated detection oligonucleotide dpV2 having as their respective sequences:

cpV2 identified by SEQ ID NO:36 5 GGATGCCGC-CTATAGCCTCTAC 3', corresponding to an ELOSA capture oligonucleotide for the products of MSRV-2 PCR performed with the primers SEQ ID NO:34 and SEQ ID NO:35, or optionally with the degenerate primers defined by Shih (12).

dpV2 identified by SEQ ID NO:37
5' AAGCCTATCGCGTGCAGTTGCC 3', corresponding to an ELOSA detection oligonucleotide for the products of MSRV-2 PCR performed with the primers SEQ ID NO:34 and SEQ ID NO:35, or optionally with the degenerate primers defined by Shih (12).

This PCR amplification system with a pair of primers different from those which were described previously for amplification on the samples from patients made it possible to confirm the infection with MSRV-2 of in vitro cultures and of samples of nucleic acids used for the molecular biology studies.

All things considered, the first results of PCR detection of the genome of pathogenic and/or infective agents show that it is possible that free "virus" may circulate in the blood stream of patients in an acute, virulent phase, outside the nervous system. This is compatible with the almost invariable presence of "gaps" in the blood-brain barrier of patients in an active phase of MS.

EXAMPLE 7

Obtaining Sequences of the "env" Gene of the MSRV-1 Retroviral Genome

As has already been described in Example 5, a PCR technique derived from the technique published by Frohman (19) was used. The technique derived makes it possible, using a specific primer at the 3' end of the genome to be amplified, to elongate the sequence towards the 5' region of the genome to be analysed. This technical variant is described in the documentation of "Clontech Laboratories Inc., (Palo-Alto Calif., USA) supplied with its product "5'-AmpliFINDER™ RACE Kit", which was used on a fraction of virion purified as described above.

In order to carry out an amplification of the 3' region of the MSRV-1 retroviral genome encompassing the region of the "env" gene, a study was carried out to determine a consensus sequence in the LTR regions-of the same type as those of the defective endogenous retrovirus HSERV-9 (18, 24), with which the MSRV-1 retrovirus displays partial homologies.

The same specific 3' primer was used in the kit protocol for the synthesis of the cDNA and the PCR amplification; its sequence is as follows:

GTGCTGATTGGTGTATTTACAATCC       (SEQ ID NO 45)

Synthesis of the complementary DNA (cDNA) and unidirectional PCR amplification with the above primer were carried out in one step according to the method described in Patent EP-A-0,569,272.

The products originating from the PCR were extracted after purification of-agarose gel according to conventional methods (17), and then resuspended in 10 ml of distilled water. Since one of the properties of Taq polymerase consists in adding an adenine at the 3' end of each of the two DNA strands, the DNA obtained was inserted directly into a plasmid using the TA Cloning™ kit (British Biotechnology).

The 2 µl of DNA solution were mixed with 5 µl of sterile distilled water, 1 µl of a 10-fold concentrated ligation buffer "10×LIGATION BUFFER", 2 µl of "pCR™ VECTOR" (25 ng/ml) and 1 µl of "TA DNA LIGASE". This mixture was incubated overnight at 12° C. The following steps were carried out according to the instructions of the TA Cloning® kit (British Bio-technology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analysed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning Kit®. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "automatic sequencer, model 373 A [lacuna] apparatus according to the manufacturer's instructions.

This technical approach was applied to a sample of virion concentrated as described below from a mixture of culture supernatants produced by B lymphoblastoid lines such as are described in Example 2, established from lymphocytes of patients suffering from MS and possessing reverse transcriptase activity which is detectable according to the technique described by Perron et al. (3): the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g for 2 h at 4° C. After removal of the supernatant, the sedimented pellet constitutes the sample of concentrated but unpurified virions. The pellet thereby obtained is then taken up in a small volume of an appropriate buffer for the extraction of RNA. The cDNA synthesis reaction mentioned above is carried out on this RNA extracted from concentrated extracellular virion.

RT-PCR amplification according to the technique mentioned above enabled the clone FBd3 to be obtained, whose sequence, identified by SEQ ID NO:46, is presented in FIG. 13.

In FIG. 14, the sequence homology between the clone FBd3 and the HSERV-9 retrovirus is shown on the matrix chart by a continuous line for any partial homology greater than or equal to 65%. It can be seen that there are homologies in the flanking regions of the clone (with the pal gene at the 5' end and with the env gene and then the LTR at the 3' end), but that the internal region is totally divergent and does not display any homology, even weak, with the "env" gene of HSERV9. Furthermore, it is apparent that the clone FBd3 contains a longer "env" region than the one which is described for the defective endogenous HSERV-9; it may thus be seen that the internal divergent region constitutes an "insert" between the regions of partial homology with the HSERV-9 defective genes.

EXAMPLE 8

Amplification, Cloning and Sequencing of the Region of the MSRV-1 Retroviral Genome Located Between the Clones PSJ17 and FBd3

Four oligonucleotides, F1, B4, F6 and B1, were defined for amplifying RNA originating from concentrated virions of the strains POL2 and MS7PG. Control reactions were performed so as to check for the presence of contaminants (reaction with water). The amplification consists of a first step of RT-PCR according to the protocol described in Patent Application EP-A-0,569,272, followed by a second step of PCR performed on 10 ml of product of the first step with primers internal to the amplified first region ("nested" PCR). In the first RT-PCR cycle, the primers F1 and B4 are used. In the second PCR cycle, the primers F6 and the primer B1 are used. The primers are positioned as follows:

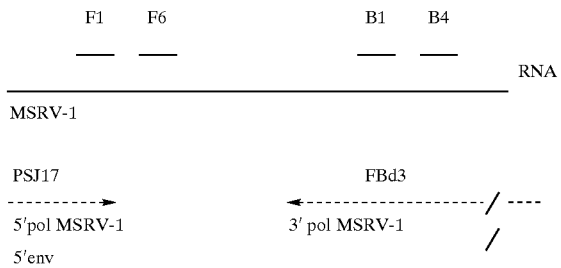

Their composition is:

primer F1: TGATGTGAACGGCATACTCACTG (SEQ ID NO:47)

primer B4: CCCAGAGGTTAGGAACTCCCT
        TTC (SEQ ID NO 48)

primer F6: GCTAAAGGAGACTTGTGGTTGT
        CAG (SEQ ID NO 49)

primer B1: CAACATGGGCATTTCGGATTAG (SEQ ID NO 50)

The product of "nested" amplification obtained and designated "t pol" is presented in FIG. 15, and corresponds to the sequence SEQ ID NO:51.

EXAMPLE 9

Obtaining New Sequences, Expressed as RNA in Cells in Culture Producing MSRV-1, and Comprising an "env" Region of the MSRV-1 Retroviral Genome A library of cDNA was produced according to the procedure described by the manufacturer of the "cDNA synthesis module, cDNA rapid adaptator ligation module, cDNA rapid cloning module and lambda gt10 in vitro packaging module" kits (Amersham, ref RPN1256Y/Z, RPN1712, RPN1713, RPN1717, N334Z), from the messenger RNA extracted from cells of a B lymphoblastoid line such as is described in Example 2, established from the lymphocytes of a patient suffering from MS and possessing reverse transcriptase activity which is detectable according to the technique described by Perron et al. (3).

Oligonucleotides were defined for amplifying the cDNA cloned into the nucleic acid library between the 3' region of the clone PSJ17 (pol) and the 5' (LTR) region of the clone FBd3. Control reactions were performed so as to check for the presence of contaminants (reaction with water). PCR reactions performed on the nucleic acids cloned into the library with different pairs of primers enabled a series [lacuna] clones linking pol sequences to the MSRV-1 type env or LTR sequences to be amplified.

Two clones are representative of the sequences obtained in the cellular cDNA library:

the clone JLBc1, whose sequence SEQ ID NO:52 is presented in FIG. 16;

the clone JLBc2, whose sequence SEQ ID NO:53 is presented in FIG. 17.

The sequences of the clones JLBc1 and JLBc2 are homologous to that of the clone FBd3, as is apparent in FIGS. 18 and 19. The homology between the clone JLBc1 and the clone JLBc2 is shown in FIG. 20.

The homologies between the clones JLBc1 and JLBc2 on the one hand and the HSERV9 sequence on the other hand are presented, respectively, in FIGS. 21 and 22.

It will be noted that the region of homology between JLB1, JLB2 and FBd3 comprises, with a few sequence and size variations of the "insert", the additional sequence absent ("inserted") in the HSERV-9 env sequence, as described in Example 8.

It will also be noted that the cloned "pol" region is very homologous to HSERV-9, does not possess a reading frame (bearing in mind the sequence errors induced by the techniques used, including even the automatic sequencer) and diverges from the MSRV-1 sequences obtained from virions. In view of the fact that these sequences were cloned from the RNA of cells expressing MSRV-1 particles, it is probable that they originate from endogenous retroviral elements related to the ERV9 family; this is all the more likely for the fact that the pol and env genes are present on the same RNA. which is clearly not the MSRV-1 genomic RNA. Some of these ERV9 elements possess functional LTRs which can be activated by replicative viruses coding for homologous or heterologous transactivators. Under these conditions, the relationship between MSRV-1 and HSERV-9 makes probable the transactivation of the defective (or otherwise) endogenous ERV9 elements by homologous, or even identical, MSRV-1 transactivating proteins.

Such a phenomenon may induce a viral interference between the expression of MSRV-1 and the related endogenous elements. Such an interference generally leads to a so-called "defective-interfering" expression, some features of which were to be found in the MSRV-1-infected cultures studied. Furthermore, such a phenomenon does not lack generation of the expression of polypeptides, or even of endogenous retroviral proteins which are not necessarily tolerated by the immune system. Such a scheme of aberrant expression of endogenous elements related to MSRV-1 and induced by the latter is liable to multiply the aberrant antigens, and hence to contribute to the induction of autoimmune processes such as are observed in MS.

It is, however, essential to note that the clones JLBc1 and JLBc2 differ from the ERV9 or HSERV9 sequence already described, in that they possess a longer env region comprising an additional region totally divergent from ERV9. Their kinship with the endogenous ERV9 family may hence be defined, but they clearly constitute novel elements never hitherto described. In effect, interrogation of the data banks of nucleic acid sequences available in version No. 15 (1995) of the "Entrez" software (NCBI, NIH, Bethesda, USA) did not enable a known homologous sequence in the env region of these clones to be identified.

EXAMPLE 10

Obtaining Sequences Located in the 5' pol and 3' gag Region of the MSRV-1 Retroviral Genome As has already been described in Example 5, a PCR technique derived from the technique published by Frohman (19) was used. The technique derived makes it possible, using a specific primer at the 3' end of the genome to be amplified, to elongate the sequence towards the 5' region of the genome to be analysed. This technical variant is described in the documentation of the firm "Clontech Laboratories Inc., (Palo-Alto Calif., USA) supplied with its product "5'-AmpliFINDER™ RACE Kit", which was used on a fraction of virion purified as described above.

In order to carry out an amplification of the 5' region of the MSRV-1 retroviral genome starting from the pol sequence already sequenced (clone F11-1) and extending towards the gag gene, MSRV-1 specific primers were defined.

The specific 3' primers used in the kit protocol for the synthesis of the cDNA and the PCR amplification are, respectively, complementary to the following MSRV-1 sequences:

cDNA: CCTGAGTTCTTGCACTAACCC (SEQ ID NO:54)

amplification: GTCCGTTGGGTTTCCTTACT CCT (SEQ ID NO:55)

The products originating from the PCR were extracted after purification on agarose gel according to conventional methods (17), and then resuspended in 10 ml of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 µl of DNA solution were mixed with 5 µl of sterile distilled water, 1 µl of a 10-fold concentrated ligation buffer "10×LIGATION BUFFER", 2 µl of "pCR™ VECTOR" (25 ng/ml) and 1 µl of "TA DNA LIGASE". This mixture was incubated overnight at 12° C. The following steps were carried out according to the instructions of the TA Cloning® kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analysed on agarose gel. Plasmids possessing an insert detected under UV light after staining the gel with ethidium bromide were selected for sequencing of the insert, after hybridization with a primer complementary to the Sp6 promoter. present on the cloning plasmid of the TA Cloning Kit®. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "automatic sequencer model 373 A [lacuna] apparatus according to the manufacturer's instructions.

This technical approach was applied to a sample of virion concentrated as described below from a mixture of culture supernatants produced by B lymphoblastoid lines such as are described in Example 2, established from lymphocytes of patients suffering from MS and possessing reverse transcriptase activity which is detectable according to the technique described by Perron et al. (3): the culture supernatants are collected twice weekly, precentrifuged at 10,000 rpm for 30 minutes to remove cell debris and then frozen at −80° C. or used as they are for the following steps. The fresh or thawed supernatants are centrifuged on a cushion of 30% glycerol-PBS at 100,000 g for 2 h at 4° C. After removal of the supernatant, the sedimented pellet constitutes the sample of concentrated but unpurified virions. The pellet thereby obtained is then taken up in a small volume of an appropriate buffer for the extraction of RNA. The cDNA synthesis reaction mentioned above is carried out on this RNA extracted from concentrated extracellular virion.

RT-PCR amplification according to the technique mentioned above enabled the clone GM3 to be obtained, whose sequence, identified by SEQ ID NO 56, is presented in FIG. 23.

In FIG. 24, the sequence homology between the clone GMP3 and the HSERV-9 retrovirus is shown on the matrix chart by a continuous line, for any partial homology greater than or equal to 65%.

In summary, FIG. 25 shows the localization of the different clones studied above, relative to the known ERV9 genome. In FIG. 25, since the MSRV-1 env region is longer than the reference ERV9 env gene, the additional region is shown above the point of insertion according to a "V", on the understanding that the inserted material displays a sequence and size vari-ability between the clones shown (JLBc1, JLBc2, FBd3). And FIG. 26 shows the position of different clones studied in the MSRV-1 pol* region.

By means of the clone GM3 described above, a possible reading frame could be defined, covering the whole of the pol gene, referenced according to SEQ ID NO:57, shown in the successive FIGS. 27a to 27c.

EXAMPLE 11

Detection of Anti-MSRV-1 Specific Antibodies in Human Serum

Identification of the sequence of the pol gene of the MSRV-1 retrovirus and of an open reading frame of this gene-enabled the amino acid sequence SEQ ID NO:39 of a region of the said gene, referenced SEQ ID NO:40, to be determined (see FIG. 28).

Different synthetic peptides corresponding to fragments of the protein sequence of MSRV-1 reverse transcriptase encoded by the pol gene were tested for their antigenic specificity with respect to sera of patients suffering from MS and of healthy controls.

The peptides were synthesized chemically by solid-phase synthesis according to the Merrifield technique (Barany G, and Merrifielsd R. B, 1980, In the Peptides, 2, 1–284, Gross E and Meienhofer J, Eds., Academic Press, New York). The practical details are those described below.
a) Peptide Synthesis The peptides were synthesized on a phenylacetamidomethyl (PAM)/polystyrene/divinylbenzene resin (Applied Biosystems, Inc. Foster City, Calif.), using an "Applied Biosystems 430A" automatic synthesizer. The amino acids are coupled in the form of hydroxybenzotriazole (HOBT) esters. The amino acids-used are obtained from Novabiochem (Läuflerlfingen, Switzerland) or Bachem (Bubendorf, Switzerland).

The chemical synthesis was performed using a double coupling protocol with N-methylpyrrolidone (NMP) as solvent. The peptides were cut from the resin, as well as the side-chain protective groups, simultaneously, using hydrofluoric acid (HF) in a suitable apparatus (type I cleavage apparatus, Peptide Institute, Osaka, Japan).

For 1 g of peptidyl resin, 10 ml of HF, 1 ml of anisole and 1 ml of dimethyl sulphide 5DMS are used. The mixture is stirred for 45 minutes at −2° C. The HF is then evaporated off under vacuum. After intensive washes with ether, the peptide is eluted from the resin with 10% acetic acid and then lyophilized.

The peptides are purified by preparative high performance liquid chromatography on a VYDAC C18 type column (250×21 mm) (The Separation Group, Hesperia, Calif., USA). Elution is carried out with an acetonitrile gradient at a flow rate of 22 ml/min. The fractions collected are monitored by an elution under isocratic conditions on a VYDAC® C18 analytical column (250×4.6 mm) at a flow rate of 1 ml/min. Fractions having the same retention time are pooled and lyophilized. The preponderant fraction is then analysed by analytical high performance liquid chromatography with the system described above. The peptide which is considered to be of acceptable purity manifests itself in a single peak representing not less than 95% of the chromatogram.

The purified peptides are then analysed with the object of monitoring their amino acid composition, using an Applied Biosystems 420H automatic amino acid analyser. Measurement of the (average) chemical molecular mass of the peptides is obtained using LSIMS mass spectrometry in the positive ion mode on a VG. ZAB.ZSEQ double focusing instrument connected to a DEC-VAX 2000 acquisition system (VG analytical Ltd, Manchester, England).

The reactivity of the different peptides was tested against sera of patients suffering from MS and against sera of healthy controls. This enabled a peptide designated POL2B to be selected, whose sequence is shown in FIG. 28 in the identifier SEQ ID NO:39, below, encoded by the pol gene of MSRV-1 (nucleotides 181 to 330).

b) Antigenic Properties

The antigenic properties of the POL2B peptide were demonstrated according to the ELISA protocol described below.

The lyophilized POL2B peptide was dissolved in sterile distilled water at a concentration of 1 mg/ml. This stock solution was aliquoted and kept at +4° C. for use over a fortnight, or frozen at −20° C. for use within 2 months. An aliquot is diluted in PBS (phosphate buffered saline) solution so as to obtain a final peptide concentration of 1 microgram/ml. 100 microlitres of this dilution are placed in each well of microtitration plates ("high-binding" plastic, COSTAR ref: 3590). The plates are covered with a "plate-sealer" type adhesive and kept overnight at +4° C. for the phase of adsorption of the peptide to the plastic. The adhesive is removed and the plates are washed three times with a volume of 300 microlitres of a solution A (1×PBS, 0.05% Tween 200), then inverted over an absorbent tissue. The plates thus drained are filled with 200 microlitres per well of a solution B (solution A+10% of goat serum), then covered with an adhesive and incubated for 45 minutes to 1 hour at 37° C. The plates are then washed three times with the solution A as described above.

The test serum samples are diluted beforehand to 1/50 in the solution B, and 100 microlitres of each dilute test serum are placed in the wells of each microtitration plate. A negative control is placed in one well of each plate, in the form of 100 microlitres of buffer B. The plates covered with an adhesive are then incubated for 1 to 3 hours at 37° C. The plates are then washed three times with the solution A as described above. In parallel, a peroxidase-labelled goat antibody directed against human IgG (Sigma Immunochemicals ref. A6029) or IgM (Cappel ref. 55228) is diluted in the solution B (dilution 1/5000 for the anti-IgG and 1/1000 for the anti-IgM). 100 microlitres of the appropriate dilution of the labelled antibody are then placed in each well of the microtitration plates, and the plates covered with an adhesive are incubated for 1 to 2 hours at 37° C. A further washing of the plates is then performed as described above. In parallel, the peroxidase substrate is prepared according to the directions of the "Sigma fast OPD kit" (Sigma Immunochemicals, ref. P9187). 100 microlitres of substrate solution are placed in each well, and the plates are placed protected from light for 20 to 30 minutes at room temperature.

When the colour reaction has stabilized, the plates are placed immediately in an ELISA plate spectrophotometric reader, and the optical density (OD) of each well is read at a wavelength of 492 nm. Alternatively, 30 microlitres of 1N HCL are placed in each well to stop the reaction, and the plates are read in the spectrophotometer within 24 hours.

The serological samples are introduced in duplicate or in triplicate, and the optical density (OD) corresponding to the serum tested is calculated by taking the mean of the OD values obtained for the same sample at the same dilution.

The net OD of each serum corresponds to the mean OD of the serum minus the mean OD of the negative control (solution B: PBS, 0.05% Tween 20®, 10% goat serum).

c) Detection of Anti-MSRV-1 IgG Antibodies by ELISA

The technique described above was used with the POLB2 peptide to test for the presence of anti-MSRV-1 specific IgG antibodies in the serum of 29 patients for whom a definite or probable diagnosis of MS was established according to the criteria of Poser (23), and of 32 healthy controls (blood donors).

FIG. 29 shows the results for each serum tested with an anti-IgG antibody. Each vertical bar represents the net optical density (OD at 492 nm) of a serum tested. The ordinate axis gives the net OD at the top of the vertical bars. The first 29 vertical bars lying to the left of the vertical broken line represent the sera of 29 cases of MS tested, and the 32 vertical bars lying to the right of the vertical broken line represent the sera of 32 healthy controls (blood donors).

The mean of the net OD values for the MS sera tested is 0.62. The diagram enables 5 controls to be revealed whose net OD rises above the grouped values of the control population. These values may represent the presence of specific IgGs in symptomless seropositive patients. Two methods were hence evaluated in order to determine the statistical threshold of positivity of the test.

The mean of the net OD values for the controls, including the controls with high net OD values, is 0.36. Without the 5 controls whose net OD values are greater than or equal to 0.5, the mean of the "negative" controls is 0.33. The standard deviation of the negative controls is 0.10. A theoretical threshold of positivity may be calculated according to the formula:

threshold value (mean of the net OD values of the seronegative controls)+(2 or 3×standard deviation of the net OD values of the seronegative controls).

In the first case, there are considered to be symptomless seropositives, and the threshold value is equal to 0.33+(2× 0.10)=0.53. The negative results represent a non-specific "background" of the presence of antibodies directed specifically against an epitope of the peptide.

In the second case, if the set of controls consisting of blood donors in apparent good health is taken as a reference basis, without excluding the sera which are, on the face of it, seropositive, the standard deviation of the "non-MS controls" is 0.116. The threshold value then becomes 0.36+ (2×0.116)=0.59.

According to this analysis, the test is specific for MS. In this respect, it is seen that the test is specific for MS, since, as shown in Table 1, no control has a net OD above this threshold. In fact, this result reflects the fact that the antibody titres in patients suffering from MS are, for the most part, higher than in vhealthy controls who have been in contact with MSRV-1.

TABLE NO. 1

| | MS | CONTROLS |
|---|---|---|
| | 0.681 | 0.3515 |
| | 1.0425 | 0.56 |
| | 0.5675 | 0.3565 |
| | 0.63 | 0.449 |
| | 0.588 | 0.2825 |
| | 0.645 | 0.55 |
| | 0.6635 | 0.52 |
| | 0.576 | 0.2535 |
| | 0.7765 | 0.55 |
| | 0.5745 | 0.51 |
| | 0.513 | 0.426 |
| | 0.4325 | 0.451 |
| | 0.7255 | 0.227 |
| | 0.859 | 0.3905 |
| | 0.6435 | 0.265 |
| | 0.5795 | 0.4295 |
| | 0.8655 | 0.291 |
| | 0.671 | 0.347 |
| | 0.596 | 0.4495 |
| | 0.662 | 0.3725 |
| | 0.602 | 0.181 |
| | 0.525 | 0.2725 |
| | 0.53 | 0.426 |
| | 0.565 | 0.1915 |
| | 0.517 | 0.222 |
| | 0.607 | 0.395 |
| | 0.3705 | 0.34 |
| | 0.397 | 0.307 |
| | 0.4395 | 0.219 |
| | | 0.491 |
| | | 0.2265 |
| | | 0.2605 |
| MEAN | 0.62 | 0.33 |
| STD DEV | 0.14 | 0.10 |
| THRESHOLD VALUE | | 0.53 |

In accordance with the first method of calculation, and as shown in FIG. 29 and in the corresponding Table 1, 26 of the 29 MS sera give a positive result (net OD greater than or equal to 0.50), indicating the presence of IgGs specifically directed against the POL2B peptide, hence against a portion of the reverse transcriptase enzyme of the MSRV-1 retrovirus encoded by its pol gene, and consequently against the MSRV-1 retrovirus. Thus, approximately 90% of the MS patients tested have reacted against an epitope carried by the POL2B peptide and possess circulating IgGs directed against the latter.

Five out of 32 blood donors in apparent good health show a positive result. Thus, it is apparent that approximately 15%. of the symptomless population may have been in contact with an epitope carried by the POL2B peptide under conditions which have led to an active immunization which manifests itself in the persistence of specific serum IgGs. These conditions are compatible with an immunization against the MSRV-1 retrovirus reverse transcriptase during an infection with (and/or reactivation of) the MSRV-1 retrovirus. The absence of apparent neurological pathology recalling MS in these seropositive controls may indicate that they are healthy carriers and have eliminated an infectious virus after immunizing themselves, or that they constitute an at risk population of chronic carriers. In effect, epidemiological data showing that a pathogenic agent present in the environment of regions of high prevalence of MS may be the cause of this disease imply that a fraction of the population free from MS has necessarily been in contact with such a pathogenic agent. It has been shown that the MSRV-1 retrovirus constitutes all or part of this "pathogenic agent" at the source of MS, and it is hence normal for controls taken from a healthy population to possess IgG type antibodies against components of the MSRV-1 retrovirus. Thus, the difference in seroprevalence between the MS and control populations is extremely significant: "chi-squared" test, $p<0.001$. These results, hence point to an aetiopathogenic role of MSRV-1 in MS.

d) Detection of Anti-MSRV-1 IgM Antibodies by ELISA

The ELISA technique with the POL2B peptide was used to test for the presence of anti-MSRV-1 IgM specific antibodies in the serum of 36 patients for whom a definite or probable diagnosis of MS was established according to the criteria of Poser (23), and of 42 healthy controls (blood donors).

FIG. 30 shows the results for each serum tested with an anti-IgM antibody. Each vertical bar represents the net optical density (OD at 492 nm) of a serum tested. The ordinate axis gives the net OD at the top of the vertical bars. The first 36 vertical bars lying to the left of the vertical line cutting the abscissa axis represent the sera of 36 cases of MS tested, and the vertical bars lying to the right of the vertical broken line represent the sera of 42 healthy controls (blood donors). The horizontal line drawn in the middle of the diagram represents a theoretical threshold defining the boundary of the positive results (in which the top of the bar lies above) and the negative results (in which the top of the bar lies below).

The mean of the net OD values for the MS cases tested is 0.19.

The mean of the net OD values for the controls is 0.09.

The standard deviation of the negative controls is 0.05.

In view of the small difference between the mean and the standard deviation of the controls, the threshold of theoretical positivity may be calculated according to the formula:

threshold value=(mean of the net OD values of the seronegative controls)+(3×standard deviation of the net OD values of the seronegative controls).

The threshold value is hence equal to 0.09+(3×0.05)= 0.26; or, in practice, 0.25.

The negative results represent a non-specific "background" of the presence of antibodies directed specifically against an epitope of the peptide.

According to this analysis, and as shown in FIG. 30 and in the corresponding Table 2, the IgM test is specific for MS, since no control has a net OD above the threshold. 7 of the 36 MS sera produce a positive IgM result; now, a study of the clinical data reveals that these positive sera were taken during a first attack of MS or an acute attack in untreated patients. It is known that IgMs directed against pathogenic agents are produced during primary infections or during reactivations following a latency phase of the said pathogenic agent.

The difference in seroprevalence between the MS and control populations is extremely significant: "chi-squared" test, $p<0.001$.

These results point to an aetiopathogenic role of MSRV-1 in MS.

The detection of IgM and IgG antibodies against the POL2B peptide enables the course of an MSRV-1 infection and/or of the viral reactivation of MSRV-1 to be evaluated.

TABLE NO. 2

| MS | CONTROLS |
|---|---|
| 0.064 | 0.243 |
| 0.087 | 0.11 |
| 0.044 | 0.098 |
| 0.115 | 0.028 |
| 0.089 | 0.094 |

TABLE NO. 2-continued

| | MS | CONTROLS |
|---|---|---|
| | 0.025 | 0.038 |
| | 0.097 | 0.176 |
| | 0.108 | 0.146 |
| | 0.018 | 0.049 |
| | 0.234 | 0.161 |
| | 0.274 | 0.113 |
| | 0.225 | 0.079 |
| | 0.314 | 0.093 |
| | 0.522 | 0.127 |
| | 0.306 | 0.02 |
| | 0.143 | 0.052 |
| | 0.375 | 0.062 |
| | 0.142 | 0.074 |
| | 0.157 | 0.043 |
| | 0.168 | 0.046 |
| | 1.051 | 0.041 |
| | 0.104 | 0.13 |
| | 0.187 | 0.153 |
| | 0.044 | 0.107 |
| | 0.053 | 0.178 |
| | 0.153 | 0.114 |
| | 0.07 | 0.078 |
| | 0.033 | 0.118 |
| | 0.104 | 0.177 |
| | 0.187 | 0.026 |
| | 0.044 | 0.024 |
| | 0.053 | 0.046 |
| | 0.153 | 0.116 |
| | 0.07 | 0.04 |
| | 0.033 | 0.028 |
| | 0.973 | 0.073 |
| | | 0.008 |
| | | 0.074 |
| | | 0.141 |
| | | 0.219 |
| | | 0.047 |
| | | 0.017 |
| MEAN | 0.19 | 0.09 |
| STD. DEV. | 0.23 | 0.05 |
| THRESHOLD VALUE | | 0.26 | e) Search for Immunodominant Epitopes in the POL2B Peptide

In order to reduce the non-specific background and to optimize the detection of the responses of the anti-MSRV-1 antibodies, the synthesis of octapeptides, advancing in successive one amino acid steps, covering the whole of the sequence determined by POL2B, was carried out according to the protocol described below.

The chemical synthesis of overlapping octapeptides covering the amino acid sequence 61–110 shown in the identifier SEQ ID NO:39 was carried out on an activated cellulose membrane according to the technique of BERG et al. (1989. J. Ann. Chem. Soc., 111, 8024–8026) marketed by Cambridge Research Biochemicals under the trade name Spotscan. This technique permits the simultaneous synthesis of a large number of peptides and their analysis.

The synthesis is carried out with esterified amino acids in which the α-amino group is protected with an FMOC group (Nova Biochem) and the side-chain groups with protective groups such as trityl, t-butyl ester or t-butyl ether. The esterified amino acids are solubilized in N-methylpyrrolidone (NMP) at a concentration of 300 nM, and 0.9 $\mu$l are applied to spots of deposit of bromophenol blue. After incubation for 15 minutes, a further application of amino acids is carried out according to another 15-minute incubation. If the coupling between two amino acids has taken place correctly, a coloration modification (change from blue to yellow-green) is observed. After three washes in DMF, an acetylation step is performed with acetic anhydride. Next, the terminal amino groups of the peptides in the process of synthesis are deprotected with 20% pyridine in DMF. The spots of deposit are restained with a 1% solution of bromophenol blue in DMF, washed three times with methanol and dried. This set of operations constitutes one cycle of addition of an amino acid, and this cycle is repeated until the synthesis is complete. When all the amino acids have been added, the NH2-terminal group of the last amino acid is deprotected with 20% piperidine in DMF and acetylated with acetic anhydride. The groups protecting the side chain are removed with a dichloromethane/trifluoroacetic acid/triisobutylsilane (5 ml/5 ml/250 ml) mixture. The immunoreactivity of the peptides is then tested by ELISA.

After synthesis of the different octapeptides in duplicate on two different membranes, the latter are rinsed with methanol and washed in TBS (0.1M Tris pH 7.2), then incubated overnight at room temperature in a saturation buffer. After several washes in TBS-T (0.1M Tris pH 7.2–0.05% Tween 20), one membrane is incubated with a 1/50 dilution of a reference serum originating from a patient suffering from MS, and the other membrane with a 1/50 dilution of a pool of sera of healthy controls. The membranes are incubated for 4 hours at room temperature. After washes with TBS-T, a β-galactosidase-labelled anti-human immunoglobulin conjugate (marketed by Cambridge Research Biochemicals) is added at a dilution of 1/200, and the mixture is incubated for two hours at room temperature. After washes of the membranes with 0.05% TBS-T and PBS, the immunoreactivity in the different spots is visualized by adding 5-bromo-4-chloro-3-indolyl β-D-galactopyranoside in potassium. The intensity of coloration of the spots is estimated qualitatively with a relative value from 0 to 5 as shown in the attached FIGS. 31 to 33.

In this way, it is possible to determine two immunodominant regions at each end of the POL2B peptide, corresponding, respectively, to the amino acid sequences 65–75 (SEQ ID NO:41) and 92–109 (SEQ ID NO:42), according to FIG. 34, and lying, respectively, between the octapeptides Phe-Cys-Ile-Pro-Val-Arg-Pro-Asp (FCIPVRPD) and Arg-Pro-Asp-Ser-Gln-Phe-Leu-Phe (RPDSQFLF), and Thr-Val-Leu-Pro-Gln-Gly-Phe-Arg (TVLPQGFR) and Leu-Phe-Gly-Gln-Ala-Leu-Ala-Gln (LFGQALAQ), and a region which is less reactive but apparently more specific, since it does not produce any background with the control serum, represented by the octapeptides Leu-Phe-Ala-Phe-Glu-Asp-Pro-Leu (LFAFEDPL) (SEQ ID NO:43) and Phe-Ala-Phe-Glu-Asp-Pro-Leu-Asn (FAFEDPLN) (SEQ ID NO:44).

These regions make it possible to define new peptides which are more specific and more immunoreactive according to the usual techniques.

It is thus possible, as a result of the discoveries made and the methods developed by the inventors, to carry out a diagnosis of MSRV-1 infection and/or reactivation and to evaluate a therapy in MS on the basis of its efficacy in "negativing" the detection of these agents in the patients' biological fluids. Furthermore, early detection in individuals not yet displaying neurological signs of MS could make it possible to institute a treatment which would be all the more effective with respect to the subsequent clinical course for the fact that it would precede the lesion stage which corresponds to the onset of neurological disorders. Now, at the present time, a diagnosis of MS cannot be established before a symptomatology of neurological lesions has set in, and hence no treatment is instituted before the emergence of a clinical picture suggestive of lesions of the central nervous system which are already significant. The diagnosis of an MSRV-1 and/or MSRV-2 infection and/or reactivation in man is hence of decisive importance, and the present invention provides the means of doing this.

It is thus possible, apart from carrying out a diagnosis of MSRV-1 infection and/or reactivation, to evaluate a therapy in MS on the basis of its efficacy in "negativing" the detection of these agents in the patients' biological fluids.

EXAMPLE 12

Obtaining a Clone LB19 Containing a Portion of the GAG Gene of the MSRV-1 Retrovirus A PCR technique derived from the technique published by Gonzalez-Quintial R et al. (19) and PLAZA et al. (25) was used. From the total RNAs extracted from a fraction of virion purified as described above, the cDNA was synthesized using a specific primer (SEQ ID No.64) at the 3' end of the genome to be amplified, using EXPAND™ REVERSE TRANSCRIPTASE (BOEHRINGER MANNHEIM).

cDNA: AAGGGGCATG GACGAGGTGG
TGGCTTATTT (SEQ ID NO:65) (antisense)

After purification, a poly(G) tail was added at the 5' end of the cDNA using the "Terminal transferases kit" marketed by the company Boehringer Mannheim, according to the manufacturer's protocol.

An anchoring PCR was carried out using the following 5' and 3' primers:

AGATCTGCAG AATTCGATAT CACCCCCCCC CCCCCC (SEQ ID No. 91) (sense), and AAAT-GTCTGC GGCACCAATC TCCATGTT (SEQ ID No. 64) (antisense)

Next, a semi-nested anchoring PCR was carried out with the following 5' and 3' primers:

AGATCTGCAG AATTCGATAT CA (SEQ ID No.92) (sense), and AAATGTCTGC GGCACCAATC TCCATGTT (SEQ ID No.64) (antisense)

The products originating from the PCR were purified after purification on an agarose gel according to conventional methods (17), and then resuspended in microlitres of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 µl of DNA solution were mixed with 5 µl of sterile distilled water, 1 µl of 10-fold concentrated ligation buffer "10×LIGATION BUFFER", 2 µl of "pCR™ VECTOR" (25 ng/ml) and 1 µl of "T4 DNA LIGASE". This mixture was incubated overnight at 12° C. The following steps were carried out according to the instructions of the TA Cloning® kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analysed on agarose gel. Plasmids possessing an insert detected under UV light after staining the gel with ethidium bromide were selected for sequencing of the insert, after hybridization with a primer complementary to the Sp6 promoter present on the cloning plasmid of the TA Cloning Kit®. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

PCR amplification according to the technique mentioned above was used on a cDNA synthesized from the nucleic acids of fractions of infective particles purified on a sucrose gradient, according to the technique described by H. Perron (13), from culture supernatants of B lymphocytes of a patient suffering from MS, immortalized with Epstein-Barr virus (EBV) strain B95 and expressing retroviral particles associated with reverse transcriptase activity as described by Perron et al. (3) and in French Patent Applications MS 10, 11 and 12. the clone LB19, whose sequence, identified by SEQ ID NO:59, is presented in FIG. 35.

The clone makes it possible to define, with the clone GM3 previously sequenced and the clone G+E+A (see Example 15), a region of 690 base pairs representative of a significant portion of the gag gene of the MSRV-1 retrovirus, as presented in FIG. 36. This sequence designated SEQ ID NO:88 is reconstituted from different clones overlapping at their ends. This sequence is identified under the name MSRV-1 "gag*" region. In FIG. 36, a potential reading frame with the translation into amino acids is presented below the nucleic acid sequence.

EXAMPLE 13

Obtaining a Clone FBd13 Containing a pol Gene Region Related to the MSRV-1 Retrovirus and an Apparently Incomplete ENV Region Containing a Potential Reading Frame (ORF) for a Glycoprotein Extraction of viral RNAs The RNAs were extracted according to the method briefly described below.

A pool of culture supernatant of B lymphocytes of patients suffering from MS (650 ml) is centrifuged for 30 minutes at 10,000 g. The viral pellet obtained is resuspended in 300 microlitres of PBS/10 mM MgCl2. The material is treated with a DNAse (100 mg/ml)/RNAse (50 mg/ml) mixture for 30 minutes at 37° C. and then with proteinase K (50 mg/ml) for 30 minutes at 46° C.

The nucleic acids are extracted with one volume of a phenol/0.1% SDS (V/V) mixture heated to 60° C., and then re-extracted with one volume of phenol/chloroform (1:1; V/V).

Precipitation of the material is performed with 2.5 V of ethanol in the presence of 0.1 V of sodium acetate pH=5.2. The pellet obtained after centrifugation is resuspended in 50 microlitres of sterile DEPC water.

The sample is treated again with 50 mg/ml of "RNAse free" DNAse for 30 minutes at room temperature, extracted with one volume of phenol/chloroform and precipitated in the presence of sodium acetate and ethanol.

The RNA obtained is quantified by an OD reading at 260 nm. The presence of MSRV-1 and the absence of DNA contaminant is monitored by a PCR and an MSRV-1-specific RTPCR associated with a specific ELOSA for the MSRV-1 genome.

Synthesis of cDNA 5 mg of RNA are used to synthesize a cDNA primed with a poly(DT) oligonucleotide according to the instructions of the "cDNA Synthesis Module" kit (ref RPN 1256, Amersham) with a few modifications: The reverse transcription is performed at 45° C. instead of the recommended 42° C.

The synthesis product is purified by a double extraction and a double purification according to the manufacturer's instructions.

The presence of MSRV-1 is verified by an MSRV-1 PCR associated with a specific ELOSA for the MSRV-1 genome.

"Long Distance PCR": (LD-PCR)

500 ng of cDNA are used for the LD-PCR step (Expand Long Template System; Boehringer (ref.1681 842)).

Several pairs of oligonucleotides were used. Among these, the pair defined by the following primers:

5' primer: GGAGAAGAGC AGCATAAGTG G  (SEQ ID No. 66)

3' primer: GTGCTGATTG GTGTATTTAC
       AATCC  (SEQ ID No. 67).

The amplification conditions are as follows:

94° C. 10 seconds

56° C. 30 seconds

68° C. 5 minutes;

10 cycles, then 20 cycles with an increment of 20 seconds in each cycle on the elongation time. At the end of this first amplification, 2 microlitres of the amplification product are subjected to a second amplification under the same conditions as before.

The LD-PCR reactions are conducted in a Perkin model 9600 PCR apparatus in thin-walled microtubes (Boehringer).

The amplification products are monitored by electrophoresis of 1/5th of the amplification volume (10 microlitres) in 1% agarose gel. For the pair of primers described above, a band of approximately 1.7 Kb is obtained.

Cloning of the Amplified Fragment

The PCR product was purified by passage through a preparative agarose gel and then through a Costar column (Spin; D. Dutcher) according to the supplier's instructions.

2 microlitres of the purified solution are joined up with 50 ng of vector PCRII according to the supplier's instructions (TA Cloning Kit; British Biotechnology)).

The recombinant vector obtained is isolated by transformation of competent DH5aF' bacteria. The bacteria are selected using their resistance to ampicillin and the loss of metabolism for Xgal (=white colonies). The molecular structure of the recombinant vector is confirmed by plasmid minipreparation and hydrolysis with the enzyme EcoR1.

FBd13, a positive clone for all these criteria, was selected. A large-scale preparation of the recombinant plasmid was performed using the Midiprep Quiagen kit (ref 12243) according to the supplier's instructions.

Sequencing of the clone FBd13 is performed by means of the Perkin Prism Ready Amplitaq FS dye terminator kit (ref. 402119) according to the manufacturer's instructiions. The sequence reactions are introduced into a Perkin type 377 or 373A automatic sequencer. The sequencing strategy consists in gene walking carried out on both strands of the clone Fbd13.

The sequence of the clone FBd1 3 is identified by SEQ ID NO 58.

In FIG. 37, the sequence homology between the clone FBd13 and the HSERV-9 retrovirus is shown on the matrix chart by a continuous line for any partial homology greater than or equal to 70%. It can be seen that there are homologies in the flanking regions of the clone (with the pol gene at the 5' end and with the env gene and then the LTR at the 3' end), but that the internal region is totally divergent and does not display any homology, even weak, with the env gene of HSERV-9. Furthermore, it is apparent that the clone FBd13 contains a longer "env" region than the one which is described for the defective endogenous HSERV-9; it may thus be seen that the internal divergent region constitutes an "insert" between the regions of partial homology with the HSERV-9 defective genes.

This additional sequence determines a potential orf, designated ORF B13, which is represented by its amino acid sequence SEQ ID NO:87.

The molecular structure of the clone FBd13 was analyzed using the GeneWork software and Genebank and SwissProt data banks.

5 glycosylation sites were found.

The protein does not have significant homology with already known sequences.

It is probable that this clone originates from a recombination of an endogenous retroviral element (ERV), linked to the replication of MSRV-1.

Such a phenomenon does not lack generation of the expression of polypeptides, or even of endogenous retroviral proteins which are not necessarily tolerated by the immune system. Such a scheme of aberrant expression of endogenous elements related to MSRV-1 and/or induced by the latter is liable to multiply the aberrant antigens, and hence tends to contribute to the induction of autoimmune processes such as are observed in MS. It clearly constitutes a novel element never hitherto described. In effect, interrogation of the data banks of nucleic acid sequences available in version No. 19 (1996) of the "Entrez" software (NCBI, NIH, Bethesda, USA) did not enable a known homologous sequence comprising the whole of the env region of this clone to be identified.

EXAMPLE 14

Obtaining a Clone FP6 Containing a Portion of the pol Gene, with a Region Coding for the Reverse Transcriptase Enzyme Homologous to the Clone pol* MSRV-1, and a 3'Pol Region Divergent from the Equivalent Sequences Described in the Clones Pol*, Tpol, FBd3, JLBc1 and JLBc2.

A 3'RACE was performed on total RNA extracted from plasma of a patient suffering from MS. A healthy control plasma treated under the same conditions was used as negative control. The synthesis of cDNA was carried out with the following modified oligo(dT) primer:

5' GACTCGCTGC AGATCGATTT TTTTTTTTTT
       TTTT 3'  (SEQ ID NO:68)

and Boehringer "Expand RT" reverse transcriptase according to the conditions recommended by the company. A PCR was performed with the enzyme Klentaq (Clontech) under the following conditions: 94° C. 5 min then 93° C. 1 min, 58° C. 1 min, 68° C. 3 min for 40 cycles and 68° C. for 8 min, and with a final reaction volume of 50 µl.

Primers used for the PCR:

5' primer, identified by SEQ ID NO:69 5' GCCAT-CAAGC CACCCAAGAA CTCTTAACTT 3';

3' primer, identified by SEQ ID NO:68 (=the same as for the cDNA)

A second, so-called "semi-nested" PCR was carried out with a 5' primer located within the region already amplified. This second PCR was performed under the same experimental conditions as those used in the first PCR, using 10 µl of the amplification product originating from the first PCR.

Primers used for the semi-nested PCR:

5' primer, identified by SEQ ID NO:70 5' CCAATAGCCA GACCATTATA TACACTAATT 3';

3' primer, identified by SEQ ID NO:68 (=the same as for the cDNa)

Primers SEQ ID NO:69 and SEQ ID NO:70 are specific for the pol* region: position No. 403 to No. 422 and No. 641 to No. 670, respectively.

An amplification product was thus obtained from the extracellular RNA extracted from the plasma of a patient suffering from MS. The corresponding fragment was not observed for the plasma of the healthy control. This amplification product was cloned in the following manner.

The amplified DNA was inserted into a plasmid using the TA Cloning™ kit. The 2 µl of DNA solution were mixed with 5 µl of sterile distilled water, 1 µl of a 10-fold concentrated ligation buffer "10×LIGATION BUFFER", 2 µl of "pCR™ VECTOR" (25 ng/ml) and 1 µl of "TA DNA LIGASE". This mixture was incubated overnight at 12° C. The following steps were carried out according to the instructions of the TA Cloning kits (British Biotechnology). At the end of the procedure, the white columns of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. Plasmids possessing an insert detected under UV light after staining the gel with ethidium bromide was selected for sequencing of the insert, after hybridization with a primer complementary to the Sp6 promoter present on the cloning plasmid of the TA cloning kit®. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the manufacturer's instructions.

The clone obtained, designated FP6, enables a region of 467 bp which is 89% homologous to the pol* region of the MSRV-1 retrovirus and a region of 1167 bp which is 64% homologous to the pol region of ERV-9 (No. 1634 to 2856) to be defined.

The clone FP6 is represented in FIG. 38 by its nucleotide sequence identified by SEQ ID NO:61. The three potential reading frames of this clone are indicated by their amino acid sequence under the nucleotide sequence.

EXAMPLE 15

Obtaining a Region Designated G+E+A Containing an ORF for a Retroviral Protease, by PCR Amplification of the Nucleic Acid Sequence Contained Between the 5' Region Defined by the Clone "GM3" and the 3' Region Defined by the Clone pol*, from the RNA Extracted from a Pool of Plasmas of Patients Suffering from MS Oligonucleotides specific for the MSRV-1 sequences already identified by the Applicant were defined in order to amplify the retroviral RNA originating from virions present in the plasma of patients suffering from MS. Control reactions were performed so as to monitor the presence of contaminants (reaction with water). The amplification consists of a step of RT-PCR followed by a "nested" PCR. Pairs of primers were defined for amplifying three overlapping regions (designated G, E and A) on the regions defined by the sequences of the clones GM3 and pol* described above. Semi-nested RT-PCR for Amplification of the Region G in the first RT-PCR cycle, the following primers are used:
- primer 1: SEQ ID NO:71 (sense)
- primer 2: SEQ ID NO:72 (antisense)

in the second PCR cycle, the following primers are used:
- primer 1: SEQ ID NO:73 (sense)
- primer 4: SEQ ID NO:74 (antisense)

Nested RT-PCR for Amplification of the Region E
in the first RT-PCR cycle, the following primers are used:
- primer 5: SEQ ID NO:75 (sense)
- primer 6: SEQ ID NO:76 (antisense)

in the second PCR cycle, the following primers are used:
- primer 7: SEQ ID NO:77 (sense)
- primer 8: SEQ ID NO:78 (antisense)

Semi-nested RT-PCR for Amplification of the Region A
in the first RT-PCR cycle, the following primers are used:
- primer 9: SEQ ID NO:79 (sense)
- primer 10: SEQ ID NO:80 (antisense)

in the second PCR cycle, the following primers are used:
- primer 9: SEQ ID NO:81 (sense)
- primer 11: SEQ ID NO:82 (antisense)

The primers and the regions G, E and A which they define are positioned as follows:

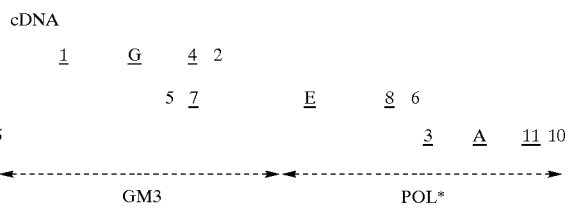

The sequence of the region defined by the different clones G, E and A was determined after cloning and sequencing of the "nested" amplification products.

The clones G, E and A were assembled together by PCR with the primers 1 at the 5' end of the fragment G and 11 at the 3' end of the. fragment A, the primers being described above. An approximately 1580-bp fragment G+E+A was amplified and inserted into a plasmid using the TA Cloning (trademark) kit. The sequence of the amplification product corresponding to G+E+A was determined and analysis of the G+E and E+A overlaps was carried out. The sequence is shown in FIG. 39, and corresponds to the sequence SEQ ID NO:89.

A reading frame coding for an MSRV-1 retroviral protease was found in the region E. The amino acid sequence of the protease, identified by SEQ ID NO:90, is presented in FIG. 40.

EXAMPLE 16

Obtaining a Clone LTRGAG12, Related to an Endogenous Retroviral Element (ERV) Close to MSRV-1, in the DNA of an MS Lymphoblastoid Line Producing Virions and Expressing the MSRV-1 Retrovirus A nested PCR was performed on the DNA extracted from a lymphoblastoid line (B lymphocytes immortalized with the EBV virus strain B95, as described above and as is well known to a person skilled in the art) expressing the MSRV-1 retrovirus and originating from peripheral blood lymphocytes of a patient suffering from MS.

In the first PCR step, the following primers are used:

primer 4327: CTCGATTTCT TGCTGGGCCT
TA (SEQ ID NO:83)

primer 3512: GTTGATTCCC TCCTCAAGCA (SEQ ID NO:84)

This step comprises 35 amplification cycles with the following conditions: 1 min at 94° C., 1 min at 54° C. and 4 min at 72° C.

In the second PCR step, the following primers are used:

primer 4294: CTCTACCAAT CAGCATGTGG (SEQ ID NO:85)

primer 3591: TGTTCCTCTT GGTCCCTAT (SEQ ID NO:86)

This step comprises 35 amplification cycles with the following conditions: 1 min at 94° C., 1 min at 54° C. and 4 min at 72° C.

The products originating from the PCR were purified after purification on agarose gel according to conventional methods (17), and then resuspended in 10 ml of distilled water. Since one of the properties of Taq polymerase consists in adding an adenine at the 3' end of each of the two DNA strands, the DNA obtained was inserted directly into a plasmid using the TA Cloning™ kit (British Biotechnology). The 2 µl of DNA solution were mixed with 5 µl of sterile distilled water, 1 µl of a 10-fold concentrated ligation buffer "10×LIGATION BUFFER", 2 µl of "pCR™ VECTOR" (25 ng/ml) and 1 µl of "TA DNA LIGASE". This mixture was incubated overnight at 12° C. The following steps were carried out according to the instructions of the TA Cloning® kit (British Biotechnology). At the end of the procedure, the white colonies of recombinant bacteria (white) were picked out in order to be cultured and to permit extraction of the plasmids incorporated according to the so-called "miniprep" procedure (17). The plasmid preparation from each recombinant colony was cut with a suitable restriction enzyme and analyzed on agarose gel. The plasmids possessing an insert detected under UV light after staining the gel with ethidium bromide were selected for sequencing of the insert, after hybridization with a primer complementary to the Sp6 promoter present on the cloning plasmid of the TA Cloning Kit®. The reaction prior to sequencing was then performed according to the method recommended for the use of the sequencing kit "Prism ready reaction kit dye deoxyterminator cycle sequencing kit" (Applied Biosystems, ref. 401384), and automatic sequencing was carried out with an Applied Biosystems "Automatic Sequencer, model 373 A" apparatus according to the.manufacturer's instructions.

Thus, a clone designated LTRGAG12 could be obtained, and is represented by its internal sequence identified by SEQ ID NO:60.

This clone is probably representative of endogenous elements close to ERV-9, present in human DNA, in particular in the DNA of patients suffering from MS, and capable of interfering with the expression of the MSRV-1 retrovirus, hence capable of having a role in the pathogenesis associated with the MSRV-1 retrovirus and capable of serving as marker for a specific expression in the pathology in question.

EXAMPLE 17

Detection of Anti -MSRV-1 Specific Antibodies in Human Serum

Identification of the sequence of the pol gene of the MSRV-1 retrovirus and of an open reading frame of this gene enabled the amino acid sequence SEQ ID NO:63 of a region of the said gene, referenced SEQ ID NO:62, to be determined.

Different synthetic peptides corresponding to fragments of the protein sequence of MSRV-1 reverse transcriptase encoded by the pol gene were tested for their antigenic specificity with respect to sera of patients suffering from MS and of healthy controls.

The peptides were synthesized chemically by solid-phase synthesis according to the Merrifield technique (22). The practical details are those described below.

a) Peptide Synthesis

The peptides were synthesized on a phenylacetamidomethyl (PAM)/polystyrene/divinylbenzene resin (Applied Biosystems, Inc. Foster City, Calif.), using an "Applied Biosystems 430A" automatic synthesizer. The amino acids are coupled in the form of hydroxybenzotriazole (HOBT) esters. The amino acids used are obtained from Novabiochem (Läuflerlfingen, Switzerland) or Bachem (Bubendorf, Switzerland).

The chemical synthesis was performed using a double coupling protocol with N-methylpyrrolidone (NMP) as solvent. The peptides were cut from the resin, as well as the side-chain protective groups, simultaneously, using hydrofluoric acid (HF) in a suitable apparatus (type I cleavage apparatus, Peptide Instiute, Osaka, Japan).

For 1 g of peptidyl resin, 10 ml of HF, 1 ml of anisole and 1 ml of dimethyl sulphide 5DMS are used. The mixture is stirred for 45 minutes at −2° C. The HF is then evaporated off under vacuum. After intensive washes with ether, the peptide is eluted from the resin with 10% acetic acid and then lyophilized.

The peptides are purified by preparative high performance liquid chromatography on a VYDAC C18 type column (250×21 mm) (The Separation Group, Hesperia, Calif., USA). Elution is carried out with an acetonitrile gradient at a flow rate of 22 ml/min. The fractions collected are monitored by an elution under isocratic conditions on a VYDAC® C18 analytical column (250×4.6 mm) at a flow rate of 1 ml/min. Fractions having the same retention time are pooled and lyophilized. The preponderant fraction is then analysed by analytical high performance liquid chromatography with the system described above. The peptide which is considered to be of acceptable purity manifests itself in a single peak representing not less than 95% of the chromatogram.

The purified peptides are then analysed with the object of monitoring their amino acid composition, using an Applied Biosystems 420H automatic amino acid analyser. Measurement of the (average) chemical molecular mass of the peptides is obtained using LSIMS mass spectrometry in the positive ion mode on a VG. ZAB.ZSEQ double focusing instrument connected to a DEC-VAX 2000 acquisition system (VG analytical Ltd, Manchester, England).

The reactivity of the different peptides was tested against sera of patients suffering from MS and against sera of healthy controls. This enabled a peptide designated S24Q to be selected, whose sequence is identified by SEQ ID NO:63, encoded by a nucleotide sequence of the pol gene of MSRV-1 (SEQ ID NO:62).

b) Antigenic Properties

The antigenic properties of the S24Q peptide were demonstrated according to the ELISA protocol described below.

The lyophilized S24Q peptide was dissolved in 10% acetic acid at a concentration of 1 mg/ml. This stock solution was aliquoted and kept at +4° C. for use over a fortnight, or frozen at −20° C. for use within 2 months. An aliquot is diluted in PBS (phosphate buffered saline) solution so as to obtain a final peptide concentration of 5 micrograms/ml. 100 microlitres of this dilution are placed in each well of Nunc Maxisorb (trade name) microtitration plates. The plates are covered with a "plate-sealer" type adhesive and kept for 2 hours at +37° C. for the phase of adsorption of the peptide to the plastic. The adhesive is removed and the plates are washed three times with a volume of 300 microlitres of a solution A (1×PBS, 0.05% Tween 200), then inverted over an absorbent tissue. The plates thus drained are filled with 250 microlitres per well of a solution B (solution A+10% of goat serum), then covered with an adhesive and incubated for 1 hour at 37° C. The plates are then washed three times with the solution A as described above.

The test serum samples are diluted beforehand to 1/100 in the solution B, and 100 microlitres of each dilute test serum are placed in the wells of each microtitration plate. A negative control is placed in one well of each plate, in the form of 100 microlitres of buffer B. The plates covered with an adhesive are then incubated for 1 hour 30 min at 37° C. The plates are then washed three times with the solution A as described above. For the IgG response, a peroxidase-labelled goat antibody directed against human IgG (marketed by Jackson Immuno Research Inc.) is diluted in the solution B (dilution 1/10,000). 100 microlitres of the appropriate dilution of the labelled antibody are then placed in each well of the microtitration plates, and the plates covered with an adhesive are incubated for 1 hour at 37° C. A further washing of the plates is then performed as described above. In parallel, the peroxidase substrate is prepared according to the directions of the bioMérieux kits. 100 microlitres of substrate solution are placed in each well, and the plates are placed protected from light for 20 to 30 minutes, at room temperature.

When the colour reaction has stabilized, 50 microlitres of Color 2 (bioMérieux trade name) are placed in each well in order to stop the reaction. The plates are placed immediately in an ELISA plate spectrophotometric reader, and the optical density (OD) of each well is read at a wavelength of 492 nm.

The serological samples are introduced in duplicate or in triplicate, and the optical density (OD) corresponding to the serum tested is calculated by taking the mean of the OD values obtained for the same sample at the same dilution.

The net OD of each serum corresponds to the mean OD of the serum minus the mean OD of the negative control (solution B: PBS, 0.05% Tween 20®, 10% goat serum).

c) Detection of Anti-MSRV-1 IgG Antibodies (S24Q) by ELISA

The technique described above was used with the S24Q peptide to test for the presence of anti-MSRV-1 specific IgG antibodies in the serum of 15 patients for whom a definite diagnosis of MS was established according to the criteria of Poser (23), and of 15 healthy controls (blood donors).

FIG. 41 shows the results for each serum tested with an anti-IgG antibody. Each vertical bar represents the net optical density (OD at 492 nm) of a serum tested. The ordinate axis gives the net OD at the top of the vertical bars. The first 15 vertical bars lying to the left of the vertical broken line represent the sera of 15 healthy controls (blood donors), and the 15 vertical bars lying to the right of the vertical broken line represent the sera of 15 cases of MS tested. The diagram enables 2 controls to be revealed whose OD rises above the grouped values of the control population. These values may represent the presence of specific IgGs in symptomless seropositive patients. Two methods were hence evaluated in order to determine the statistical threshold of positivity of the test.

The mean of the net OD values for the controls, including the controls with high net OD values, is 0.129 and the standard deviation is 0.06. Without the 2 controls whose OD values are greater than 0.2, the mean of the "negative" controls is 0.107 and the standard deviation is 0.03. A theoretical threshold of positivity may be calculated according to the formula:

threshold value (mean of the net OD values of the negative controls)+(2 or 3×standard deviation of the net OD values of the negative controls).

In the first case, there are considered to be symptomless seropositives, and the threshold value is equal to 0.11+(3× 0.03)=0.20. The negative results represent a non-specific "background" of the presence of antibodies directed specifically against an epitope of the peptide.

In the second case, if the set of controls consisting of blood donors in apparent good health is taken as a reference basis, without excluding the sera which are, on the face of it, seropositive, the standard deviation of the "non-MS controls" is 0.116. The threshold value then becomes 0.13+ (3×0.06)=0.31.

According to this latter analysis, the test is specific for MS. in this respect, it is seen that the test is specific for MS, since, as shown in Table 1, no control has a net OD above this threshold. In fact, this result reflects the fact that the antibody titres in patients suffering from MS are, for the most part, higher than in healthy controls who have been in contact with MSRV-1.

In accordance with the first method of calculation, and as shown in FIG. 41 and in Table 3, 6 of the MS sera give a positive result (OD greater than or equal to 0.2), indicating the presence of IgGs specifically directed against the S24Q peptide, hence against a portion of the reverse transcriptase enzyme of the MSRV-1 retrovirus encoded by its pol gene, and consequently against the MSRV-1 retrovirus.

Thus, approximately 40% of the MS patients tested have reacted against an epitope carried by the S24Q peptide and possess circulating IgGs directed against the latter.

Two out of 15 blood donors in apparent good health show a positive result. Thus, it is apparent that approximately 13% of the symptomless population may have been in contact with an epitope carried by the S24Q peptide under conditions which have led to an active immunization which manifests itself in the persistence of specific serum IgGs. These conditions are compatible with an immunization against the MSRV-1 retrovirus reverse transcriptase during an infection with (and/or reactivation of) the MSRV-1 retrovirus. The absence of apparent neurological pathology recalling MS in these seropositive controls may indicate that they are healthy carriers and have eliminated an infectious virus after immunizing themselves, or that they constitute an at risk population of chronic carriers. In effect, epidemiological data showing that a pathogenic agent present in the environment of regions of high prevalence of MS may be the cause of this disease imply that a fraction of the population free from MS has necessarily been in contact with such a pathogenic agent. It has been shown that the MSRV-1 retrovirus constitutes all or part of this "pathogenic agent" at the source of MS, and it is hence normal for controls taken from a healthy population to possess IgG type antibodies against components of the MSRV-1 retrovirus.

Lastly, the detection of anti-S24Q antibodies in only one out of two MS cases tested here may reflect the fact that this peptide does not represent an immunodominant MSRV-1 epitope, that inter-individual strain variations may induce an immunization against a divergent peptide motif in the same region, or that the course of the disease and the treatments followed may modulate over time the antibody response against the S24Q peptide.

TABLE NO. 3

| CONTROLS MS |
|---|
| 0.101 |
| 0.136 |
| 0.058 |
| 0.391 |

TABLE NO. 3-continued

| | CONTROLS MS |
|---|---|
| | 0.126 |
| | 0.37 |
| | 0.131 |
| | 0.119 |
| | 0.105 |
| | 0.267 |
| | 0.294 |
| | 0.141 |
| | 0.116 |
| | 0.102 |
| | 0.088 |
| | 0.18 |
| | 0.105 |
| | 0.411 |
| | 0.172 |
| | 0.164 |
| | 0.137 |
| | 0.049 |
| | 0.223 |
| | 0.644 |
| | 0.08 |
| | 0.268 |
| | 0.073 |
| | 0.065 |
| | 0.132 |
| | 0.074 |
| Mean | 0.129 |
| Standard Deviation | 0.06 |
| Threshold | 0.31 | d) Detection of Anti-MSRV-1 IgM Antibodies by ELISA

The ELISA technique with the S24Q peptide was used to test for the presence of anti-MSRV-1 IgM specific antibodies in the same sera as above.

FIG. 42 shows the results for each serum tested with an anti-IgM antibody. Each vertical bar represents the net optical density (OD at 492 nm) of a serum tested. The ordinate axis gives the net OD at the top of the vertical bars. The first 15 vertical bars lying to the left of the vertical line cutting the abscissa axis represent the sera of 15 healthy controls (blood donors), and the vertical bars lying to the right of the vertical broken line represent the sera of 15 cases of MS tested.

The mean of the OD values for the MS cases tested is 1.6.
The mean of the net OD values for the controls is 0.7.
The standard deviation of the negative controls is 0.6.
The threshold of theoretical positivity may be calculated according to the formula:

threshold value=(mean of the OD values of the negative controls)+(3×standard deviation of the OD values of the negative controls).

The threshold value is hence equal to 0.7+(3×0.6)=2.5;

The negative results represent a non-specific "background" of the presence of antibodies directed specifically against an epitope of the peptide.

According to this analysis, and as shown in FIG. 42 and in the corresponding Table 4, the IgM test is specific for MS, since no control has a net OD above the threshold. 6 of the 15 MS sera produce a positive IgM result The difference in seroprevalence between the MS and control populations is extremely significant: "chi-squared" test, p<0.002.

These results point to an aetiopathogenic role of MSRV-1 in MS.

Thus, the detection of IgM and IgG antibodies against the S24Q peptide makes it possible to evaluate, alone or in combination with other MSRV-1 peptides, the course of an MSRV-1 infection and/or of the viral reactivation of MSRV-1.

TABLE NO. 4

| | CONTROLS MS |
|---|---|
| | 1.449 |
| | 0.974 |
| | 0.371 |
| | 6.117 |
| | 0.448 |
| | 2.883 |
| | 0.456 |
| | 1.945 |
| | 0.885 |
| | 1.787 |
| | 2.235 |
| | 0.273 |
| | 0.301 |
| | 1.766 |
| | 0.138 |
| | 0.668 |
| | 0.16 |
| | 2.603 |
| | 1.073 |
| | 0.802 |
| | 1.366 |
| | 0.245 |
| | 0.283 |
| | 0.147 |
| | 0.262 |
| | 2.441 |
| | 0.585 |
| | 0.287 |
| | 0.356 |
| | 0.589 |
| Mean | 0.7 |
| Standard Deviation | 0.6 |
| Threshold | 2.5 |

It is possible, as a result of the new discoveries made and the new methods developed by the inventors, to permit the improved implementation of diagnostic tests for MSRV-1 infection and/or reactivation and to evaluate a therapy in MS and/or RA on the basis of its efficacy in "negativing" the detection of these agents in the patient's biological fluids. Furthermore, early detection in individuals not yet displaying neurological signs of MS or rheumatological signs of RA could make it possible to institute a treatment which would be all the more effective with respect to the subsequent clinical course for the fact that it would precede the lesion stage which corresponds to the onset of the clinical disorders. Now, at the present time, a diagnosis of MS or RA cannot be established before a symptomatology of lesions has set in, and hence no treatment is instituted before the emergence of a clinical picture suggestive of lesions which are already significant. The diagnosis of an MSRV-1 and/or MSRV-2 infection and/or reactivation in man is hence of decisive importance, and the present invention provides the means of doing this.

It is thus possible, apart from carrying out a diagnosis of MSRV-1 infection and/or reactivation, to evaluate a therapy in MS on the basis of its efficacy in =negativing" the detection of these agents in the patients' biological fluids.

BIBLIOGRAPHY (1) Norrby E., Prog. Med. Virol., 1978; 24, 1–39.
(2) Johnson R. T., "Handbook of clinical neurology, 47 Demyelinating diseases", Vinken P. and Bruyn G. W., eds. Amsterdam, Elsevier Science Publishing, 1985, 319–336.

(3) Perron R. et al., Res. Virol. 1989, 140, 551–561.
(4) Perron E. et al., "Current concepts in multiple sclerosis" Wiethölter et al., eds. Amsterdam, Elsevier, 1991, 111–116.
(5) Perron B. et al., The Lancet 1991, 337, 862–863.
(6) Perron H. et al., J. Gen. Virol. 1993, 74, 65–72.
(7) Fields and Knipe, Fondamental Virology 1986, Rev Press N.Y.
(8) Nielsen P. E. et al., Science 1991; 254, 1497–1500.
(9) Maniatis et al., Molecular Cloning, Cold Spring Harbour, 1982.
(10) Southern. E. M., J. Mol. Biol. 1975, 98, 503.
(11) Dunn A. R. and Hassel J. A., Cell 1977, 12, 23,
(12) Shih et al., J. Virol. 1989, 63, 64–75.
(13) Perron H. et al., Res. Vir. 1992, 143, 337–350.
(14) Meyerhans et al., Cell 1989, 58, 901–910.
(15) Linial N. L. and Miller A. D., "Current topics in microbiology and immunobiology. Retroviruses, strategies of replication" vol. 157, 125–152; Swanstrom R. and Vogt P. K., editors, Springer-Verlag, Heidelberg 1990.
(16) Lori F. et al., J. Virol. 1992, 66, 5067–5074.
(17) Sambrook J., Fritsch E. F. and Maniatis T., Molecular cloning, a laboratory manual. Cold Spring Harbour Laboratory Press, 1989.
(18) La Mantia et al., Nucleic Acids Research 1991, 19, 1513–1520.
(19) Gonzales-Quintial R, Baccala R, Pope R M and Theofilopoulos N, J. Clin. Invest, Vol. 97, Number 5, pp1335–1343, 1996.
(20) Chomzynski P. and N. Sacchi, Analytical Biochemistry 1987, 162, 156–159.
(21) F. Mallet et al., Journal of Clinical Microbiology 1993; 31, 1444–1449.
(22) G. Barany and R. B. Merrifielsd, 1980, In the Peptides, 2, 1–284, Gross E and Meienhofer J, Eds., Academic Press, New York.
(23) Poser et al., Gbers G. C. eds. The diagnosis of multiple sclerosis Thieme Stratton Inc, New York 1984: 225–229.
(24) La Mantia et al., Nucleic Acid Research 1989, 17, 5913–22.
(25) PLAZA, A; KONO, D. H.; THEOFILOPOULOS, A. N. NEW HUMAN Vβ 12DD GENES AND POLYMORPHIC VARIANTS. J. Imm; 147(12): 4360–4365, 1991.

SEQUENCE LISTING (1) GENERAL INFORMATION:

(iii) NUMBER OF SEQUENCES: 92

(2) INFORMATION FOR SEQ ID NO: 1:

(i) SEQUENCE CHARACTERISTICS:
        (A) LENGTH: 1158 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 1:

CCCTTTGCCA CTACATCAAT TTTAGGAGTA AGGAAACCCA ACGGACAGTG GAGGTTAGTG      60

CAAGAACTCA GGATTATCAA TGAGGCTGTT GTTCCTCTAT ACCCAGCTGT ACCTAACCCT     120

TATACAGTGC TTTCCCAAAT ACCAGAGGAA GCAGAGTGGT TTACAGTCCT GGACCTTAAG    180

GATGCCTTTT TCTGCATCCC TGTACGTCCT GACTCTCAAT TCTTGTTTGC CTTTGAAGAT    240

CCTTTGAACC CAACGTCTCA ACTCACCTGG ACTGTTTTAC CCCAAGGGTT CAGGGATAGC    300

CCCCATCTAT TTGGCCAGGC ATTAGCCCAA GACTTGAGTC AATTCTCATA CCTGGACACT    360

CTTGTCCTTC AGTACATGGA TGATTTACTT TTAGTCGCCC GTTCAGAAAC CTTGTGCCAT    420

CAAGCCACCC AAGAACTCTT AACTTTCCTC ACTACCTGTG GCTACAAGGT TTCCAAACCA    480

AAGGCTCGGC TCTGCTCACA GGAGATTAGA TACTNAGGGC TAAAATTATC CAAAGGCACC    540

AGGGCCCTCA GTGAGGAACG TATCCAGCCT ATACTGGCTT ATCCTCATCC CAAAACCCTA    600

AAGCAACTAA GAGGGTTCCT TGGCATAACA GGTTTCTGCC GAAAACAGAT TCCCAGGTAC    660

ASCCCAATAG CCAGACCATT ATATACACTA ATTANGGAAA CTCAGAAAGC CAATACCTAT    720

TTAGTAAGAT GGACACCTAC AGAAGTGGCT TTCCAGGCCC TAAAGAAGGC CCTAACCCAA    780

GCCCCAGTGT TCAGCTTGCC AACAGGGCAA GATTTTTCTT TATATGCCAC AGAAAAAACA    840

GGAATAGCTC TAGGAGTCCT TACGCAGGTC TCAGGGATGA GCTTGCAACC CGTGGTATAC    900

CTGAGTAAGG AAATTGATGT AGTGGCAAAG GGTTGGCCTC ATNGTTTATG GGTAATGGNG    960

```
GCAGTAGCAG TCTNAGTATC TGAAGCAGTT AAAATAATAC AGGGAAGAGA TCTTNCTGTG    1020

TGGACATCTC ATGATGTGAA CGGCATACTC ACTGCTAAAG GAGACTTGTG GTTGTCAGAC    1080

AACCATTTAC TTAANTATCA GGCTCTATTA CTTGAAGAGC CAGTGCTGNG ACTGCGCACT    1140

TGTGCAACTC TTAAACCC                                                  1158

(2) INFORMATION FOR SEQ ID NO: 2:

(i) SEQUENCE CHARACTERISTICS:
        (A) LENGTH: 297 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 2:

CCCTTTGCCA CTACATCAAT TTAGGAGTA AGGAAACCCA ACGGACAGTG GAGGTTAGTG       60

CAAGAACTCA GGATTATCAA TGAGGCTGTT GTTCCTCTAT ACCCAGCTGT ACCTAACCCT     120

TATACAGTGC TTTCCCAAAT ACCAGAGGAA GCAGAGTGG TTACAGTCCT GGACCTTAAG     180

GATGCCTTTT TCTGCATCCC TGTACGTCCT GACTCTCAAT TCTTGTTTGC CTTTGAAGAT    240

CCTTTGAACC CAACGTCTCA ACTCACCTGG ACTGTTTTAC CCCAAGGGTT CAAGGGA       297

(2) INFORMATION FOR SEQ ID NO: 3:

(i) SEQUENCE CHARACTERISTICS:
        (A) LENGTH: 85 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 3:

GTTTAGGGAT ANCCCTCATC TCTTTGGTCA GGTACTGGCC CAAGATCTAG GCCACTTCTC      60

AGGTCCAGSN ACTCTGTYCC TTCAG                                            85

(2) INFORMATION FOR SEQ ID NO: 4:

(i) SEQUENCE CHARACTERISTICS:
        (A) LENGTH: 86 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 4:

GTTCAGGGAT AGCCCCCATC TATTTGGCCA GGCACTAGCT CAATACTTGA GCCAGTTCTC      60

ATACCTGGAC AYTCTYGTCC TTCGGT                                           86

(2) INFORMATION FOR SEQ ID NO: 5:

(i) SEQUENCE CHARACTERISTICS:
        (A) LENGTH: 85 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 5:

GTTCARRGAT AGCCCCCATC TATTTGGCCW RGYATTAGCC CAAGACTTGA GYCAATTCTC      60
```

```
ATACCTGGAC ACTCTTGTCC TTYRG                                              85
```

(2) INFORMATION FOR SEQ ID NO: 6:

(i) SEQUENCE CHARACTERISTICS:
        (A) LENGTH: 85 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 6:

```
GTTCAGGGAT AGCTCCCATC TATTTGGCCT GGCATTAACC CGAGACTTAA GCCAGTTCTY         60

ATACGTGGAC ACTCTTGTCC TTTGG                                              85
```

(2) INFORMATION FOR SEQ ID NO: 7:

(i) SEQUENCE CHARACTERISTICS:
        (A) LENGTH: 111 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 7:

```
GTGTTGCCAC AGGGGTTTAR RGATANCYCY CATCTMTTTG GYCWRGYAYT RRCYCRAKAY         60

YTRRGYCAVT TCTYAKRYSY RGSNAYTCTB KYCCTTYRGT ACATGGATGA C                111
```

(2) INFORMATION FOR SEQ ID NO: 8:

(i) SEQUENCE CHARACTERISTICS:
        (A) LENGTH: 645 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 8:

```
TCAGGGATAG CCCCCATCTA TTTGGCCAGG CATTAGCCCA AGACTTGAGT CAATTCTCAT         60

ACCTGGACAC TCTTGTCCTT CAGTACATGG ATGATTTACT TTTAGTCGCC CGTTCAGAAA        120

CCTTGTGCCA TCAAGCCACC CAAGAACTCT TAACTTTCCT CACTACCTGT GGCTACAAGG        180

TTTCCAAACC AAAGGCTCGG CTCTGCTCAC AGGAGATTAG ATACTNAGGG CTAAAATTAT        240

CCAAAGGCAC CAGGGCCCTC AGTGAGGAAC GTATCCAGCC TATACTGGCT TATCCTCATC        300

CCAAAACCCT AAAGCAACTA AGAGGGTTCC TTGGCATAAC AGGTTTCTGC CGAAAACAGA        360

TTCCCAGGTA CASCCCAATA GCCAGACCAT TATATACACT AATTANGGAA ACTCAGAAAG        420

CCAATACCTA TTTAGTAAGA TGGACACCTA CAGAAGTGGC TTTCCAGGCC CTAAAGAAGG        480

CCCTAACCCA AGCCCCAGTG TTCAGCTTGC CAACAGGGCA AGATTTTTCT TTATATGCCA        540

CAGAAAAAAC AGGAATAGCT CTAGGAGTCC TTACGCAGGT CTCAGGGATG AGCTTGCAAC        600

CCGTGGTATA CCTGAGTAAG GAAATTGATG TAGTGGCAAA GGGTT                       645
```

(2) INFORMATION FOR SEQ ID NO: 9:

(i) SEQUENCE CHARACTERISTICS:
        (A) LENGTH: 741 base pairs
        (B) TYPE: nucleotide
        (C) STRANDEDNESS: single (D) TOPOLOGY: linear (ii) MOLECULE TYPE: cDNA (xi) SEQUENCE DESCRIPTION: SEQ ID NO: 9:

CAAGCCACCC AAGAACTCTT AAATTTCCTC ACTACCTGTG GCTACAAGGT TTCCAAACCA      60

AAGGCTCAGC TCTGCTCACA GGAGATTAGA TACTTAGGGT TAAAATTATC CAAAGGCACC     120

AGGGGCCTCA GTGAGGAACG TATCCAGCCT ATACTGGGTT ATCCTCATCC CAAAACCCTA     180

AAGCAACTAA GAGGGTTCCT TAGCATGATC AGGTTTCTGC CGAAAACAAG ATTCCCAGGT     240

ACAACCAAAA TAGCCAGACC ATTATATACA CTAATTAAGG AAACTCAGAA AGCCAATACC     300

TATTTAGTAA GATGGACACC TAAACAGAAG GCTTTCCAGG CCCTAAAGAA GGCCCTAACC     360

CAAGCCCCAG TGTTCAGCTT GCCAACAGGG CAAGATTTTT CTTTATATGG CACAGAAAAA     420

ACAGGAATCG CTCTAGGAGT CCTTACACAG GTCCGAGGGA TGAGCTTGCA ACCCGTGGCA     480

TACCTGAATA AGGAAATTGA TGTAGTGGCA AAGGGTTGGC CTCATNGTTT ATGGGTAATG     540

GNGGCAGTAG CAGTCTNAGT ATCTGAAGCA GTTAAAATAA TACAGGGAAG AGATCTTNCT     600

GTGTGGACAT CTCATGATGT GAACGGCATA CTCACTGCTA AAGGAGACTT GTGGTTGTCA     660

GACAACCATT TACTTAANTA TCAGGCTCTA TTACTTGAAG AGCCAGTGCT GNGACTGCGC     720

ACTTGTGCAA CTCTTAAACC C                                              741

(2) INFORMATION FOR SEQ ID NO: 10:

(i) SEQUENCE CHARACTERISTICS:
        (A) LENGTH: 93 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 10:

TGGAAAGTGT TGCCACAGGG CGCTGAAGCC TATCGCGTGC AGTTGCCGGA TGCCGCCTAT      60

AGCCTCTACA TGGATGACAT CCTGCTGGCC TCC                                  93

(2) INFORMATION FOR SEQ ID NO: 11:

(i) SEQUENCE CHARACTERISTICS:
        (A) LENGTH: 96 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 11:

TTGGATCCAG TGYTGCCACA GGGCGCTGAA GCCTATCGCG TGCAGTTGCC GGATGCCGCC      60

TATAGCCTCT ACGTGGATGA CCTSCTGAAG CTTGAG                               96

(2) INFORMATION FOR SEQ ID NO: 12:

(i) SEQUENCE CHARACTERISTICS:
        (A) LENGTH: 748 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 12:

```
TGCAAGCTTC ACCGCTTGCT GGATGTAGGC CTCAGTACCG GNGTGCCCCG CGCGCTGTAG      60

TTCGATGTAG AAAGCGCCCG GAAACACGCG GGACCAATGC GTCGCCAGCT TGCGCGCCAG     120

CGCCTCGTTG CCATTGGCCA GCGCCACGCC GATATCACCC GCCATGGCGC CGGAGAGCGC     180

CAGCAGACCG GCGGCCAGCG GCGCATTCTC AACGCCGGGC TCGTCGAACC ATTCGGGGGC     240

GATTTCCGCA CGACCGCGAT GCTGGTTGGA GAGCCAGGCC CTGGCCAGCA ACTGGCACAG     300

GTTCAGGTAA CCCTGCTTGT CCCGCACCAA CAGCAGCAGG CGGGTCGGCT TGTCGCGCTC     360

GTCGTGATTG GTGATCCACA CGTCAGCCCC GACGATGGGC TTCACGCCCT TGCCACGCGC     420

TTCCTTGTAG ANGCGCACCA GCCCGAAGGC ATTGGCGAGA TCGGTCAGCG CCAAGGCGCC     480

CATGCCATCT TTGGCGGCAG CCTTGACGGC ATCGTCGAGA CGGACATTGC CATCGACGAC     540

GGAATATTCG GAGTGGAGAC GGAGGTGGAC GAAGCGCGGC GAATTCATCC GCGTATTGTA     600

ACGGGTGACA CCTTCCGCAA AGCATTCCGG ACGTGCCCGA TTGACCCGGA GCAACCCCGC     660

ACGGCTGCGC GGGCAGTTAT AATTTCGGCT TACGAATCAA CGGGTTACCC CAGGGCGCTG     720

AAGCCTATCG CGTGCAGTTG CCGGATGC                                       748
```

(2) INFORMATION FOR SEQ ID NO: 13:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 13:

```
GCATCCGGCA ACTGCACG                                                   18
```

(2) INFORMATION FOR SEQ ID NO: 14:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 14:

```
GTAGTTCGAT GTAGAAAGCG                                                 20
```

(2) INFORMATION FOR SEQ ID NO: 15:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 15:

```
GCATCCGGCA ACTGCACG                                                   18
```

(2) INFORMATION FOR SEQ ID NO: 16:

(i) SEQUENCE CHARACTERISTICS:
        (A) LENGTH: 23 base pairs
        (B) TYPE: nucleotide
        (C) STRANDEDNESS: single
        (D) TOPOLOGY: linear

```
        (ii) MOLECULE TYPE: cDNA (xi) SEQUENCE DESCRIPTION: SEQ ID NO: 16:

AGGAGTAAGG AAACCCAACG GAC                                              23

(2) INFORMATION FOR SEQ ID NO: 17:

(i) SEQUENCE CHARACTERISTICS:
            (A) LENGTH: 19 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 17:

TAAGAGTTGC ACAAGTGCG                                                   19

(2) INFORMATION FOR SEQ ID NO: 18:

(i) SEQUENCE CHARACTERISTICS:
            (A) LENGTH: 21 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 18:

TCAGGGATAG CCCCCATCTA T                                                21

(2) INFORMATION FOR SEQ ID NO: 19:

(i) SEQUENCE CHARACTERISTICS:
            (A) LENGTH: 24 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 19:

AACCCTTTGC CACTACATCA ATTT                                             24

(2) INFORMATION FOR SEQ ID NO: 20:

(i) SEQUENCE CHARACTERISTICS:
            (A) LENGTH: 15 base pairs
            (B) TYPE: nucleotide
            (C) STRANDEDNESS: single
            (D) TOPOLOGY: linear (ii) MOLECULE TYPE: cDNA (ix) FEATURE:
            (B) LOCATION: 5, 7, 10, 13
            (D) OTHER INFORMATION: N represents inosine (i)

(xi) SEQUENCE DESCRIPTION: SEQ ID NO: 20:

GGTCNTNCCN CANGG                                                       15

(2) INFORMATION FOR SEQ ID NO: 21:

(i) SEQUENCE CHARACTERISTICS:
            (A) LENGTH: 21 base pairs
            (B) TYPE: nucleotide
            (C) STRANDEDNESS: single
            (D) TOPOLOGY: linear
```

(ii) MOLECULE TYPE: cDNA (xi) SEQUENCE DESCRIPTION: SEQ ID NO: 21:

TTAGGGATAG CCCTCATCTC T                                              21

(2) INFORMATION FOR SEQ ID NO: 22:

(i) SEQUENCE CHARACTERISTICS:
            (A) LENGTH: 21 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 22:

TCAGGGATAG CCCCCATCTA T                                              21

(2) INFORMATION FOR SEQ ID NO: 23:

(i) SEQUENCE CHARACTERISTICS:
            (A) LENGTH: 24 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 23:

AACCCTTTGC CACTACATCA ATTT                                           24

(2) INFORMATION FOR SEQ ID NO: 24:

(i) SEQUENCE CHARACTERISTICS:
            (A) LENGTH: 23 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 24:

GCGTAAGGAC TCCTAGAGCT ATT                                            23

(2) INFORMATION FOR SEQ ID NO: 25:

(i) SEQUENCE CHARACTERISTICS:
            (A) LENGTH: 18 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 25:

TCATCCATGT ACCGAAGG                                                  18

(2) INFORMATION FOR SEQ ID NO: 26:

(i) SEQUENCE CHARACTERISTICS:
            (A) LENGTH: 20 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 26:

```
ATGGGGTTCC CAAGTTCCCT                                                    20

(2) INFORMATION FOR SEQ ID NO: 27:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 27:

GCCGATATCA CCCGCCATGG                                                    20

(2) INFORMATION FOR SEQ ID NO: 28:

(i) SEQUENCE CHARACTERISTICS:
        (A) LENGTH: 18 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 28:

GCATCCGGCA ACTGCACG                                                      18

(2) INFORMATION FOR SEQ ID NO: 29:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 29:

CGCGATGCTG GTTGGAGAGC                                                    20

(2) INFORMATION FOR SEQ ID NO: 30:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 30:

TCTCCACTCC GAATATTCCG                                                    20

(2) INFORMATION FOR SEQ ID NO: 31:

(i) SEQUENCE CHARACTERISTICS:
        (A) LENGTH: 26 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 31:

GATCTAGGCC ACTTCTCAGG TCCAGS                                             26
```

(2) INFORMATION FOR SEQ ID NO: 32:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: cDNA (ix) FEATURE:
        (B) LOCATION: 6, 12, 19
        (D) OTHER INFORMATION: N represents inosine (i)

(xi) SEQUENCE DESCRIPTION: SEQ ID NO: 32:

CATCTNTTTG GNCAGGCANT AGC                                          23

(2) INFORMATION FOR SEQ ID NO: 33:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 33:

CTTGAGCCAG TTCTCATACC TGGA                                         24

(2) INFORMATION FOR SEQ ID NO: 34:

(i) SEQUENCE CHARACTERISTICS:
        (A) LENGTH: 22 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 34:

AGTGYTRCCM CARGGCGCTG AA                                           22

(2) INFORMATION FOR SEQ ID NO: 35:

(i) SEQUENCE CHARACTERISTICS:
        (A) LENGTH: 22 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 35:

GMGGCCAGCA GSAKGTCATC CA                                           22

(2) INFORMATION FOR SEQ ID NO: 36:

(i) SEQUENCE CHARACTERISTICS:
        (A) LENGTH: 22 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 36:

GGATGCCGCC TATAGCCTCT AC                                           22

(2) INFORMATION FOR SEQ ID NO: 37:

(i) SEQUENCE CHARACTERISTICS:
        (A) LENGTH: 22 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 37:

```
AAGCCTATCG CGTGCAGTTG CC                                         22
```

(2) INFORMATION FOR SEQ ID NO: 38:

(i) SEQUENCE CHARACTERISTICS:
        (A) LENGTH: 40 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 38:

```
TAAAGATCTA GAATTCGGCT ATAGGCGGCA TCCGGCAAGT                      40
```

(2) INFORMATION FOR SEQ ID NO:39:

(i) SEQUENCE CHARACTERISTICS:
        (A) LENGTH: 50 amino acids
        (B) TYPE: amino acid
        (D) TOPOLOGY: linear (ii) MOLECULE TYPE: peptide (xi) SEQUENCE DESCRIPTION: SEQ ID NO: 39:

```
Asp Ala Phe Phe Cys Ile Pro Val Arg Pro Asp Ser Gln Phe Leu Phe
  1               5                  10                  15

Ala Phe Glu Asp Pro Leu Asn Pro Thr Ser Gln Leu Thr Trp Thr Val
             20                  25                  30

Leu Pro Gln Gly Phe Arg Asp Ser Pro His Leu Phe Gly Gln Ala Leu
         35                  40                  45

Ala Gln
     50
```

(2) INFORMATION FOR SEQ ID NO:40:

(i) SEQUENCE CHARACTERISTICS:
        (A) LENGTH: 299 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 40:

```
GATGCCTTTT TCTGCATCCC TGTACGTCCT GACTCTCAAT TCTTGTTTGC CTTTGAAGAT      60

CCTTTGAACC AACGTCTCA ACTCACCTGG ACTGTTTTAC CCCAAGGGTT CAGGGATAGC      120

CCCATCTATT TGGCCAGGCA TTAGCCCAAG ATGCCTTTTG CATCCCTGTA CGTGACTCTC     180

AATTCTTGTT TGCCTTTGCC TTTGAAGATG CTTTGAACCC AACGTCTCAA CTCACCTGGA     240

CTGTTTTACG CCAAGGGTTC AGGGATAGCC CCATCTATT TGGCCAGGCA TTAGCCCAA      299
```

(2) INFORMATION FOR SEQ ID NO:41:

```
     (i) SEQUENCE CHARACTERISTICS:
         (A) LENGTH: 11 amino acids
         (B) TYPE: amino acid
         (D) TOPOLOGY: linear (ii) MOLECULE TYPE: peptide (xi) SEQUENCE DESCRIPTION: SEQ ID NO: 41:

Cys Ile Pro Val Arg Pro Asp Ser Gln Phe Leu
 1               5                  10

(2) INFORMATION FOR SEQ ID NO:42:

(i) SEQUENCE CHARACTERISTICS:
         (A) LENGTH: 17 amino acids
         (B) TYPE: amino acid
         (D) TOPOLOGY: linear (ii) MOLECULE TYPE: peptide (xi) SEQUENCE DESCRIPTION: SEQ ID NO: 42:

Val Leu Pro Gln Gly Phe Arg Asp Ser Pro His Leu Phe Gly Glu Ala
 1               5                  10                  15
Leu
 17

(2) INFORMATION FOR SEQ ID NO:43:

(i) SEQUENCE CHARACTERISTICS:
         (A) LENGTH: 8 amino acid
         (B) TYPE: amino acid
         (D) TOPOLOGY: linear (ii) MOLECULE TYPE: peptide (xi) SEQUENCE DESCRIPTION: SEQ ID NO: 43:

Leu Phe Ala Phe Glu Asp Pro Leu
 1               5           8

(2) INFORMATION FOR SEQ ID NO:44:

(i) SEQUENCE CHARACTERISTICS:
         (A) LENGTH: 8 amino acids
         (B) TYPE: amino acid
         (D) TOPOLOGY: linear (ii) MOLECULE TYPE: peptide (xi) SEQUENCE DESCRIPTION: SEQ ID NO: 44:

Phe Ala Phe Glu Asp Pro Leu Asn
 1               5           8

(2) INFORMATION FOR SEQ ID NO:45:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO: 45:

GTGCTGATTG GTGTATTTAC AATCC                                      25

(2) INFORMATION FOR SEQ ID NO:46:

(i) SEQUENCE CHARACTERISTICS:
```

(A) LENGTH: 1859 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

GTGCTGATTG GTGTATTTAC AATCCTTTAT CTAATCCGAA ATGCCCATGT TGCAATATGG      60

AAAGAAAGGG AGTTCCTAAC CTCTGGGGGA ACCCCCATTA AATACCACAA GTAAATCATG     120

GAGTTATTGC ACACAGTGCA AAAACTCAAG GAGGTGGAAG TCTTACACTG CCAAAGCCAT     180

CAGAAAAGGG AAGAGGGGAG AAGAGCAGCA TAAGTGGCTA CAGAGGCAAG GAAAGACTAG     240

CAGAAAGGAA AGAGAGAAAG AGACAGAAAG TCAGAGAGAG AGAGAGGAAG AGACAGAGCA     300

CAAAGAGGGA GTCAGAGAGA GAGAGAGACA GAGAGTCAGA GAGAAGGAAA GAGAGAGAGG     360

AAGAGACAAA GAATGAATCA AACAGAGAGA CAGAAAGTCA GAGAGAGAGA GAGAGAGGAA     420

GAGACAGAGA AAAGAGGGA GTCAGAAAAA GAGAGACCAA AGAAGAAGTC CAAAGAGAAA      480

GAAAGAGAGA TGGAAGTAGT AAAGGAAAAA CAGTGTACCC TATTCCTTTA AAAGCCGGGG     540

TAAATTTAAA ACCTATAATT GATAACTGAA GGTCTTCTCT GTAACCCTGT AACACTCCAA     600

TACCACCTTG TTGTCAAGTG TAAACAAGGG CGTAGCCCAA AAGCACTGAG GCCACTAACA     660

ACCCATAGCC TTCCTATCAA AATTCCTTAA CCCAGCAGGT TTCCTAACAG GGGATCTAAA     720

TCTTAATTAA TTACCATACA ATGGTCCAAC CAGACTTAGG AGGAATTCCC TTCAGGACGG     780

GAAGATAGAT GCTTCCTCCC AGGCGATTAA GGGAGAAAGA CACAATGGGT ATTCAGTAAG     840

TGCCAAGGGG AACACTTGTA GAAGCAAAGT TAGGAAAATT GCCAAATAAT TGGTTTGCTC     900

AAGAGTTGTT TGCACTCAGC CAAACCTTGA AGTACTTGCA GAATCAGAAA GGAGCCATCT     960

ATACCAATTC TAAGTTAATA TGGACTGAAG GAGGTTTTAT TAATACCAAA GAGAAATTAA    1020

AATCCCAAAC TTATAAGGTT TTCAACCAAA GTAAAGTTTG CTAAAAGTTA ACAGCGTAAC    1080

ATGTATTATC CTACTACCAC ACACTCTCAA AGGATTTCTC AGACAGTTTG CAAGAAATAA    1140

TGATATCTAT CCTTACTCTA CAATCCCAAA TAGACTCTTT GGCAGCAGTG ACTCTCCAAA    1200

ACCGTCAAGG CCTAGACCTC CTCACTGCTG AGAAAGGAGG ACTCTGCACC TTCTTAAGGG    1260

AAGAGTGTTG TCTTTACACT AACCAGTCAG GGATAGTATG AGATGCTGCC CGGCATTTAC    1320

AGAAAAAGGC TTCTGAAATC AGACAACGCC TTTCAAATTC CTATACCAAC CTCTGGAGTT    1380

GGGCAACATG GTTTCTTCCC TTTCTATGTC CCATGGCTGC CATCTTGCTA TTACTCGCCT    1440

TTGGGCCCTG TATTTTTAAC CTCCTTGTCA AATTTGTTTC TTCTAGGATC GAGGCCATCA    1500

AGCTACAGAT GGTCTTACAA ATGGAACCCC AAATGAGCTC AACTATCAAC TTCTACTGAG    1560

GACCCCTAGA CCAACCCCCT GGCCCTTTCA CTGGCCTAAA GAGTTCCCCT CTGGAGGACA    1620

CTACCACTGC AGGGCCCCAT CTTTGCCCCT ATCCAGAAGG AAGTAGCTAG AGCAGTCATT    1680

GCCCAATTCC CAAGAGCAGC TGGGGTGTCC CGTTTAGAGT GGGGATTGAG AGGTGAAGCC    1740

AGCTGGACTT CTGGGTCGGG TGGGGACTTG GAGAACTTTT GTGTCTAGCT AAAGGATTGT    1800

AAATGCAACA ATCAGTGCTC TGTGTCTAGC TAAAGGATTG TAAATACACC AATCAGCAC     1859

(2) INFORMATION FOR SEQ ID NO:47:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 47:

TGATGTGAAC GGCATACTCA CTG                                            23

(2) INFORMATION FOR SEQ ID NO:48:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 48:

CCCAGAGGTT AGGAACTCCC TTTC                                           24

(2) INFORMATION FOR SEQ ID NO:49:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 49:

GCTAAAGGAG ACTTGTGGTT GTCAG                                          25

(2) INFORMATION FOR SEQ ID NO: 50:

(i) SEQUENCE CHARACTERISTICS:
            (A) LENGTH: 22 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 50:

CAACATGGGC ATTTCGGATT AG                                             22

(2) INFORMATION FOR SEQ ID NO: 51:

(i) SEQUENCE CHARACTERISTICS:
            (A) LENGTH: 400 base pairs
            (B) TYPE: nucleotide
            (C) STRANDEDNESS: single
            (D) TOPOLOGY: linear (ii) MOLECULE TYPE: cDNA (xi) SEQUENCE DESCRIPTION: SEQ ID NO: 51:

GGCTGCTAAA GGAGACTTGT GGTTGTCAGA CAATCGCCTA CTTAGGTACC AGGCCTTATT     60

ACTTGAGGGA CTGGTGCTTC AGATGCGCAC TTGTGCAGCT CTTAACCCAA ACTTATGCTG    120

CCCAGAAGGA TCTTTTAGAG GTCCCCTTAG CCAACCCTGA CCTCAACCTA TATATATACT    180

GATGGAAGTT CGTTTGTAGA AAAGGGATTA CAAAGGGNAG GATATNCCAT AGGTTAGTGA    240

TAAAGCAGTA CTTGAAAGTA AGCCTCTTCC CCCCAGGGAC CAGCGCCCCC GTTAGCAGAA    300

CTAGTGGCAC TGACCCCGAG CCTTAGAACT TGGAAAGGGA GGAGGATAAA TGTGTATACA    360

GATAGCAAGT ATGCTTATCT AATCCGAAAT GCCCATGTTG                         400

(2) INFORMATION FOR SEQ ID NO: 52:

(i) SEQUENCE CHARACTERISTICS:
        (A) LENGTH: 2389 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 52:

```
TCAGGGATAG CCCCCATCTA TTTGGTCAGG CACTGGCCCA AGATCTAGGG ACATGCCACT      60

TTTAAGAGCC ATTTCTCAAG TCCAGGTACT CTGGTCCTTC GGTATGTGGA TGATTTACTT     120

TTGGCTACCA GTTCAGTAGC CTCATGCCAG CAGGCTACTC TAGATCTCTT GAACTTTCTA     180

GCTAATCAAG GGTACAAGGC ATCTAGGTTG AAGGCCCAGC TTTGCCTACA GCAGGTCAAA     240

TATCTAGGCC TAATCTTAGC CAGAGGGACC AGGGCACTCA GCAAGGAACA AATACAGCCT     300

ATACTGGCTT ATCCTCACCC TAAGACATTA AAACAGTTGC GGGGGTTCCT TGGAATCACT     360

GGCTTTTTGG TGACTATGGA TTCCCAGATA CAGCAAGATT GGCAGGCCCC TCTATACTGT     420

AATCAAGGAG ACTCACGAGG GCAAGTACTC ATCTAGTAGA ATGGGAACTA GGACAGAAA      480

CAGCCTTCAA AACCTTAAAG CAGGCCCTAG TACAATCTCC AGCTTTAAGC CTTCCCACAG     540

GACAAAACTT CTCTTTATAC ATCACAGAGA GGGCAGAGAT AGCTCTTGGT GTCCTTATTC     600

AGACTCATGG GACTACCCCA CAACCAGTGG CACACCTAAG TAAGGAAATT GATGTAGTAG     660

CAAAAGGCTG GCCTCACTGT TTATGGGTAG CTGTGGTGGT GGCTGTCTTA GTGTCAGAAG     720

CTATCAAAAT AATACAAGGA AAGGATCTCA CTGTCTGGAC TACTCATGAT GTAATGGCAT     780

ACTAGGTGCC AAAAGAAGTT TATGGGTATC AGACAACCAC CTGCTTAGAT ACCAGGGACT     840

ACTCCTGGAG GATTGGGCTT CAAGTGCGTT TTTTGTGGCC TCAACCCTGC CACTTTTCCT     900

CCAGAGGATG GAGAGCCGCT TGAGCATGCT TGCCAACAGG TTGTAGGCCA GAATTATTCC     960

ACCCGAGATG ATCTCTTAGA GTACCCTTAG CTAATCCTGA CCTTAACCTA TATACCAATG    1020

GAAGTTCATT TGTGGAAAAC GGGATATGAA GGGCAGGTTA TGTCATAGTT AGTGATGTAA    1080

TCATACTTGC AAGTAAGCCT CTTACCCCAG GGGCCAGCAC TCAGTTAGCA GAACTAGTCA    1140

CACTTACCTT AACCTTAGAA CTGGGAAAGG GAAAAAGAAT AAATATGTAT ACAGATAGTA    1200

AGTATGCTTA TCTAATCCTA CATGCCCATG CTGCAATATG GAAGGAAAGG GAGTTCCTAA    1260

CCCCTGGGGG AACCCCCATT AAATACCACA AGGYAAATCA TGGAGTTATT GCACGCAGTG    1320

CAAAAACTCA AGGAGGTGGC AGTCTTACAC TGCCGAAGCY ATCAAAAAGG GGAAGGAGAG    1380

GGGAGAACAG CAGCATAAGT GGTTGGCAGA GGCAGTGAAA GACCAGCAGA GAGAAGGAGA    1440

GAGACAACGT CAACGACAGA AGGAAAGAAG AGGAGGAGAC AGAGAGGAAG AGACAGAGAG    1500

ACAGTTAGTC CAAGAGAGAG ACAGAGAGAG GAAGAGACAG ACAGAAAGTC CAAGAGAGAA    1560

GGAAAGAGAG GAAGAGACCA AGGAGTCCNA GAGAGAGAAA GAGATAGAAG TAGTAAAGAA    1620

AAAACATTGT ACCCTATTCC TTTAAAAGCC GGGGTATATT TAAAACCTAT AATTGATAAT    1680

TGAGTTCTTG CACCCTCCTC CAGGGGATYG CTGGGAGGAA ACCCTCAACC GATATGTGAA    1740

AATTGTGGGT CGTCCCTATG TCTCAATTAC CAGCCAATAC CCCCTTGTTT TTAGTGTGAA    1800

CGAGGGTGTA GAGCGCAGAC AGGGAGACCT CTGACAATCC ATACCCTTCC TATCCAAAAT    1860

CCTTAACCCA GCAGGTTTTC TAAAAGGGGA TCTAAATCTT AATTAATTAC CATACAAAGG    1920

TCAAACCAGA TCTAGGAGGA ACTTCCTTCA GGACAGGATG ATAGATGGTT CCTCCCAGGC    1980
```

-continued

| | | | | |
|---|---|---|---|---|
| GATTAAAGAA | AATAAAAAGA | CACATGGGCA | GCCAGTAAGT GATAAGGGAA | CACTAGTAGA | 2040 |
| AGCAGTTAGG | AGAAGTTGCC | TAATAATTGG | TCTACTCCAA ATGTGTGAGT | TGTTCGCACT | 2100 |
| CAGCCCAAAT | CTTAAAGTAC | TTACAGAATT | AGGGAGGAGC CATTTACACC | AATTCTAAGT | 2160 |
| TAATATGGAC | TGGATGAGGT | TTTATTAATA | GCGAAGGAGA ATTAAATCCT | AAACTNACAA | 2220 |
| GGTTTTCAAC | TAAAGTAAAT | TTTACTAAAA | GCTAACAGTG TAACATGCAT | TATCCTACTA | 2280 |
| CAACACACTC | TCANAGGATT | CCTCAGACAG | TTTACAAGAA ATAACAAAAT | CTATCTGGTA | 2340 |
| AGGATAGTAA | CTACAATCCC | AAATACATTC | TTTGGCAGCA GTGACTCTC | | 2389 |

(2) INFORMATION FOR SEQ ID NO: 53:

(i) SEQUENCE CHARACTERISTICS:
        (A) LENGTH: 2448 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 53:

| | | | | | |
|---|---|---|---|---|---|
| TCAGGGATAG | CCCCCATCTA | TTTGATCAGG | CACTAGCCCA | AGATCTAGGC CACTTCTGAA | 60 |
| GTCCAGGCAT | TCTAGTCCTT | CAGTATGTGG | ATGATTTACT | TTTGGCTACC AGTTTGGAAG | 120 |
| CCTCATGCCA | GCAGGCTACT | TGAGATCTCT | TGAACTTTCT | AGCTAATCAA GGGTGTATGG | 180 |
| CATCTAAATT | GAAAGTCCAG | CTCTGCCTAC | AACAAGTCAA | ATATCTAGGC CTAATCTTAG | 240 |
| ATAGAAGAAC | CAGGGCCCTC | AGCAAGGAAT | GAATAAAGCC | TATGCTGGCT TATCGGCACC | 300 |
| CTAAGACATT | AAAACAATTG | TGGGGGTTCC | TTGGAATCAC | TGGCTTTTGC CGACTATGGA | 360 |
| TCCCTGGATA | GAGTGAGATA | GCCAGGCCCC | CTCTATTACT | CTTATCAAGG AGACCCAGAG | 420 |
| GGCAAATACT | TATCTAGTAT | TATGGGNACC | AGAGGCAGAA | AAAGCCTTCC AAACCTTAAA | 480 |
| GGAGACCCTA | GTACAAGCTC | CAGCTTTAAG | CCTTCCCACA | GGACAAANCT TCTCTTTATA | 540 |
| TGTCACAGAG | AGAGCAGGAA | TAGCTCCTGG | AGTCCTTACT | CAGACTTTTG GACGACCCCA | 600 |
| CGGCCAGTGG | CRTACCTAAG | TAAGGAAATT | GATGTAGTAG | CAAAAGGCTG GCCTCACTGT | 660 |
| TTATGGGTAG | TTGCGGCTGT | GGCAGTCTTA | CTGTCAAAGG | CTATCAAAAT AATACAAGGA | 720 |
| AAGGATTTCA | CTATCTGGAC | TACTCATGAG | GAAAATGGCA | TATTAGGTGC CAAAGGAAGT | 780 |
| TTTTGGCTAT | CAGACAACCA | CCTGCTCAGA | TTCCAGGCAC | TACTGATTGA GAGACCAGTG | 840 |
| CTTTAAATAT | GTATGTGTGT | GTGTGGCCCT | CAACCCTGCC | ACTGTTCTCC CAGAAGATGG | 900 |
| AGAACCAATG | AAGCATTACT | GTCAACAAAT | TAGAGTCCAG | AGTTATGCTG CCTGAGAGGA | 960 |
| TCTCTTAGAA | GTCCCCTTAG | CTAATCCTGA | CCTTAACCTA | TATGCTGATG GAAGTTCACT | 1020 |
| TGTGGAGAAT | GGGATACGAA | AAGCACATTA | TGCCATAGTT | AGTGAGGTAA CAGTACTTGA | 1080 |
| AAGTAAGCCT | ATTCCCCCAT | GGACCAGAGC | CCAGTTAGCA | GAACTAGTGG CACTTACCCA | 1140 |
| AGCCTTAGAA | CTAGGAAAGG | GAAAAATAAT | AAATGTGTAT | ACAGATAGCA AGTATGCTTA | 1200 |
| TCTAATCCTA | CATGCCCATG | CTGCAGTATG | GAAAGAAAGG | GAGTTCCTAA CCTCTGGGGG | 1260 |
| AACCCCCATT | AAATACCACA | AGGCAAATCA | TGGAGTTATT | GCATGTAGTG CAAAACCTCA | 1320 |
| AGTAGGTGGC | AGTTTTACAC | TGCCTGAAGC | TATGGGGAAG | GAGAGAGGAG AACAGCAGCA | 1380 |
| TAAGTGGCTA | GCAGAGGCAG | CGAAAGACTA | GCAGAGAGGA | GAGGTAGGGG AAAGACAGAA | 1440 |
| AGTCAAAGAA | AAGAAGTCAA | AGACAGACAG | AGAAAGAGAC | AGAGGGAGCC AGAGAGAAAG | 1500 |
| AAAAGAGAGA | ACGAAAGAGA | CAGAATGTCA | AGAACAGAA | GAGAGAGGCA GCGCCAGAAG | 1560 |

```
AGTTAAGAAA GTGAGAAAGA GAGATGGAAA TAGTAAAGAA AAAACAGTGT ACCCTATTCC    1620

TTTAAAAGCC AGGGTAAATT TAAAACGTAT AATTTTATAA TTGGAAGGTC TTCTCCATAA    1680

CCCTATAACA TTAAAATACC ACCTTGTTGT CAGTGTAAAC AAGAGCATAG CCCAAAAGCA    1740

CTGAGGCCAC TGACAACCCA TAGCCTTCCT ATCAAAAATC CTTAACTCTG CAGGTTTCCT    1800

AACAGGGGAT CTAAATCTCA ACTAATCACC ATACAATGGT CCGACCAGAC CTAGGAGCGA    1860

CTCCCCTCAG GACAGAAGGA TGGATGGTTC CTCCCAGGCC ATTAAGGGAA AGAGACACAA    1920

TGGGTATTCA GTAAGTGATA AGGGAACTCT TGTAGAAGCA GTTAGGAAGA TTGCCTAATA    1980

TTTGGTCTGC TCAAATGTGC CAGCTGTTTG CACTCAGCTA AACCTTAAAT TACTTACAGA    2040

ATTAGGAAGG AGCCATCTAT ACCAATTCTG AGTTAATATG AGCTGAACAA GTTCTTATTA    2100

ATAGCAAAGA ATCATTGAAA TCTCAAACTT GCAAAGTTTT CAACAAAAGT AAAGTTTGCT    2160

GAAAGTTAGC AGTGTAACAT GTATTATCCT AACTTCTAAT CTTGTGGAAA TCAGACCCTA    2220

TCAGTGCCCC TCAAAGCTGA AGTCCATCAG CATATGGCCA TACAACTAAT ACCCTATTT     2280

ATAGGGTTAG GAATGCCCAC TGCTACAGGA ATGGGAGTAA CAGGTTTATC TACTTCATTA    2340

TCCTATTACC ACACACTCTT AAAGGATTTC TCAGACAGTT TACAAGAAAT AACAAAATCT    2400

ATCCTTACTC TNTARTCCCA AATAGRTTCT TTGGCAGCAG TGACTCTC                 2448

(2) INFORMATION FOR SEQ ID NO: 54:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 54:

CCTGAGTTCT TGCACTAACC C                                                21

(2) INFORMATION FOR SEQ ID NO: 55:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 55:

GTCCGTTGGG TTTCCTTACT CCT                                              23

(2) INFORMATION FOR SEQ ID NO: 56:

(i) SEQUENCE CHARACTERISTICS:
        (A) LENGTH: 1196 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 56:

TTCCTGAGTT CTTGCACTAA CCTCAAATGA GAGAAGTGCC GCCATAACTG CAACCCAAGA      60

GTTTGGCGAT CCCTGGTATC TCAGTCAGGT CAATGACAGG ATGACAACAG AGGAAAGATA     120

ATGATTCCCC ACAGGCCAGC AGGCAGTTCC CAGTGTAGAC CCTCATTAGG ACACAGAATC     180
```

-continued

```
AGAACATGGA GATTGGTGCC GCAGACATTT GCTAACTTGC GTGCTAGAAG GACTAAGGAA      240

AACTAGGAAG ATATGAATTA TTCAATGATG TCCACTATAA CACAGGGGAA AGGAAGAAAA      300

TCCTACTGCC TTTCTGGAGA GACTAAGGGA GGCATTGAGG AAGCATACCA GGCAAGTGGA      360

CATTGGAGGC TCTGGAAAAG GGAAAAGTTG GGAAAAGTAT ATGTCTAATA GGGCTTGCTT      420

CCAGTGTGGT CTACAAGGAC ACTTTAAAAA AGATTGTCCA ATAGAAATAA GCCACCACCT      480

CGTCCATGCC CCTTATGTCA AGGGAATCAC TGGAAGGCCC ACTGCCCCAG GGGATGAAGG      540

TCCTCTGAGT CAGAAGCCAC TAACCAGATG ATCCAGCAGC AGGACTGAGG GTGCCCGGGG      600

CAAGCGCCAG CCCATGCCAT CACCCTCACA GAGCCCCAGG TATGCTTGAC CATTGAGGGT      660

CAGAAGGGTA CTGTCTCCTG GACACTGGCG GGCCTTCTCA GTCTTACTTT CCTGTCCTGG      720

ACAACTGTCC TCCAGATCTG TCACTGTCCG AGGGGTCCTA GGACAGCCAG TCACTAGATA      780

CTTCTCCCAG CCACTAAGTT GTGACTGGGG AACTTTACTC TTCCACATGC TTTTCTAATT      840

ATGCCTGAAA GCCCCACTCT CTTGTTAGGG GAGAGACATT CTAGCAAAAG CAGGGGCCAT      900

TATACATGTG AATATAGGAG AAGGAACAAC TGTTTGTTGT CCCCTGCTTG AGGAAGGAAT      960

TAATCCTGAA GTCCGGGCAA CAGAAGGACA ATATGGACAA GCAAAGAATG CCCGTCCTGT     1020

TCAAGTTAAA CTAAAGGATT CCACCTCCTT TCCCTACCAA AGGCAGTACC CCCTCAGACC     1080

CGAGACCCAA CAAGAACTCC AAAAGATTGT AAAGGACCTA AAAGCCCAAG GCCTAGTAAA     1140

ACCAAGCAAT AGCCCTTGCA AGACTCCAAT TTTAGGAGTA AGGAAACCCA ACGGAC         1196
```

(2) INFORMATION FOR SEQ ID NO: 57:

(i) SEQUENCE CHARACTERISTICS:
        (A) LENGTH: 2391 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 57:

```
ATGATCCAGC AGCAGGACNG AGGGTGCCCG GGGCAAGCGC CAGCCCATGC CATCACCCTC       60

ACAGAGCCCC AGGTATGCTT GACCATTGAG GGTCAGAAGG GTNACTGTCT CCTGGACACT      120

GGCGGNGCCT TCTCAGTCTT ACTTTCCTGT CCTGGACAAC TGTCCTCCAG ATCTGTCACT      180

GTCCGAGGGG TCCTAGGACA GCCAGTCACT AGATACTTCT CCCAGCCACT AAGTTGTGAC      240

TGGGAACTT TACTCTTCCC ACATGCTTTT CTAATTATGC CTGAAAGCCC CACTCTCTTG       300

TTGGGGAGAG ACATTCTAGC AAAAGCAGGG GCCATTATAC ATGTGAATAT AGGAGAAGGA      360

ACAACTGTTT GTTGTCCCCT GCTTGAGGAA GGAATTAATC CTGAAGTCCG GCAACAGAA       420

GGACAATATG GACAAGCAAA GAATGCCCGT CCTGTTCAAG TTAAACTAAA GGATTCCACC      480

TCCTTTCCCT ACCAAAGGCA GTACCCCCTC AGACCCGAGA CCCAACAAGA ACTCCAAAAG      540

ATTGTAAAGG ACCTAAAAGC CCAAGGCCTA GTAAACCAA GCAATAGCCC TTGCAAGACT       600

CCAATTTTAG GAGTAAGGAA ACCCAACGGA CAGTGGAGGT TAGTGCAAGA ACTCAGGATT      660

ATCAATGAGG CTGTTGTTCC TCTATACCCA GCTGTACCTA ACCCTTATAC AGTGCTTTCC      720

CAAATACCAG AGGAAGCAGA GTGGTTTACA GTCCTGGACC TTAAGGATGC CTTTTTCTGC      780

ATCCCTGTAC GTCCTGACTC TCAATTCTTG TTTGCCTTTG AAGATCCTTT GAACCCAACG      840

TCTCAACTCA CCTGGACTGT TTTACCCCAA GGGTTCAGGG ATAGCCCCCA TCTATTTGGC      900

CAGGCATTAG CCCAAGACTT GAGTCAATTC TCATACCTGG ACACTCTTGT CCTTCAGTAC      960
```

```
ATGGATGATT TACTTTTAGT CGCCCGTTCA GAAACCTTGT GCCATCAAGC CACCCAAGAA    1020

CTCTTAACTT TCCTCACTAC CTGTGGCTAC AAGGTTTCCA AACCAAAGGC TCGGCTCTGC    1080

TCACAGGAGA TTAGATACTN AGGGCTAAAA TTATCCAAAG GCACCAGGGC CCTCAGTGAG    1140

GAACGTATCC AGCCTATACT GGCTTATCCT CATCCCAAAA CCCTAAAGCA ACTAAGAGGG    1200

TTCCTTGGCA TAACAGGTTT CTGCCGAAAA CAGATTCCCA GGTACASCCC AATAGCCAGA    1260

CCATTATATA CACTAATTAN GGAAACTCAG AAAGCCAATA CCTATTTAGT AAGATGGACA    1320

CCTACAGAAG TGGCTTTCCA GGCCCTAAAG AAGGCCCTAA CCCAAGCCCC AGTGTTCAGC    1380

TTGCCAACAG GGCAAGATTT TTCTTTATAT GCCACAGAAA AAACAGGAAT AGCTCTAGGA    1440

GTCCTTACGC AGGTCTCAGG GATGAGCTTG CAACCCGTGG TATACCTGAG TAAGGAAATT    1500

GATGTAGTGG CAAAGGGTTG GCCTCATNGT TTATGGGTAA TGGNGGCAGT AGCAGTCTNA    1560

GTATCTGAAG CAGTTAAAAT AATACAGGGA AGAGATCTTN CTGTGTGGAC ATCTCATGAT    1620

GTGAACGGCA TACTCACTGC TAAAGGAGAC TTGTGGTTGT CAGACAACCA TTTACTTAAN    1680

TATCAGGCTC TATTACTTGA AGAGCCAGTG CTGNGACTGC GCACTTGTGC AACTCTTAAA    1740

CCCAAACTTA TGCTGCCCAG AAGGATCTTT NTAGAGGTCC CCTTAGCCAA CCCTGACCTC    1800

AACTATATAT ATACTGATGG AAGTTCGTTT GTAGAAAAGG GATTACAAAG GGNAGGATAT    1860

NCCATAGGTG TTAGTGATAA AGCAGTACTT GAAAGTAAGC CTCTTCCCCC CCAGGGACCA    1920

GCGCCCCCGT TAGCAGAACT AGTGGCACTG ACCCCGCGAG CCTTAGAACT TTGGAAAGGG    1980

AGGAGGATAA ATGTGTATAC AGATAGCAAG TATGCTTATC TAATCCGAAA TGCCCATGTT    2040

GTTTATCTAA TCCGAAATGC CCATGTTGCA ATATGGAAAG AAAGGGAGTT CCTAACCTCT    2100

GGGGGAACCC CCATTAAATA CCACAAGTTA ATCATGGAGT TATTGCACAC AGTGCAAAAA    2160

CTCAAGGAGG TGGAAGTCTT ACACTGCCAA AGCCATCAGA AAAGGGAAAG GGGAGAAGAG    2220

CAGCATAAGT GGCTACAGAG GCAAGGAAAG ACTAGCAGAA AGGAAAGAGA GAAAGAGACA    2280

GAAAGTCAGA GAGAGAGAGA GGAAGAGACA GAGCACAAAG AGGGAGTCAG AGAGAGAGAG    2340

AGACAGAGAG TCAGAGAGAA GGAAAGAGAG AGAGGAAGAG ACAAAGAATG A             2391
```

(2) INFORMATION FOR SEQ ID NO: 58:

(i) SEQUENCE CHARACTERISTICS:
        (A) LENGTH: 1722 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 58:

```
TGGAGAATAG CAGCATAAGT TGGCTGGCAG AAGTAGGGAA AGACAGCAAG AAGTAAAGAA      60

AAAAARGAGA AAGTCAGAGA AAGAAAAAAA GAGAGGAAGA AACAAAGAAG AACTTGAAGA     120

GAGAAAGAAG TAGTAAAGAA AAAACAGTAT ACCCTATTCC TTTAAAAGCC AGGGTAAATT     180

TCTGTCTACC TAGCCAAGGC ATATTCTTCT TATGTGGAAC ATCAACCTAT ATCTGCCTCC     240

CCACTAACTG GACAGGCACC TGAACCTTAG TCTTTCTAAG TCCCAACATT AACATTGCCC     300

CAGGAAATCA GACCCTATTG GTACCTGTCA AAGCTAAAGT CCCGTCAGTG CAGAGCCATA     360

CAACTAATAT CCCTATTTAT AGGGTTAGGA ATGGCTACTG CTACAGGAAC TGGAATAGCC     420

GGTTTATCTA CTTCATTATC CTACTACCAT ACACTCTCAA AGAATTTCTC AGACAGTTTG     480

CAAGAAATAA TGAAATCTAT TCTTACTTTA CAATCCCAAT TAGACTCTTT GGCAGCAATG     540
```

-continued

```
ACTCTCCAAA ACCGCCGAGG CCCACACCTC CTCACTGCTG AGAAAGGAGG ACTCTGCACC      600

TTCTTAGGGG AAGAGTGTTG TTTTTACACT AACCAGTCAG GGATAGTACG AGATGCCACC      660

TGGCATTTAC AGGAAAGGGC TTCTGATATC AGACAATGCC TTTCAAACTC TTATACCAAC      720

CTCTGGAGTT GGGCAACATG GCTTCTTCCA TTTCTAGGTC CCATGGCAGC CATCTTGCTG      780

TTACTCACCT TTGGGCCCTG TATTTTTAAG CTTCTTGTCA AATTTGTTTC CTCTAGGATC      840

GAAGCCATCA AGCTACAGAT GGTCTTACAA ATGGAACCCC AAATGAGTTC AACTAACAAC      900

TTCTACCAAG GACCCCTGGA ACGATCCACT GGCACTTCCA CTAGCCTAGA GATTCCCCTC      960

TGGAAGACAC TACAACTGCA GGGCCCCTTC TTTGCCCCTA TCCAGCAGGA AGTAGCTAGA     1020

GCGGTCATCG GCCAAATTCC CAACAGCAGT TGGGGTGTCC TGTTTAGAGG GGGGATTGAA     1080

GAGGTGACAG CCTGCTGGCA GCCTCACAGC CCTCGTTGGY TCTCAGTGCC TCCTCAGCCT     1140

TGGTGCCCAC TCTGGCCGTG CTTGAGGAGC CCTTCAGCCT GCCACTGCAC TGTGGGAGCC     1200

TCTTTCTGGG CTGGACAAGG CCGGAGCCAG CTCCCTCAGC TTGCAGGGAG GTATGGAGGG     1260

AGAGATGCAG GCGGGAACCA GGGCTGCGCA TGGCGCTTGC GGGCCAGCAT GAGTTCCAGG     1320

TGGGCGTGGG CTCGGCGGGC CCCACACTCG GGCAGTGAGG GGCTTAGCAC CTGGGCCAGA     1380

CAGATGCTGT GCTCAACTTC TTCGCTGGGC CTTAGCTGCC TTCCCCGTGG GGCAGGGCTY     1440

CGGGAACMTG CAGCCTGCCC ATGCTTGAGC CCCCCACCCC GCCGTGGGTT CYTGCACAGC     1500

CCAAGCTTCC CGGACAAGCA CCACCCCTTA TCCACGGTGC CCAGTCCCAT CAACCACCCA     1560

AGGGTTGAGG AGTGCGGGCA CACAGCGCGG GATTGGCAGG CAGTTCCACT GCGGCCTTG     1620

GTGCGGGATC CACTGCGTGA AGCCAGCTGG GCTCCTGAGT CTGGTGGGGA CTTGGAGAAT     1680

CTTTATGTCT AGCTAAGGGA TTGTAAATAC ACCAATCAGC AC                        1722

(2) INFORMATION FOR SEQ ID NO: 59:

(i) SEQUENCE CHARACTERISTICS:
        (A) LENGTH: 495 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 59:

CTTCCCCAAC TAATAAGGAC CCCCCTTTCA ACCCAAACAG TCCAAAAGGA CATAGACAAA       60

GGAGTAAACA ATGAACCAAA GAGTGCCAAT ATTCCCTGGT TATGCACCCT CCAAGCGGTG      120

GGAGAAGAAT TCGGCCCAGC CAGAGTGCAT GTACCTTTTT CTCTCTCACA CTTGAAGCAA      180

ATTAAAATAG ACNTAGGTNA ATTNTCAGAT AGCCCTGATG GYTATATTGA TGTTTTACAA      240

GGATTAGGAC AATCCTTTGA TCTGACATGG AGAGATATAA TATTACTGCT AAATCAGACG      300

CTAACCTCAA ATGAGAGAAG TGCTGCCATA ACTGGAGCCC GAGAGTTTGG CAATCTCTGG      360

TATCTCAGTC AGGTCAATGA TAGGATGACA ACGGAGGAAA GAGAACGATT CCCCACAGGG      420

CAGCAGGCAG TTCCCAGTGT AGCTCCTCAT TGGGACACAG AATCAGAACA TGGAGATTGG      480

TGCCGCAGAC ATTTA                                                       495

(2) INFORMATION FOR SEQ ID NO: 60:

(i) SEQUENCE CHARACTERISTICS:
        (A) LENGTH: 2503 base pairs
        (B) TYPE: nucleotide
        (C) STRANDEDNESS: single
        (D) TOPOLOGY: linear
```

(ii) MOLECULE TYPE: cDNA (xi) SEQUENCE DESCRIPTION: SEQ ID NO: 60:

```
CCAAGAACCC ACCAATTCCG GANCACATTT TGGCGACCAC GAAGGGACTT TCGCATATCG      60
CCAAGCGGTG AGACAATAGC CGAGCGGTGA GACCTTTCCC AATCGCCAAG CAGTGAGTAC     120
CATCAGACCC CTTTCACTTG CTATTCTGTC CTATCTTTCT TTAGAATTCG GGGGCTAAAT     180
ACCGGGCATC TGTCAGCCAT TTAAAAGTGA CTAGCGGGCC GCCGGACTAA AGACACGGGT     240
GTCAAGCTTT CTGGGAAAGG GCTCTCTAAC AACCCCCAAC TCTTTGGAGT TGGGACCGTT     300
GGTTTGCCTA GAACCAGCTT CCGCTTTTCC TGTACTTCTG GGCTGAGCCG TGGGTTGACA     360
GTGAAGGAAA GCCATGCATC TCCGGGGTCT CGMCAACATG TTGGTTGACC CTGCGGCCAT     420
GAGTGGAACT CTCAAAAGCA TGTCGCCCAA GCGACACTCG CCTATCTATC CTATCTATCC     480
TGACCCTTGC CCTCTGGGTC CTAATGCCTG CCAGACAAAC TTCCTCTCGC CTCTCTTCTC     540
TGAAGCTAGA ACCGCTTCTA AAAATTGCTA CCTGGTCTCT GGTGCTTTTC CTARTTTCTC     600
CTATAAAGAA TGAWTTCTAG TATTAAACTC CAGGACTCTG TTACCTTCTT TAGGCACCCG     660
GGCTCACCAA TCAGAAAGAC ACAGTTTTTG CCCAAGGCCC CATCGTAGTG GGGACTACCT     720
GGAATTTTAG GATCCCTCCT CAGACTAACA GGCCTAACAA AAGTTATTCC TGAAGCTAGG     780
ATATGGGGAG CCTCAGAAAT TGTATCCCTC CTATTCATAT AAGTGAGAAC AAAAGGTGTC     840
ACTCTTCCAA CCCTGAAGAT CCCCTCCCTC CCTCAGGGTA TGGCCCTCCA TTTCATTTTT     900
GTGGCATAAC ATCTTTATAG GATGGGGTAA AGTCCCAATA CTAACAGGAG AATGCTTAGG     960
ACTCTAACAG GTTTTTGAGA ATGCGTCAGT AAGGGCCACT AAATCTGATT TTTCTCAGTC    1020
GGTCCTCCTT GTGGTCTAGG AGGACAGGCA AGGTTGTGCA GGTTTTCGAG AATGCGTCAG    1080
TAAGGACCAC TAAATCCGAC CTTCCTCGGT CCTCCATGTG GTCTGGGAGG AAAACTAGTG    1140
TTTCTGCTGC TGCGTCGGTG AGCGCAACTA TTCAAGTCAG CAGGGTCCAG GGACCGTTGC    1200
AGGTTCTTGG GCAGGGGTTG TTTCTGCTGC TGCATTGGTG AATGCAACTA TTCTGATCAG    1260
CAGGGTCCCA GGACCATTGC AGGTCCTTGG GCAGGGAGAG AAACAAAACA AACCAAAACT    1320
GTGGGCGGTT TTGTCTTTCA TATGGGAAAC ACTCAGGCAT CAACAGGTTC ACCCTTGAAA    1380
TGCATCCTAA GCCATTGGGA CCAATTTGAC CCACAAACCC TGAAAAAGAG GAGGCTCATT    1440
TTTTCCTGCA CTACGGCTTG GCCCCAATAT TCTCTTTYTG ATGGGAAAA ATGGCCACCT    1500
GAGGGAAGCA CAAATTACAA TAYTATCCTA CAGCYTGATC TTTTCTGTAA GAGGGAAGGC    1560
AAATGGAGTG AATACCTTAT GTCCAAGCTT TCTTTTCATT GAGGGAGAAT ACACAACTAT    1620
GCAAAGCTTG CAATTTACAT CCCACAGGAG GACCCTTCAG CTTACCCCCA TATCCTAGCC    1680
TCCCTATAGC TTCCCTTCCT ATTGATGATA CTCCTCCTCT AATCTCCCCT GCCCAGAAGG    1740
AAATAAGCAA AGAAATCTCC AAAGGTCCAC AAAAACCCCC GGGCTATCGG TTATGTCCCT    1800
TCAAGYTGTA GGGGGAGGGG AATTTGGCCC AACCCGGGTG CATGTCCCTT CTCCCTCTCT    1860
GATTTAAAGC AGATCAAGGC AGACCTGGGG AAGTTTTCAG ATGATCCTGA TAGGTACATA    1920
GATGTCCTAC AGGGTCTAGG GCAAACCTTT GACCTCACTT GGAGAGACGT CATGCTACTG    1980
TTAGATCAAA CCCTGGCCTT TAATGAAAAG AATGCGGCTT TAGCTGCAGC CTGAGAGTTT    2040
GGAGATACCT GGTATCCTAG TCAAGTAAAT GAAAGAATGA CAGCCGAAGA AAGGGACAAC    2100
TTCCTTACTG GTCAGCAACC CATCCCCAGT ATGGATCCCC ACTGGGACTT TGACTCAGAT    2160
CATGGGGACT GGAGTCGTAA ACATCTGTTG ATCTGTGTTC TGGAAGGACT AAGGAGAATT    2220
```

-continued

| GGGAAAAAGC CCATGAATTA TTCAATGATA TCCACCATAA CCCAGGGAAA GGAAGAAAAT | 2280 |
| CCTTCTGCCT TCCTCGAGCG GCTACAAGAG GCCTTAAGAA AATATACTCC CCTGTCACCC | 2340 |
| GAATCACTCG AGGGTCAATT GATTCTAAAA GATAAGTTTA TTACCCAATC AGCCACAGAT | 2400 |
| ATCAGGAGAA AGCTCCAAAA GCAAGCCCTG AGCCTGAACA AAATCTAGAG ACATTATTAA | 2460 |
| ACCTGGCAAC CTTGGTGTTC TATAATAGGG ACCAAGAGGA ACA | 2503 |

(2) INFORMATION FOR SEQ ID NO: 61:

(i) SEQUENCE CHARACTERISTICS:
        (A) LENGTH: 1167 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 61:

| AAGGAAACTC AGAAAGCCAA TACCCATTTA GTAAGATGGA CACCAGAAGC AGAAGCAGCT | 60 |
| TTCCAGGCCC TAAAGAAATC CCTAACCCAA GCCCCAGTGT TAAGCTTGCC AACGGGGCAA | 120 |
| GACTTTTCTT TATATGTCAC AGAAAACAG GAATAGCTCT AGGAGTCCTT ACACAGGTCC | 180 |
| AAGGGACAAG CTTGCAACCT GTGGCATACC TGAGTAAGGA AACTGATGTA NTGGCAAAGG | 240 |
| GTTGGCCTCA TTGTTTACAG GTAGGGCAGC AGTAGCAGTC TTAGTTTCTG AAACAGTTAA | 300 |
| AATAATACAG GGAAGAGATC TTACTGTGTG GACATCTCAT GATGTGAACG GCATACTCAC | 360 |
| TGCTAAAGAG GACTTGTGGC TGTCAGACAA CCATTTACTT AAATAGCAGG TTCTATTACT | 420 |
| TGAAGTGCCA GTGCTGCGAC TGCACATTTG TGCAACTCTT AACCCAGCCA CATTTCTTCC | 480 |
| AGACAATGAA GAAAAGATAG AACATAACTG TCAACAAGTA ATTGCTCAAA CCTATGCTGC | 540 |
| TCGAGGGGAC CTTCTAGAGG TTCCCTTGAC TGATCCCGAC CTCAACTTGT ATACTGATGG | 600 |
| AAGTTCCTTG GCAGAAAAAG GACTTTGAAA AGCGGGGTAT GCAGTGATCA GTGATAATGG | 660 |
| AATACTTGAA AGTAATCGCC TCACTCCAGG AACTAGTGCT CACCTGGCAG AACTAATAGC | 720 |
| CCTCACTTGG GCACTAGAAT TAGGAGAAGG AAAAAGGGTA AATATATATT CAGACTCTAA | 780 |
| GTATGCTTAC CTAGTCCTCC ATGCCCATGC AGCAATATGG AGAGAGAGGG AATTCCTAAC | 840 |
| TTCTGAGGGA ACACCTATCA ACCATCAGGG AAGCCATTAG GAGATTATTA TTGGCTGTAC | 900 |
| AGAAACCTAA AGAGGTGGCA GTCTTACACT GCCAGGGTCA TCAGGAAGAA GAGGAAAGGG | 960 |
| AAATAGAAGG CAATCGCCAA GCGGATATTG AAGCAAAAAA AGCCGCAAGG CAGGACTCTC | 1020 |
| CATTAGAAAT GCTTATAGAA GGACCCCTAG TATGGGGTAA TCCCCTCTGG GAAACCAAGC | 1080 |
| CCCAGTACTC AGCAGGAAAA ATAGAATAGG AAACCTCACA AGGACATACT TTCCTCCCCT | 1140 |
| CCAGATGGCT AGCCACTGAG GAAGGAA | 1167 |

(2) INFORMATION FOR SEQ ID NO: 62:

(i) SEQUENCE CHARACTERISTICS:
        (A) LENGTH: 78 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 62:

| TCCAAAGGCA CCAGGGCCCT CAGTGAGGAA CGTATCCAGC CTATACTGGC TTATCCTCAT | 60 |
| CCCAAAACCC TAAAGCAA | 78 |

(2) INFORMATION FOR SEQ ID NO:63:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO: 63:

Ser Lys Gly Thr Arg Ala Leu Ser Glu Glu Arg Ile Gln Pro Ile Leu
  1           5                    10                 15

Ala Tyr Pro His Pro Lys Thr Leu Lys Gln
           20                25

(2) INFORMATION FOR SEQ ID NO: 64:

(i) SEQUENCE CHARACTERISTICS:
        (A) LENGTH: 28 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 64:

AAATGTCTGC GGCACCAATC TCCATGTT                                         28

(2) INFORMATION FOR SEQ ID NO: 65:

(i) SEQUENCE CHARACTERISTICS:
        (A) LENGTH: 30 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 65:

AAGGGGCATG GACGAGGTGG TGGCTTATTT                                    30

(2) INFORMATION FOR SEQ ID NO: 66:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 66:

GGAGAAGAGC AGCATAAGTG G                                                    21

(2) INFORMATION FOR SEQ ID NO: 67:

(i) SEQUENCE CHARACTERISTICS:
        (A) LENGTH: 25 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 67:

GTGCTGATTG GTGTATTTAC AATCC                                            25

(2) INFORMATION FOR SEQ ID NO: 68:

(i) SEQUENCE CHARACTERISTICS:
        (A) LENGTH: 34 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 68:

GACTCGCTGC AGATCGATTT TTTTTTTTTT TTTT                          34

(2) INFORMATION FOR SEQ ID NO: 69:

(i) SEQUENCE CHARACTERISTICS:
        (A) LENGTH: 30 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 69:

GCCATCAAGC CACCCAAGAA CTCTTAACTT                               30

(2) INFORMATION FOR SEQ ID NO: 70:

(i) SEQUENCE CHARACTERISTICS:
        (A) LENGTH: 30 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 70:

CCAATAGCCA GACCATTATA TACACTAATT                               30

(2) INFORMATION FOR SEQ ID NO: 71:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 71:

GCCATAACTG CAACCCAAGA GTT                                      23

(2) INFORMATION FOR SEQ ID NO: 72:

(i) SEQUENCE CHARACTERISTICS:
        (A) LENGTH: 23 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 72:

GGACGAGGTG GTGGCTTATT TCT                                      23

(2) INFORMATION FOR SEQ ID NO: 73:

(i) SEQUENCE CHARACTERISTICS:

(A) LENGTH: 25 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 73:

AACTTGCGTG CTAGAAGGAC TAAGG                                              25

(2) INFORMATION FOR SEQ ID NO: 74:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 74:

AACTTTTCCC TTTTCCAGAT CCTC                                               24

(2) INFORMATION FOR SEQ ID NO: 75:

(i) SEQUENCE CHARACTERISTICS:
        (A) LENGTH: 22 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 75:

GCATACCAGG CAAGTGGACA TT                                                 22

(2) INFORMATION FOR SEQ ID NO: 76:

(i) SEQUENCE CHARACTERISTICS:
        (A) LENGTH: 25 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 76:

CTGTCCGTTG GGTTTCCTTA CTCCT                                              25

(2) INFORMATION FOR SEQ ID NO: 77:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 77:

GAGGCTCTGG AAAAGGGAAA AGTT                                               24

(2) INFORMATION FOR SEQ ID NO: 78:

(i) SEQUENCE CHARACTERISTICS:
        (A) LENGTH: 25 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 78:

CTGTCCGTTG GGTTTCCTTA CTCCT                                                25

(2) INFORMATION FOR SEQ ID NO: 79:

(i) SEQUENCE CHARACTERISTICS:
              (A) LENGTH: 25 base pairs
              (B) TYPE: nucleotide
              (C) STRANDEDNESS: single
              (D) TOPOLOGY: linear (ii) MOLECULE TYPE: cDNA (xi) SEQUENCE DESCRIPTION: SEQ ID NO: 79:

AGGAGTAAGG AAACCCAACG GACAG                                                25

(2) INFORMATION FOR SEQ ID NO: 80:

(i) SEQUENCE CHARACTERISTICS:
              (A) LENGTH: 25 base pairs
              (B) TYPE: nucleotide
              (C) STRANDEDNESS: single
              (D) TOPOLOGY: linear (ii) MOLECULE TYPE: cDNA (xi) SEQUENCE DESCRIPTION: SEQ ID NO: 80:

TGTATATAAT GGTCTGGCTA TTGGG                                                25

(2) INFORMATION FOR SEQ ID NO: 81:

(i) SEQUENCE CHARACTERISTICS:
              (A) LENGTH: 25 base pairs
              (B) TYPE: nucleotide
              (C) STRANDEDNESS: single
              (D) TOPOLOGY: linear (ii) MOLECULE TYPE: cDNA (xi) SEQUENCE DESCRIPTION: SEQ ID NO: 81:

AGGAGTAAGG AAACCCAACG GACAG                                               25

(2) INFORMATION FOR SEQ ID NO: 82:

(i) SEQUENCE CHARACTERISTICS:
              (A) LENGTH: 26 base pairs
              (B) TYPE: nucleotide
              (C) STRANDEDNESS: single
              (D) TOPOLOGY: linear (ii) MOLECULE TYPE: cDNA (xi) SEQUENCE DESCRIPTION: SEQ ID NO: 82:

TTCGGCAGAA ACCTGTTATG CCAAGG                                               26

(2) INFORMATION FOR SEQ ID NO: 83:

(i) SEQUENCE CHARACTERISTICS:
              (A) LENGTH: 22 base pairs
              (B) TYPE: nucleotide
              (C) STRANDEDNESS: single
              (D) TOPOLOGY: linear (ii) MOLECULE TYPE: cDNA (xi) SEQUENCE DESCRIPTION: SEQ ID NO: 83:

```
CTCGATTTCT TGCTGGGCCT TA                                              22
```

(2) INFORMATION FOR SEQ ID NO: 84:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 84:

```
GTTGATTCCC TCCTCAAGCA                                                 20
```

(2) INFORMATION FOR SEQ ID NO: 85:

(i) SEQUENCE CHARACTERISTICS:
        (A) LENGTH: 20 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 85:

```
CTCTACCAAT CAGCATGTGG                                                 20
```

(2) INFORMATION FOR SEQ ID NO: 86:

(i) SEQUENCE CHARACTERISTICS:
        (A) LENGTH: 19 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 86:

```
TGTTCCTCTT GGTCCCTAT                                                  19
```

(2) INFORMATION FOR SEQ ID NO: 87:

(i) SEQUENCE CHARACTERISTICS:
        (A) LENGTH: 433 amino acids
        (B) TYPE: amino acid
        (D) TOPOLOGY: linear (ii) MOLECULE TYPE: peptide (xi) SEQUENCE DESCRIPTION: SEQ ID NO: 87:

```
Met Ala Thr Ala Thr Gly Thr Gly Ile Ala Gly Leu Ser Thr Ser Leu
 1               5                  10                  15

Ser Tyr Tyr His Thr Leu Ser Lys Asn Phe Ser Asp Ser Leu Gln Glu
                20                  25                  30

Ile Met Lys Ser Ile Leu Thr Leu Gln Ser Gln Leu Asp Ser Leu Ala
            35                  40                  45

Ala Met Thr Leu Gln Asn Arg Arg Gly Pro His Leu Leu Thr Ala Glu
        50                  55                  60

Lys Gly Gly Leu Cys Thr Phe Leu Gly Glu Glu Cys Cys Phe Tyr Thr
65                  70                  75                  80

Asn Gln Ser Gly Ile Val Arg Asp Ala Thr Trp His Leu  Gln Glu Arg
                85                  90                  95

Ala Ser Asp Ile Arg Gln Cys Leu Ser Asn Ser Tyr Thr Asn Leu Trp
```

```
                  100                 105                 110
Ser Trp Ala Thr Trp Leu Leu Pro Phe Leu Gly Pro Met Ala Ala Ile
            115                 120                 125

Leu Leu Leu Leu Thr Phe Gly Pro Cys Ile Phe Lys Leu Leu Val Lys
        130                 135                 140

Phe Val Ser Ser Arg Ile Glu Ala Ile Lys Leu Gln Met Val Leu Gln
145                 150                 155                 160

Met Glu Pro Gln Met Ser Ser Thr Asn Asn Phe Tyr Gln Gly Pro Leu
                165                 170                 175

Glu Arg Ser Thr Gly Thr Ser Thr Ser Leu Glu Ile Pro Leu Trp Lys
            180                 185                 190

Thr Leu Gln Leu Gln Gly Pro Phe Phe Ala Pro Ile Gln Gln Glu Val
        195                 200                 205

Ala Arg Ala Val Ile Gly Gln Ile Pro Asn Ser Ser Trp Gly Val Leu
    210                 215                 220

Phe Arg Gly Gly Ile Glu Val Thr Ala Cys Trp Gln Pro His Ser
225                 230                 235                 240

Pro Arg Trp Xaa Ser Val Pro Pro Gln Pro Trp Cys Pro Leu Trp Pro
                245                 250                 255

Cys Leu Arg Ser Pro Ser Ala Cys His Cys Thr Val Gly Ala Ser Phe
            260                 265                 270

Trp Ala Gly Gln Gly Arg Ser Gln Leu Pro Gln Leu Ala Gly Arg Tyr
        275                 280                 285

Gly Gly Arg Asp Ala Gly Gly Asn Gln Gly Cys Ala Trp Arg Leu Arg
    290                 295                 300

Ala Ser Met Ser Ser Arg Trp Ala Trp Ala Arg Arg Ala Pro His Ser
305                 310                 315                 320

Gly Ser Glu Gly Leu Ser Thr Trp Ala Arg Gln Met Leu Cys Ser Thr
                325                 330                 335

Ser Ser Leu Gly Leu Ser Cys Leu Pro Arg Gly Ala Gly Leu Arg Glu
            340                 345                 350

Xaa Ala Ala Cys Pro Cys Leu Ser Pro Pro Arg Arg Gly Phe Leu
        355                 360                 365

His Ser Pro Ser Phe Pro Asp Lys His His Pro Leu Ser Thr Val Pro
    370                 375                 380

Ser Pro Ile Asn His Pro Arg Val Glu Glu Cys Gly His Thr Ala Arg
385                 390                 395                 400

Asp Trp Gln Ala Val Pro Leu Ala Ala Leu Val Arg Asp Pro Leu Arg
                405                 410                 415

Glu Ala Ser Trp Ala Pro Glu Ser Gly Gly Asp Leu Glu Asn Leu Tyr
            420                 425                 430

Val
433

(2) INFORMATION FOR SEQ ID NO: 88:

(i) SEQUENCE CHARACTERISTICS:
        (A) LENGTH: 693 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 88:

CTTCCCCAAC TAATAAGGAC CCCCCTTTCA ACCCAAACAG TCCAAAAGGA CATAGACAAA      60
```

-continued

```
GGAGTAAACA ATGAACCAAA GAGTGCCAAT ATTCCCTGGT TATGCACCCT CCAAGCGGTG      120

GGAGAAGAAT TCGGCCCAGC CAGAGTGCAT GTACCTTTTT CTCTCTCACA CTTGAAGCAA      180

ATTAAAATAG ACNTAGGTNA ATTNTCAGAT AGCCCTGATG GYTATATTGA TGTTTTACAA      240

GGATTAGGAC AATCCTTTGA TCTGACATGG AGAGATATAA TATTACTGCT AAATCAGACG      300

CTAACCTCAA ATGAGAGAAG TGCTGCCATA ACTGGAGCCC GAGAGTTTGG CAATCTCTGG      360

TATCTCAGTC AGGTCAATGA TAGGATGACA ACGGAGGAAA GAGAACGATT CCCCACAGGG      420

CAGCAGGCAG TTCCCAGTGT AGCTCCTCAT TGGGACACAG AATCAGAACA TGGAGATTGG      480

TGCCGCAGAC ATTTACTAAC TTGCGTGCTA GAAGGACTAA GGAAAACTAG AAGACTATG       540

AATTATTCAA TGATGTCCAC TATAACACAG GGGAAAGGAA GAAATCCTA CTGCCTTTCT       600

GGAGAGACTA AGGGAGGCAT TGAGGAAGCA TACCAGGCAA GTGGACATTG GAGGCTCTGG      660

AAAAGGGAAA AGTTGGGCAA ATTGAATGCC TAA                                  693
```

(2) INFORMATION FOR SEQ ID NO: 89:

(i) SEQUENCE CHARACTERISTICS:
        (A) LENGTH: 1577 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 89:

```
AACTTGCGTG CTAGAAGGAC TAAGGAAAAC TAGGAAGACT ATGAATTATT CAATGATGTC      60

CACTATAACA CAGGGGAAAG GAAGAAAATC CTACTGCCTT TCTGGAGAGA CTAAGGGAGG     120

CATTGAGGAA GCATACCAGG CAAGTGGACA TTGGAGGCTC TGGAAAAGGG AAAAGTTGGG     180

CAAATTGAAT GCCTAATAGG GCTTGCTTCC AGTGCAGTCT ACAAGGACGC TTTAGAAAAG     240

ATTGTCCAAG TAGAAATAAG CCGCCCCTCG TCCATGCCCC TTATGTCAAG GGAATCACTG     300

GAAGGCCTAC TGCCCCAGGG GACGAAGGTC CTCTGAGTCA GAAGCCACTA ACCTGATGAT     360

CCAGCAGCAG GACTGAGGGT GCCCGGGCA AGTGCCAGCC ATGCCATCA CCCTCAGAGC       420

CCCGGGTATG TTTGACCATT GAGAGCCAGG AAGTTAACTG TCTCCTGGAC ACTGGCGCAG     480

CCTTCTCAGT CTTACTTTCC TGTCCCAGAC AATTGTCCTC CAGATCTGTC ACTATCCGAG     540

GGTCCTAAG ACAGCCAGTC ACTACATACT TCTCTCAGCC ACTAAGTTGT GACTGGGGAA      600

CTTTACTCTT TTCACATGCT TTTCTAATTA TGCCTGAAAG CCCCACTCCC TTGTTAGGGA     660

GAGACATTTT AGCAAAAGCA GGGGCCATTA TACACCTGAA CATAGGAAAA GGAATACCCA     720

TTTGCTGTCC CCTGCTTGAG GAAGGAATTA ATCCTGAAGT CTGGGCAATA GAAGGACAAT     780

ATGGACAAGC AAAGAATGCC CGTCCTGTTC AAGTTAAACT AAAGGATTCT GCCTCCTTTC     840

CCTACCAAAG GAAGTACCCT CTTAGACCCG AGGCCCTACA AGGACTCAAA AGATTGTTAA     900

GGACCTAAAA GCCCAAGGCC TAGTAAAACC ATGCAGTAGC CCCTGCAATA CTCCAATTTT     960

AGGAGTAAGG AAACCCAACG GACAGTGGAG GTTAGTGCAA GATCTCAGGA TTATTAATGA    1020

GGCTGTTTTT CCTCTATACC CAGCTGTATC TAGCCCTTAT ACTCTGCTTT CCCTAATACC    1080

AGAGGAAGCA GAGTAGTTTA CAGTCCTGGA CCTTAAGGAT GCCTCTTTCT GCATCCCTGT    1140

ACATCCTGAT TCTCAATTCT TGTTTGTCTT TGAAGATCCT TTGAACCCAA TGTCTCAATT    1200

CACCTGGACT GTTTTACCCC AGGGGTTCCG GGATAGCCCC CATCTATTTG GCCAGGCATT    1260

AGCCCAAGAC TTGAGCCAAT TCTCATACCT GGACATCTTG TCCTTCGGTA TGGGATGATT    1320
```

```
TAATTTTAGC CACCCGTTCA GAAACCTTGT GCCATCAAGC CACCCAAGCG TTCTTAAATT    1380

TCCTCACTCC GTGTGGCTAC AAGGTTTCCA AACCAAAGGC TCAGCTCTGC TCACAGCAGG    1440

TTAAATACTT AGGGTTAAAA TTATCCAAAG GCACCAGGGC CCTCTGTGAG GAATGTATCC    1500

AACCTGTACT GGCTTATCTT CATCCCAAAA CCCTAAAGCA ACTAAGAAGG TCCTTGGCAT    1560

AACAGGTTTC TGCCGAA                                                   1577
```

(2) INFORMATION FOR SEQ ID NO: 90:

(i) SEQUENCE CHARACTERISTICS:
        (A) LENGTH: 182 amino acids
        (B) TYPE: amino acid
        (D) TOPOLOGY: linear (ii) MOLECULE TYPE: peptide (xi) SEQUENCE DESCRIPTION: SEQ ID NO: 90:

```
Ser Ser Ser Arg Thr Glu Gly Ala Arg Gly Lys Cys Gln Pro Met Pro
1               5                  10                  15

Ser Pro Ser Glu Pro Arg Val Cys Leu Thr Ile Glu Ser Gln Glu Val
            20                  25                  30

Asn Cys Leu Leu Asp Thr Gly Ala Ala Phe Ser Val Leu Leu Ser Cys
        35                  40                  45

Pro Arg Gln Leu Ser Ser Arg Ser Val Thr Ile Arg Gly Val Leu Arg
50                  55                  60

Gln Pro Val Thr Thr Tyr Phe Ser Gln Pro Leu Ser Cys Asp Trp Gly
65                  70                  75                  80

Thr Leu Leu Phe Ser His Ala Phe Leu Ile Met Pro Glu Ser Pro Thr
                85                  90                  95

Pro Leu Leu Gly Arg Asp Ile Leu Ala Lys Ala Gly Ala Ile Ile His
            100                 105                 110

Leu Asn Ile Gly Lys Gly Ile Pro Ile Cys Cys Pro Leu Leu Glu Glu
        115                 120                 125

Gly Ile Asn Pro Glu Val Trp Ala Ile Glu Gly Gln Tyr Gly Gln Ala
    130                 135                 140

Lys Asn Ala Arg Pro Val Gln Val Lys Leu Lys Asp Ser Ala Ser Phe
145                 150                 155                 160

Pro Tyr Gln Arg Lys Tyr Pro Leu Arg Pro Glu Ala Leu Gln Gly Leu
                165                 170                 175

Lys Arg Leu Leu Arg Thr
            180
```

(2) INFORMATION FOR SEQ ID NO: 91:

(i) SEQUENCE CHARACTERISTICS:
        (A) LENGTH: 36 base pairs
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 91:

```
AGATCTGCAG AATTCGATAT CACCCCCCCC CCCCCC                               36
```

(2) INFORMATION FOR SEQ ID NO: 92:

(i) SEQUENCE CHARACTERISTICS:
        (A) LENGTH: 22 base pairs

```
        (B) TYPE: nucleotide
        (C) STRANDEDNESS: single
        (D) TOPOLOGY: linear (ii) MOLECULE TYPE: cDNA (xi) SEQUENCE DESCRIPTION: SEQ ID NO: 92:

AGATCTGCAG AATTCGATAT CA                                                    22
```

What is claimed is:

1. An isolated nucleic acid comprising a nucleotide sequence having a succession of at least 100 contiguous monomers of a nucleotide sequence selected from the group consisting of sequences SEQ ID NO: 46, SEQ ID NO: 51, SEQ ID NO: 52, SEQ ID NO: 53, SEQ ID NO: 56, SEQ ID NO: 58, SEQ ID NO: 59, SEQ ID NO: 60, SEQ ID NO: 61, SEQ ID NO: 89 and their complementary sequences.

2. A nucleic acid according to claim 1, wherein said nucleotide sequence is selected from the group consisting of sequences SEQ ID NO: 51, SEQ ID NO: 56, SEQ ID NO: 59, SEQ ID NO: 60, SEQ ID NO: 61, SEQ ID NO: 89, their complementary sequences and nucleotide sequences having a succession of at least 100 contiguous monomers of a nucleotide sequence selected from the group consisting of said sequences SEQ ID NO: 51, SEQ ID NO: 56, SEQ ID NO: 59, SEQ ID NO: 60, SEQ ID NO: 61, SEQ ID NO: 89 and their complementary sequences.

3. An isolated nucleic acid consisting of 100 or more contiguous monomers of a nucleotide sequence selected from the group consisting of SEQ ID NO: 46, SEQ ID NO: 51, SEQ ID NO: 52, SEQ ID NO: 53, SEQ ID NO: 56, SEQ ID NO: 58, SEQ ID NO: 59, SEQ ID NO: 60, SEQ ID NO: 61, SEQ ID NO: 89 and their complementary sequences.

4. A nucleic acid according to claim 3, consisting of a nucleotide sequence selected from the group consisting of SEQ ID NO: 46, SEQ ID NO: 51, SEQ ID NO: 52, SEQ ID NO: 53, SEQ ID NO: 56, SEQ ID NO: 58, SEQ ID NO: 59, SEQ ID NO: 60, SEQ ID NO: 61, SEQ ID NO: 89 and their complementary sequences.

5. A nucleic acid according to claim 3, consisting of 100 or more contiguous monomers of a nucleotide sequence selected from the group consisting of SEQ ID NO: 51, SEQ ID NO: 56, SEQ ID NO: 59, SEQ ID NO: 60, SEQ ID NO: 61, SEQ ID NO: 89 and their complementary sequences.

6. A nucleic acid according to claim 3, consisting of a nucleotide sequence selected from the group consisting of SEQ ID NO: 51, SEQ ID NO: 56, SEQ ID NO: 59, SEQ ID NO: 60, SEQ ID NO: 61, SEQ ID NO: 89 and their complementary sequences.

7. An isolated nucleic acid comprising 100 or more contiguous monomers of a nucleotide sequence selected from the group consisting of SEQ ID NO: 46, SEQ ID NO: 51, SEQ ID NO: 52, SEQ ID NO: 53, SEQ ID NO: 56, SEQ ID NO: 58, SEQ ID NO: 59, SEQ ID NO: 60, SEQ ID NO: 61, SEQ ID NO: 89 and their complementary sequences.

8. A nucleic acid according to claim 7, wherein said nucleotide sequence is selected from the group consisting of SEQ ID NO: 51, SEQ ID NO: 56, SEQ ID NO: 59, SEQ ID NO: 60, SEQ ID NO: 61, SEQ ID NO: 89 and their complementary sequences.

* * * * *